(12) United States Patent
Schwink et al.

(10) Patent No.: US 8,828,991 B2
(45) Date of Patent: Sep. 9, 2014

(54) AZACYCLYL-SUBSTITUTED ARYLTHIENOPYRIMIDINONES, PROCESS FOR THEIR PREPARATION AND THEIR USE AS MEDICAMENTS

(75) Inventors: Lothar Schwink, Frankfurt am Main (DE); Siegfried Stengelin, Frankfurt am Main (DE); Matthias Gossel, Frankfurt am Main (DE); Gerhard Hessler, Frankfurt am Main (DE); Torsten Haack, Frankfurt am Main (DE); Petra Lennig, Frankfurt am Main (DE)

(73) Assignee: Sanofi, Paris (FR)

( * ) Notice: Subject to any disclaimer, the term of this patent is extended or adjusted under 35 U.S.C. 154(b) by 1040 days.

(21) Appl. No.: 12/191,630

(22) Filed: Aug. 14, 2008

(65) Prior Publication Data

US 2009/0082339 A1 Mar. 26, 2009

Related U.S. Application Data

(63) Continuation of application No. PCT/EP2007/001211, filed on Feb. 13, 2007.

(30) Foreign Application Priority Data

Feb. 15, 2006 (DE) .................. 10 2006 007 046

(51) Int. Cl.
| | | |
|---|---|---|
| *C07D 495/04* | (2006.01) | |
| *A61K 31/519* | (2006.01) | |
| *C07D 403/10* | (2006.01) | |
| *C07D 239/91* | (2006.01) | |
| *C07D 491/04* | (2006.01) | |
| *A61K 31/517* | (2006.01) | |
| *A61K 31/551* | (2006.01) | |
| *A61P 3/10* | (2006.01) | |
| *A61P 3/04* | (2006.01) | |
| *C12N 9/99* | (2006.01) | |

(52) U.S. Cl.
CPC .............. *C07D 491/04* (2013.01); *C12N 9/99* (2013.01); *C07D 239/91* (2013.01); *C07D 403/10* (2013.01); *C07D 495/04* (2013.01)
USPC ........... 514/218; 540/575; 544/278; 544/290; 514/260.1; 514/266.2

(58) Field of Classification Search
CPC ........................... C07D 495/04; A61K 31/519
USPC ....................... 544/278; 514/260.1
See application file for complete search history.

(56) References Cited

FOREIGN PATENT DOCUMENTS

| | | |
|---|---|---|
| WO | WO 03/033476 | 4/2003 |
| WO | WO 03/033480 | 4/2003 |
| WO | WO 2005/042541 | 5/2005 |
| WO | WO 2005/103039 | 11/2005 |

OTHER PUBLICATIONS

Abou-Zeid, K. A. M., et. al., Synthesis and Phosphodiestrerase Inhibitors Activity of Some 6-Substituted 4,5-Dihydropyridazin-3(2H)-Ones, Database Accession No. 1996:26776, Bulletin of the Faculy of Pharmacy(Cairo University) (1995), vol. 33 (Spec. Issue), 25-8, STN printout only.
El-Wassimy, M. T. M., et. al., Synthesis of Some Novel Quinazolin-4-One Derivatives of Possible Antimicrobial Activity, Database Accession No. 1993:213014, Sohag Pure & Applied Science Bulletin, vol. 7, pp. 41-49, (1991), STN printout only.
Oza, H. B., et. al., Synthesis of Some Novel Pyrazolines as Biologically Potent Agents, Database Accession No. 1997:452130, Heterocyclic Communications, vol. 3, No. 3, pp. 239-244, (1997), STN printout only.
Pandey, V. K., et. al., Synthesis and Antiviral Activity of 2-Aryl-5-[3'-(2'-Methyl-6:8 Substituted-Quinazolyl)-Phenyl]-Pyrazoles, Database Accession No. 1995:309968, Indian Drugs, vol. 31, No. 11, pp. 532-536, (1994), STN printout only.
Srivastava, B., et. al., Synthesis and QSAR of 2,3,6,8-Substituted 1,3-Quinazolin-4(4H)-Ones as Potential Anthelmintics, Database Accession No. 1991:247204, Indian Journal of Chemistry, Section B: Organic Chemistry Including Medicinal Chemistry, vol. 30B No. 3, pp. 332-339, (1991), STN printout only.

*Primary Examiner* — Susanna Moore
(74) *Attorney, Agent, or Firm* — Scully, Scott, Murphy & Presser, P.C.

(57) ABSTRACT

The invention relates to azacyclyl-substituted arylthienopyrimidinones and their derivatives, of the Formula (I);

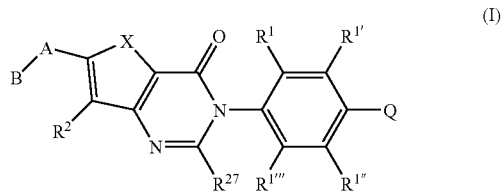

and their physiologically tolerated salts and physiologically functional derivatives, their preparation, medicaments comprising at least one azacyclyl-substituted arylthienopyrimidinone according to Formula (I) or its derivative, and the use of the azacyclyl-substituted arylthienopyrimidinones according to Formula (I) and their derivatives as MCH antagonists.

28 Claims, No Drawings

AZACYCLYL-SUBSTITUTED ARYLTHIENOPYRIMIDINONES, PROCESS FOR THEIR PREPARATION AND THEIR USE AS MEDICAMENTS

This application is a continuation of International Application No. PCT/EP2007/001211, filed Feb. 13, 2007, which is incorporated herein by reference in its entirety.

FIELD OF THE INVENTION

The invention relates to azacyclyl-substituted arylthienopyrimidinones and their derivatives, and their physiologically tolerated salts and physiologically functional derivatives, their preparation, medicaments comprising at least one azacyclyl-substituted arylthienopyrimidinone of the invention or its derivative, and the use of the azacyclyl-substituted arylthienopyrimidinones of the invention and their derivatives as medicaments.

BACKGROUND OF THE INVENTION

Compounds similar in their overall structure to the azacyclyl-substituted arylthienopyrimidinones and their derivatives described in the present application and having a pharmacological effect have been described in the prior art. Thus, for example, WO2005/042541 describes 3-(4-aminophenyl)thienopyrimid-4-one derivatives as MCH R1 antagonists for the treatment of obesity, diabetes, depressions and anxiety states. WO 03/033476 discloses bicyclic pyrimidone derivatives having an MCH R1-antagonistic effect for the treatment of obesity, and WO 03/033480 discloses lactam derivatives suitable as MCH R1 antagonists.

Further compounds having an MCH-antagonistic effect for the treatment of obesity are described in the prior art (examples: WO2005047293, WO2004092181, WO2005103039, WO2004024702, WO2001021577, WO2003035624, WO2002089729, WO2002006245, WO2002002744, WO2002057233, WO2003045313, WO2003097047, WO2002010146, WO 2003087044).

The invention was based on the object of providing compounds which bring about a weight reduction in mammals and which are suitable for the prevention and treatment of obesity and diabetes and of their diverse sequelae.

Surprisingly, a series of compounds which modulate the activity of MCH receptors has been found. In particular, the compounds are notable for an antagonism of the MCH1R.

SUMMARY OF THE INVENTION

The invention therefore relates to compounds of the formula I,

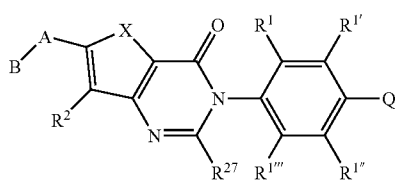

(I)

in which the meanings are

R1, R1', R1", R1'"
  independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R3)(R4), $SO_2$—$CH_3$, COOH, COO—$(C_1-C_6)$-alkyl, CON(R5)(R6), N(R7)CO(R8), N(R9)$SO_2$(R10), CO(R11), (C(R12)(R13))$_x$—O(R14);
  preferably H, F, Cl, Br, OH, $CF_3$, $NO_2$, CN, $OCF_3$, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_2-C_6)$-alkynyl, O—$(C_0-C_8)$-alkylene-aryl, CO$(C_1-C_6)$-alkyl;
  particularly preferably H, F, Cl, Br, $CF_3$, CN, $OCF_3$, O—$(C_1-C_6)$-alkyl, $(C_1-C_4)$-alkoxy-$(C_1-C_4)$-alkyl, $(C_1-C_6)$-alkyl;
  very particularly preferably H, F, Cl, O—$(C_1-C_6)$-alkyl, $(C_1-C_6)$-alkyl;
  where preferably at least two, particularly preferably at least three or all radicals R1, R1', R1" and R1'" are H;

R3, R4, R5, R6, R7, R9
  independently of one another H, $(C_1-C_8)$-alkyl;
  or
R3 and R4, R5 and R6
  form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

R8, R10, R11
  independently of one another H, $(C_1-C_8)$-alkyl, aryl; preferably independently of one another H, $(C_1-C_8)$-alkyl;

R12, R13
  independently of one another H, $(C_1-C_8)$-alkyl, preferably independently of one another H;

R14 H, $(C_1-C_6)$-alkyl, aryl; preferably independently of one another H, $(C_1-C_6)$-alkyl;

x 0, 1, 2, 3, 4, 5, 6;

R2 H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), (C(R24)(R25))$_x$, —O(R26);
  preferably H, F, Cl, Br, I, OH, $CF_3$, $NO_2$, CN, $OCF_3$, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl;
  particularly preferably H, F, Cl, Br, $CF_3$, CN, $OCF_3$, O—$(C_1-C_6)$-alkyl, $(C_1-C_4)$-alkoxy-$(C_1-C_4)$-alkyl, $(C_1-C_6)$-alkyl;
  very particularly preferably H, F, $C_{1-10}$—$(C_1-C_6)$-alkyl, $(C_1-C_6)$-alkyl;
  in particular very particularly preferably H;

R15, R16, R17, R18, R19, R21
  independently of one another H, $(C_1-C_8)$-alkyl;
  or
R15 and R16, R17 and R18
  form independently of one another and optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

R20, R22, R23
  independently of one another H, $(C_1-C_8)$-alkyl, aryl; preferably independently of one another H, $(C_1-C_8)$-alkyl;

R24, R25
  independently of one another H, $(C_1-C_8)$-alkyl;

R26 H, $(C_1-C_6)$-alkyl, aryl; preferably H, $(C_1-C_6)$-alkyl;

x' 0, 1, 2, 3, 4, 5, 6;

R27 H, $(C_1-C_6)$-alkyl, preferably H;

X S, O, C(R30)=C(R30'); preferably S, O; particularly preferably S;

R30, R30'
  independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, aryl, optionally substituted with F, Cl, Br, $O(C_1-C_6)$-alkyl, $(C_1-C_6)$-alkyl;
  preferably H, F, Cl, Br, $CF_3$, O—$(C_1-C_6)$-alkyl, $(C_1-C_4)$-alkoxy-$(C_1-C_4)$-alkyl, $(C_1-C_6)$-alkyl;
  particularly preferably H, F, $C_{1-10}$—$(C_1-C_6)$-alkyl, $(C_1-C_6)$-alkyl;
  very particularly preferably H;

A a bond or a linker having 1 to 8 members, where the members are selected from the group consisting of O, S, $SO_2$, N(R31), CO, C(R32)(R33), C(R34)=C(R34'), cycloalkylene, preferably cyclopropylene, C≡C, resulting in a chemically reasonable radical;
  preferably a bond or a linker having 1 to 6 members, where the members are selected from the group consisting of O, $SO_2$, N(R31), CO, C(R32)(R33), C(R34)=C(R34'), C≡C, resulting in a chemically reasonable radical;
  particularly preferably a bond or a linker having 1 to 5 members, where the members are selected from the group consisting of O, $SO_2$, N(R31), CO, C(R32)(R33), C≡C, resulting in a chemically reasonable radical;
  very particularly preferably a bond or a linker having 1 to 5 members, where the members are selected from the group consisting of O, $SO_2$, N(R31), CO, C(R32)(R33), C≡C, resulting in a chemically reasonable radical, where the linker contains no O—CO or CO—O groups;

R31, R34, R34'
  independently of one another H, $(C_1-C_8)$-alkyl;

R32, R33
  independently of one another H, $(C_1-C_6)$-alkyl, OH, O—$(C_1-C_6)$-alkyl;

B H, N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43), $SO_2CH_3$, $SCF_3$ or S—$(C_1-C_6)$-alkyl;
  preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;
  particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;
  very particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl, N(R42)(R43) or $SO_2CH_3$;

R35, R36, R37, R38, R39, R40, R41, R42, R43
  independently of one another H, $(C_1-C_8)$-alkyl;
or
R38 and R39, R42 and R43
  form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;
where
R35, R36, R37, R38, R39, R40, R41, R42, R43
  are preferably independently of one another H, $(C_1-C_8)$-alkyl;

Q mono-, bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44), $(C(R45)(R46))_o$—R47, CO$(C(R45)(R46))_p$—R48, where Q comprises in total at least two N atoms;
Q is preferably linked to the group

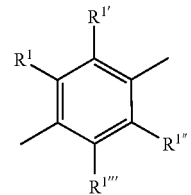

via a ring nitrogen atom of the group Q;

R44 H, $(C_1-C_8)$-alkyl;

R45, R46
  independently of one another H, $(C_1-C_8)$-alkyl, OH, $(C_3-C_8)$-cycloalkyl, $(C_1-C_4)$-alkoxy-$(C_1-C_4)$-alkyl; preferably H, $(C_1-C_6)$-alkyl; particularly preferably H;

o, p independently of one another 0, 1, 2, 3, 4, 5, 6; preferably 0, 1, 2, 3, 4;

R47, R48
  independently of one another OH, F, O—$(C_1-C_8)$-alkyl, CON(R49)(R50), N(R51)CO(R52), N(R53)(R54), $CO_2$(R55), $SO_2Me$, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, $(C_1-C_4)$-alkoxy-$(C_1-C_4)$-alkyl, CO(R56), oxo, OH;

R49, R50, R51, R52, R55, R56
  independently of one another H, $(C_1\text{-}C_8)$-alkyl;
or
R49 and R50
  form optionally together with the nitrogen atom to which they are bonded a 5-6 membered ring which, apart from the nitrogen atom, may also comprise 0-1 further heteroatoms from the group of NH, N—$(C_1\text{-}C_6)$-alkyl, oxygen and sulfur;
R53, R54
  independently of one another H, $(C_1\text{-}C_8)$-alkyl, $(C_1\text{-}C_4)$-alkoxy-$(C_1\text{-}C_4)$-alkyl, $(C_3\text{-}C_8)$-alkenyl, $(C_3\text{-}C_8)$-alkynyl, CO(R57), $(C(R58)(R59))_q$—R60, CO(C(R61)(R62))$_r$—R63, CO—O$(C_1\text{-}C_8)$-alkyl; or R53 and R54 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1\text{-}C_8)$-alkyl, $(C_1\text{-}C_6)$-alkyl, CO(R64), oxo, OH, $(C_1\text{-}C_4)$-alkoxy-$(C_1\text{-}C_4)$-alkyl, hydroxy-$(C_1\text{-}C_4)$-alkyl, CON(R65)(R66), N(R67)CO(R68), N(R69)(R70), $CO_2$(R71), $SO_2(C_1\text{-}C_6)$-alkyl;
  R53 is preferably:
    H, $(C_1\text{-}C_8)$-alkyl, $(C(R58)(R59))_q$—R60, $(C_1\text{-}C_4)$-alkoxy-$(C_1\text{-}C_4)$-alkyl, $(C_3\text{-}C_8)$-alkenyl, $(C_3\text{-}C_8)$-alkynyl, CO—$(C_1\text{-}C_8)$-alkyl, CO—O$(C_1\text{-}C_8)$-alkyl, CO(C(R61)(R62))$_r$N(R76)(R77);
  R54 is preferably:
    $(C_1\text{-}C_8)$-alkyl, $(C(R58)(R59))_q$—R60, $(C_1\text{-}C_4)$-alkoxy-$(C_1\text{-}C_4)$-alkyl, $(C_3\text{-}C_8)$-alkenyl, $(C_3\text{-}C_8)$-alkynyl;
or
R53 and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $(C_1\text{-}C_6)$-alkyl, O—$(C_1\text{-}C_8)$-alkyl, $(C_1\text{-}C_4)$-alkoxy-$(C_1\text{-}C_4)$-alkyl, hydroxy-$(C_1\text{-}C_4)$-alkyl, oxo, CO(R64), CON(R65)(R66), hydroxy, COO(R71), N(R67)CO$(C_1\text{-}C_6)$-alkyl, N(R69)(R70) or $SO_2(C_1\text{-}C_6)$-alkyl;
R53, R54 are very particularly preferably:
  $(C_1\text{-}C_8)$-alkyl$(C(R58)(R59))_q$—R60, $(C_1\text{-}C_4)$-alkoxy-$(C_1\text{-}C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1\text{-}C_6)$-alkyl, O—$(C_1\text{-}C_8)$-alkyl, $(C_1\text{-}C_4)$-alkoxy-$(C_1\text{-}C_4)$-alkyl, hydroxy-$(C_1\text{-}C_4)$-alkyl, oxo, CO(R64), hydroxy, N(R67)CO$(C_1\text{-}C_6)$-alkyl, or $SO_2(C_1\text{-}C_6)$-alkyl;
R58, R59
  independently of one another H, $(C_1\text{-}C_6)$-alkyl, OH;
R57, R61, R62, R64, R65, R66, R67, R68, R69, R70, R71
  independently of one another H, $(C_1\text{-}C_6)$-alkyl;
or
R69 and R70
  form optionally together with the nitrogen atom to which they are bonded a 5-6 membered ring which, apart from the nitrogen atom, may also comprise 0-1 further heteroatoms from the group of NH, N—$(C_1\text{-}C_6)$-alkyl, oxygen and sulfur;
q, r independently of one another 0, 1, 2, 3, 4, 5, 6;

R60, R63
  independently of one another OH, F, O—$(C_1\text{-}C_6)$-alkyl, CN, COO(R78), N(R74)CO$(C_1\text{-}C_6)$-alkyl, N(R76)(R77), CON(R72)(R73), $SO_2(C_1\text{-}C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1\text{-}C_6)$-alkyl, $(C_1\text{-}C_4)$-alkoxy-$(C_1\text{-}C_4)$-alkyl, S—$(C_1\text{-}C_6)$-alkyl, $(C_1\text{-}C_6)$-alkyl, $(C_2\text{-}C_6)$-alkenyl, $(C_3\text{-}C_8)$-cycloalkyl, O—$(C_3\text{-}C_8)$-cycloalkyl, $(C_3\text{-}C_8)$-cycloalkenyl, O—$(C_3\text{-}C_8)$-cycloalkenyl, $(C_2\text{-}C_6)$-alkynyl, N(R76)(R77), COO(R78), $SO_2(C_1\text{-}C_6)$-alkyl and COOH;
  preferably OH, F, O—$(C_1\text{-}C_6)$-alkyl, N(R74)CO$(C_1\text{-}C_6)$-alkyl, $SO_2(C_1\text{-}C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1\text{-}C_6)$-alkyl, $(C_1\text{-}C_4)$-alkoxy-$(C_1\text{-}C_4)$-alkyl, $(C_1\text{-}C_6)$-alkyl, $(C_2\text{-}C_6)$-alkenyl, $(C_2\text{-}C_6)$-alkynyl, N(R76)(R77) and $SO_2(C_1\text{-}C_6)$-alkyl;
R72, R73, R74, R76, R77, R78
  independently of one another H, $(C_1\text{-}C_8)$-alkyl;
or
R72 and R73, R76 and R77
  form independently of one another optionally together with the nitrogen atom to which they are bonded a 5-6 membered ring which, apart from the nitrogen atom, may also comprise 0-1 further heteroatoms from the group of NH, N—$(C_1\text{-}C_6)$-alkyl, oxygen and sulfur;
in the case where
Q is a monocyclic saturated 6- to 7-membered ring structure having one nitrogen atom and a further nitrogen atom, where the group Q is linked to the group

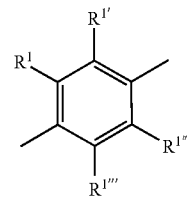

via a ring nitrogen atom of group Q;
B is a non-aromatic ring, where the further meanings for B have the meanings mentioned above for B;
and
in the case where
Q is a monocyclic saturated 5- to 7-membered ring structure having one nitrogen atom and no further heteroatom, where the ring structure is substituted by a substituent $(C(R45)(R46))_o$—R47, where
R47 is N(R53)(R54), and
the group Q is linked to the group

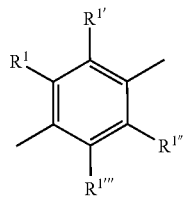

via a ring nitrogen atom of group Q;
B is not an unsubstituted phenyl ring.

DETAILED DESCRIPTION OF THE INVENTION

The compounds of the formula I are notable for exhibiting an improved solubility compared with compounds of similar structure in an aqueous media and at the same time exhibiting high activity. Preferred compounds of the invention are notable in particular for low blockade of the hERG channel. Preferred compounds of the invention further exhibit an improved metabolic stability compared with compounds of the prior art.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R27', R28, R28' R29, R29' R30, R30' R31, R32, R33, R34, R34', R35, R36, R37, R38, R39, R40, R41, R42, R43, R43', R44, R45, R46, R47, R51, R52, R53, R54, R55, R56, R57, R58, R59, R60, R61, R62, R63, R64, R65, R66, R67, R68, R69, R70, R71, R72, R73, R74, R76, R77 and R78 may be either straight-chain, branched and/or optionally substituted by substituents such as $(C_1-C_4)$-alkoxy or halogen. This also applies when the alkyl, alkenyl and alkynyl radicals are part of another group, e.g. part of an alkoxy group (such as $(C_1-C_4)$-alkoxy-$(C_1-C_4)$-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n-isomers of these radicals and branched isomers such as isopropyl, isobutyl, isopentyl, sec-butyl, tert-butyl, neopentyl, 3,3-dimethylbutyl, etc. Unless described otherwise, the term alkyl additionally also includes alkyl radicals which are unsubstituted or optionally substituted by one or more further radicals, for example by 1, 2, 3 or 4 identical or different radicals such as (C1-C4)-alkoxy or halogen. Examples of alkyl groups substituted by halogen are fluorinated alkyl groups such as CF3, CHF2, CH2F, 3-fluoroprop-1-yl, 2,2,1,1-tetrafluoroethyl. It is moreover possible for the additional substituents to appear in any desired position of the alkyl radical. Unless defined otherwise, the alkyl radicals are preferably unsubstituted.

Cycloalkyl means in the context of the present application cycloalkyl and cycloalkylalkyl (alkyl which is in turn substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as listed by way of example above for the alkyl radicals. Unless defined otherwise, the cycloalkyl radicals are preferably unsubstituted.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl.

Cycloalkenyl means in the context of the present application cycloalkenyl radicals and cycloalkenylalkyl radicals (alkyl which is substituted by cycloalkenyl), which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or non-conjugated double bonds (i.e. also alk-dienyl and alk-trienyl radicals), preferably one double bond in a linear or branched chain. The same applies to the triple bonds for alkynyl radicals. The alkenyl and alkynyl radicals may be unsubstituted or optionally substituted by one or more further radicals as listed by way of example above for the alkyl radicals. Unless defined otherwise, the alkenyl and alkynyl radicals are preferably unsubstituted.

Aryl refers in the present invention to radicals which are derived from monocyclic or bicyclic aromatic compounds comprising no ring heteroatoms. Where aryl refers to systems which are not monocyclic, the saturated form (perhydro form) or the partly unsaturated form (for example the dihydro form or tetrahydro form) is also possible for the second ring when the respective forms are known and stable. The term aryl also includes in the present invention for example bicyclic radicals in which both rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl. Unless defined otherwise, the aryl radicals are preferably unsubstituted. Aryl is particularly preferably phenyl or naphthyl.

Heteroaryl radicals mean radicals derived from monocyclic or bicyclic aromatic compounds which comprise ring heteroatoms, preferably N, O or S. Otherwise, the statements made about aryl radicals apply to heteroaryl radicals.

A "tricycle" means structures having 3 rings which are linked together by more than one bond. Examples of such systems are fused systems with 3 rings and spirocycles with fused-on ring system.

A polycyclic group (bi-, tri- or spirocyclic ring structure) means in the context of the present application a group which is derived from spiranes, fused ring systems or bridged ring systems. The spiranes are notable for two rings having only one carbon atom in common and the ring planes of the two rings being perpendicular to one another. In the fused ring systems, two rings are linked together in such a way that they have two atoms in common. This type of linkage involves an "ortho fusion". Bridged ring systems are ring systems having a bridge of carbon atoms and/or heteroatoms between two nonadjacent atoms of a ring.

A "chemically reasonable radical" means in the context of the present invention a radical which is stable at room temperature and atmospheric pressure. In the context of the present invention, a "chemically reasonable radical" in the definition of group A in compounds of the formula I preferably means groups which have no heteroatom-heteroatom bonds between the individual members of the groups.

A "nonaromatic" ring means in the context of the present application preferably a ring which is saturated or partly unsaturated. In this connection, a partly unsaturated ring according to the present application has one or, where appropriate, a plurality of double bonds, but the partly unsaturated ring is not aromatic. The term "nonaromatic" in the context of the present application also includes "nonheteroaromatic" rings.

The compounds of the formula I may have one or more centers of asymmetry. The compounds of the formula I may therefore exist in the form of their racemates, enantiomer-enriched mixtures, pure enantiomers, diastereomers and mixtures of diastereomers. The present invention encompasses all these isomeric forms of the compounds of the formula I. These isomeric forms may be obtained by known methods, even if not expressly described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion, such as, for example, trifluoroacetate, likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

If radicals or substituents may occur more than once in the compounds of the formula I, they may all have the stated meanings independently of one another and be identical or different.

The symbols in compound I preferably have independently of one another the following meanings;
in the case where
Q is a monocyclic saturated 6- to 7-membered ring structure having one nitrogen atom and a further nitrogen atom, where the group Q is linked to the group

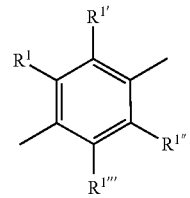

via a ring nitrogen atom of group Q;
B is a non-aromatic ring, where the further meanings for B have the meanings mentioned above for B;
and
in the case where
Q is a monocyclic saturated 5- to 7-membered ring structure having one nitrogen atom and no further heteroatom, where the ring structure is substituted by a substituent $(C(R45)(R46))_o$—R47,
where
R47 is N(R53)(R54), and
the group Q is linked to the group

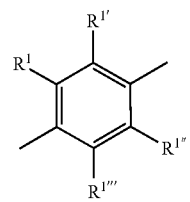

via a ring nitrogen atom of group Q;
B is not an unsubstituted phenyl ring.
R1, R1', R1", R1'''
independently of one another H, F, Cl, Br, OH, $CF_3$, $NO_2$, CN, $OCF_3$, O—$(C_1$-$C_6)$-alkyl, $(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_2$-$C_6)$-alkynyl, O—$(C_0$-$C_8)$-alkylene-aryl, CO$(C_1$-$C_6)$-alkyl;
particularly preferably H, F, Cl, Br, $CF_3$, CN, $OCF_3$, O—$(C_1$-$C_6)$-alkyl, $(C_1$-$C_4)$-alkoxy-$(C_1$-$C_4)$-alkyl, $(C_1$-$C_6)$-alkyl;
very particularly preferably H, F, $C_{1-10}$—$(C_1$-$C_6)$-alkyl, $(C_1$-$C_6)$-alkyl;
where preferably at least two, particularly preferably at least three or all radicals R1, R1', R1" and R1''' are H.
R2 H, F, Cl, Br, I, OH, $CF_3$, $NO_2$, CN, $OCF_3$, O—$(C_1$-$C_6)$-alkyl, $(C_1$-$C_4)$-alkoxy-$(C_1$-$C_4)$-alkyl, $(C_1$-$C_6)$-alkyl, $(C_2$-$C_6)$-alkenyl, $(C_2$-$C_6)$-alkynyl;
particularly preferably H, F, Cl, Br, $CF_3$, CN, $OCF_3$, O—$(C_1$-$C_6)$-alkyl, $(C_1$-$C_4)$-alkoxy-$(C_1$-$C_4)$-alkyl, $(C_1$-$C_6)$-alkyl;
very particularly preferably H, F, $C_{1-10}$—$(C_1$-$C_6)$-alkyl, $(C_1$-$C_6)$-alkyl;
in particular very particularly preferably H.
R27 is H.
X S, O; particularly preferably S;
A a bond or a linker having 1 to 6 members, where the members are selected from the group consisting of O, $SO_2$, N(R31), CO, C(R32)(R33), C(R34)=C(R34'), C≡C, resulting in a chemically reasonable radical;
particularly preferably a bond or a linker having 1 to 5 members, where the members are selected from the group consisting of O, SO$_2$, N(R31), CO, C(R32)(R33), C≡C, resulting in a chemically reasonable radical;

very particularly preferably a bond or a linker having 1 to 5 members, where the members are selected from the group consisting of O, SO$_2$, N(R31), CO, C(R32)(R33), C≡C, resulting in a chemically reasonable radical, where the linker comprises no O—CO groups;

in particular preferably a bond or a linker having 1 to 5 members, where the members are selected from the group consisting of O, N(R31), CO, C(R32)(R33), C(R34)=C(R34'), C≡C, resulting in a chemically reasonable radical; where the linker contains no O—CO or CO—O groups;

in particular particularly preferably a bond or an element selected from the group consisting of O, CH$_2$, CO, O—CH$_2$, CHOH, CH$_2$—CH$_2$, CH=CH, C(CH$_3$)=CH, C≡C, CH$_2$—O, N(CH$_3$)CO, NH—CO, CH$_2$—O—CH$_2$, O—CH=CH, C(OH)(CH$_3$)—CH$_2$—CH$_2$, C(OH)(CH$_3$)—C≡C;

in particular very particularly preferably an element selected from the group consisting of O, CH$_2$, CO, O—CH$_2$, CHOH, CH$_2$—CH$_2$, CH=CH, C(CH$_3$)=CH, C≡C, CH$_2$—O, N(CH$_3$)CO, NH—CO, CH$_2$—O—CH$_2$, O—CH=CH, C(OH)(CH$_3$)—CH$_2$—CH$_2$, C(OH)(CH$_3$)—C≡C; where R31, R34, R34'
are independently of one another H, (C$_1$-C$_8$)-alkyl;
R32, R33
are independently of one another H, (C$_1$-C$_6$)-alkyl, OH, O—(C$_1$-C$_6$)-alkyl.

In one embodiment of the present invention, A is:
A a linker having 1 to 8 members, where the members are selected from the group consisting of O, S, SO$_2$, N(R31), CO, C(R32)(R33), C(R34)=C(R34'), cycloalkylene, preferably cyclopropylene, C≡C, resulting in a chemically reasonable radical;

preferably a linker having 1 to 6 members, where the members are selected from the group consisting of O, SO$_2$, N(R31), CO, C(R32)(R33), C(R34)=C(R34'), C≡C, resulting in a chemically reasonable radical;

particularly preferably a linker having 1 to 5 members, where the members are selected from the group consisting of O, SO$_2$, N(R31), CO, C(R32)(R33), C≡C, resulting in a chemically reasonable radical;

very particularly preferably a linker having 1 to 5 members, where the members are selected from the group consisting of O, N(R31), CO, C(R32)(R33), C≡C, resulting in a chemically reasonable radical, where the linker contains no O—CO groups;

in particular preferably a bond or an element selected from the group consisting of O, CH$_2$, CO, O—CH$_2$, CHOH, CH$_2$—CH$_2$, CH=CH, C(CH$_3$)=CH, C≡C, CH$_2$—O, N(CH$_3$)CO, NH—CO, CH$_2$—O—CH$_2$, O—CH=CH, C(OH)(CH$_3$)—CH$_2$—CH$_2$, C(OH)(CH$_3$)—C≡C;

in which the radicals R31, R32, R33, R34 and R34' have the aforementioned meanings.

B H, hydroxy-(C$_1$-C$_4$)-alkyl, (C$_1$-C$_8$)-alkyl, (C$_1$-C$_4$)-alkoxy-(C$_1$-C$_4$)-alkyl, (C$_2$-C$_8$)-alkenyl, (C$_2$-C$_8$)-alkyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43) or SO$_2$CH$_3$; or where the ring system may be linked to A by =C(R43');

particularly preferably H, hydroxy-(C$_1$-C$_4$)-alkyl, (C$_1$-C$_8$)-alkyl, (C$_1$-C$_4$)-alkoxy-(C$_1$-C$_4$)-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43) or SO$_2$CH$_3$; or where the ring system may be linked to A by =C(R43');

very particularly preferably H, (C$_1$-C$_8$)-alkyl, (C$_1$-C$_4$)-alkoxy-(C$_1$-C$_4$)-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), hydroxy, N(R41)CO(C$_1$-C$_6$)-alkyl, N(R42)(R43) or SO$_2$CH$_3$; where R37, R38, R39, R40, R41, R42, R43 are
independently of one another H, (C$_1$-C$_8$)-alkyl;
or
R38 and R39, R42 and R43
form independently of one another optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur.

In a preferred embodiment, B is:
B H, N(R35)(R36), hydroxy-(C$_1$-C$_4$)-alkyl, (C$_1$-C$_8$)-alkyl, (C$_1$-C$_4$)-alkoxy-(C$_1$-C$_4$)-alkyl, (C$_2$-C$_8$)-alkenyl, (C$_2$-C$_8$)-alkynyl, a 3 to 10-membered mono-, bi-, tri- or spirocyclic nonaromatic ring which may comprise 0 to 4 heteroatoms selected from the group of oxygen, nitrogen and sulfur, where the ring system may additionally be substituted by one or more of the following substituents: F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43), SO$_2$CH$_3$, SCF$_3$ or S—(C$_1$-C$_6$)-alkyl; or where the ring system may be linked to A by =C(R43');

preferably H, hydroxy-(C$_1$-C$_4$)-alkyl, (C$_1$-C$_8$)-alkyl, (C$_1$-C$_4$)-alkoxy-(C$_1$-C$_4$)-alkyl, (C$_2$-C$_8$)-alkenyl, (C$_2$-C$_8$)-alkynyl, a 3 to 10-membered mono-, bi- or spirocyclic nonaromatic ring which may comprise 0 to 4 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43) or SO$_2$CH$_3$; or where the ring system may be linked to A by =C(R43');

particularly preferably hydroxy-(C$_1$-C$_4$)-alkyl, (C$_1$-C$_8$)-alkyl, (C$_1$-C$_4$)-alkoxy-(C$_1$-C$_4$)-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), CON(R38)(R39), hydroxy, COO(R40), N(R41)CO(C$_1$-C$_6$)-alkyl, N(R42)(R43) or SO$_2$CH$_3$;

very particularly preferably (C$_1$-C$_8$)-alkyl, (C$_1$-C$_4$)-alkoxy-(C$_1$-C$_4$)-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R37), hydroxy, N(R41)CO(C$_1$-C$_6$)-alkyl, or SO$_2$CH$_3$;

in particular preferably hydroxy-(C$_1$-C$_4$)-alkyl, (C$_1$-C$_8$)-alkyl, (C$_1$-C$_4$)-alkoxy-(C$_1$-C$_4$)-alkyl, (C$_2$-C$_8$)-alkenyl, (C$_2$-C$_8$)-alkynyl, 3-6 membered nonaromatic monocyclic ring selected from the group:

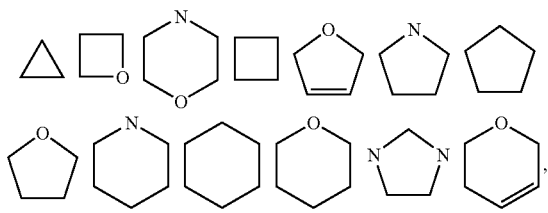

where the ring system may additionally be substituted by methyl, ethyl, OH, Oxo; in particular particularly preferably hydroxy-(C$_1$-C$_4$)-alkyl, (C$_1$-C$_8$)-alkyl, (C$_1$-C$_4$)-alkoxy-(C$_1$-C$_4$)-alkyl, (C$_2$-C$_8$)-alkenyl, (C$_2$-C$_8$)-alkynyl, 3-6 membered nonaromatic monocyclic ring selected from the group:

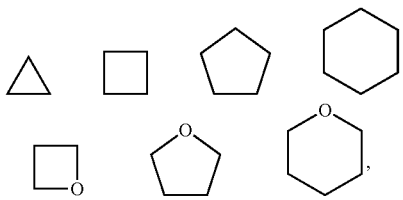

where the ring system may additionally be substituted by methyl, ethyl, OH, Oxo;
where
R35, R36, R37, R38, R39, R40, R41, R42, R43 independently of one another H, (C$_1$-C$_8$)-alkyl;
or
R38 and R39, R42 and R43
form independently of one another optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur;
where
R35, R36, R37, R38, R39, R40, R41, R42, R43 are preferably independently of one another H, (C$_1$-C$_8$)-alkyl;
Q mono-, bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, CF$_3$, CN, OCF$_3$, oxo, O—(C$_1$-C$_8$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, CO(R44), (C(R45)(R46))$_o$—R47, CO(C(R45)(R46))$_p$—R48, where Q comprises a total of at least two N atoms;

Q is preferably linked to the group

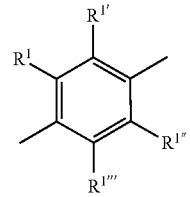

via a ring nitrogen atom of the group Q;
R44 is H, (C$_1$-C$_8$)-alkyl;
R45, R46
are independently of one another H, (C$_1$-C$_6$)-alkyl; particularly preferably H;
o, p are independently of one another 0, 1, 2, 3, 4;
R47, R48
are independently of one another OH, F, O—(C$_1$-C$_8$)-alkyl, CON(R49)(R50), N(R51)CO(R52), N(R53)(R54), CO$_2$(R55), SO$_2$Me, CN, a 3-10 membered ring system having 0 to 3 heteroatoms selected from the group of N, O and S, which may be substituted by one or more of the following substituents: F, Cl, Br, CF$_3$, (C$_1$-C$_8$)-alkyl, O—(C$_1$-C$_8$)-alkyl, (C$_1$-C$_4$)-alkoxy-(C$_1$-C$_4$)-alkyl, CO(R56), oxo, OH;
R49, R50, R51, R52, R55, R56
are independently of one another H, (C$_1$-C$_8$)-alkyl;
or
R49 and R50
form optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur;
R53 is H, (C$_1$-C$_8$)-alkyl, (C(R58)(R59))$_q$R60, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, CO—O(C$_1$-C$_8$)-alkyl, CO(C(R61)(R62))$_r$N(R76)(R77);
R54 is (C$_1$-C$_8$)-alkyl, (C(R58)(R59))$_q$R60, (C$_1$-C$_4$)-alkoxy-(C$_1$-C$_4$)-alkyl, (C$_3$-C$_8$)-alkenyl, (C$_3$-C$_8$)-alkynyl;
or
R53 and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), CON(R65)(R66), hydroxy, COO(R71), N(R67)CO(C$_1$-C$_6$)-alkyl, N(R69)(R70) or SO$_2$(C$_1$-C$_6$)-alkyl;
R53, R54 are very particularly preferably:
(C$_1$-C$_8$)-alkyl, (C(R58)(R59))$_q$— R60, (C$_1$-C$_4$)-alkoxy-(C$_1$-C$_4$)-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R64), hydroxy, N(R67)CO(C$_1$-C$_6$)-alkyl, or SO$_2$(C$_1$-C$_6$)-alkyl;
R58, R59
are independently of one another H, (C$_1$-C$_6$)-alkyl, OH;
R57, R61, R62, R64, R65, R66, R67, R69, R70, R71
are independently of one another H, (C$_1$-C$_6$)-alkyl;

or

R69 and R70
    form optionally together with the nitrogen atom to which they are bonded a 5-6 membered ring which, apart from the nitrogen atom, may also comprise 0-1 further heteroatoms from the group of NH, N—($C_1$-$C_6$)-alkyl, oxygen and sulfur;

q, r are independently of one another 0, 1, 2, 3, 4, 5, 6;

R60 is OH, F, O—($C_1$-$C_6$)-alkyl, CN, COO(R78), N(R74)CO($C_1$-$C_6$)-alkyl, N(R76)(R77), CON(R72)(R73), $SO_2$($C_1$-$C_6$)-alkyl, 3-12 membered mono-, bi- or spirocyclic ring which may comprise one or more heteroatoms from the group of N, O and S, and the 3-12 membered ring further substituents such as F, Cl, Br, OH, $CF_3$, $NO_2$, CN, $OCF_3$, oxo, O—($C_1$-$C_6$)-alkyl, ($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, N(R76)(R77), COO(R78), $SO_2$($C_1$-$C_6$)-alkyl and COOH; preferably OH, F, O—($C_1$-$C_6$)-alkyl, N(R74)CO($C_1$-$C_6$)-alkyl, $SO_2$($C_1$-$C_6$)-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—($C_1$-$C_6$)-alkyl, ($C_1$-$C_4$)-alkoxy-($C_1$-$C_4$)-alkyl, ($C_1$-$C_6$)-alkyl, ($C_2$-$C_6$)-alkenyl, ($C_2$-$C_6$)-alkyl, N(R76)(R77) and $SO_2$($C_1$-$C_6$)-alkyl;

R72, R73, R74, R76, R77, R78
    are independently of one another H, ($C_1$-$C_9$)-alkyl;
or R72 and R73, R76 and R77
    form independently of one another optionally together with the nitrogen atom to which they are bonded a 5-6 membered ring which, apart from the nitrogen atom, may also comprise 0-1 further heteroatoms from the group of NH, N—($C_1$-$C_6$)-alkyl, oxygen and sulfur.

In a preferred embodiment, Q is:

Q a group of the general formula:

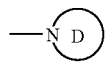

in which the ring D has the following meanings:
    saturated monocyclic 5-7-membered azacycle which comprises an element N(R53) or C(R45)(($CH_2$)$_o$—N(R53)(R54)); saturated 6-11 membered azabicycle or spirocycle which comprises an element N(R53) or C(R45)(($CH_2$)$_o$—N(R53)(R54));

Q is preferably:

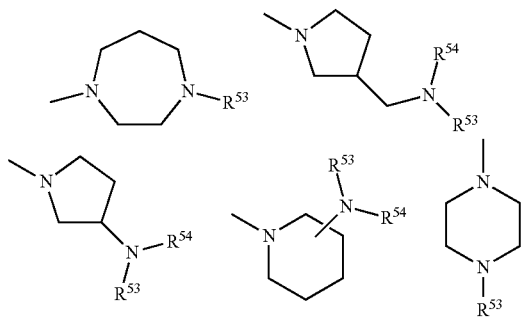

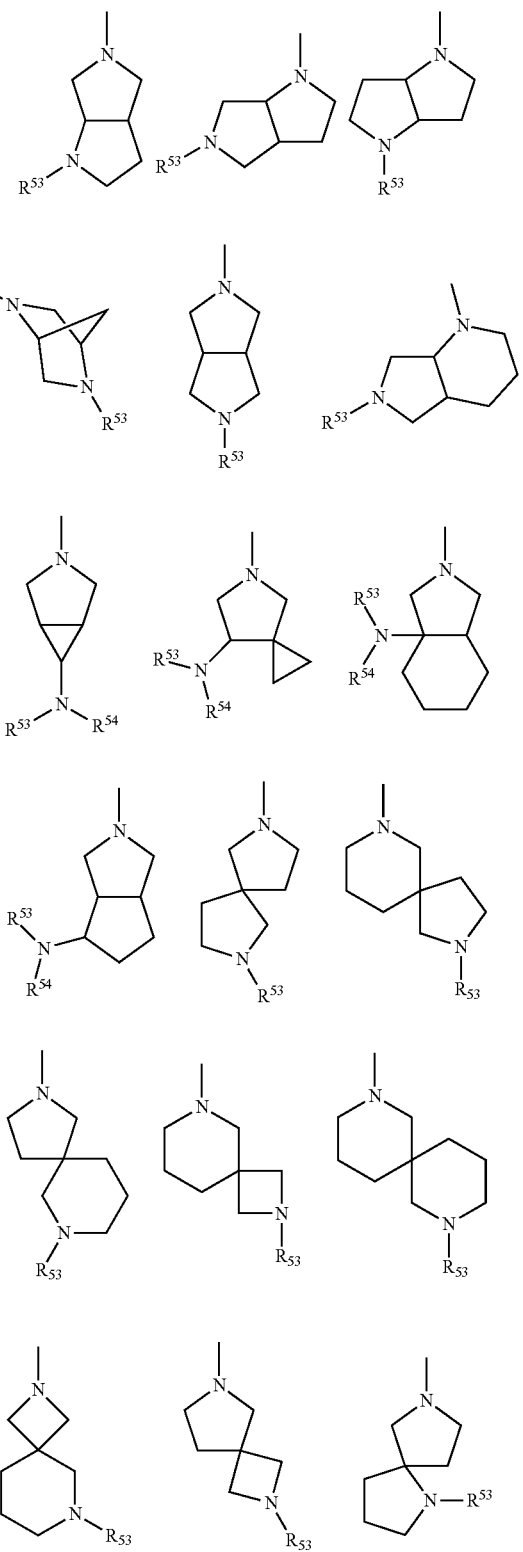

where the groups may, apart from R53 and R54, optionally be substituted by one or more substituents selected from F, OH, oxo, ($C_1$-$C_6$)-alkyl, O—($C_1$-$C_6$)-alkyl, ($C_1$-$C_4$)-alkoxy-($C_1$-$C_4$)-alkyl; the aforementioned groups Q preferably have no further substituents;

Q is particularly preferably:

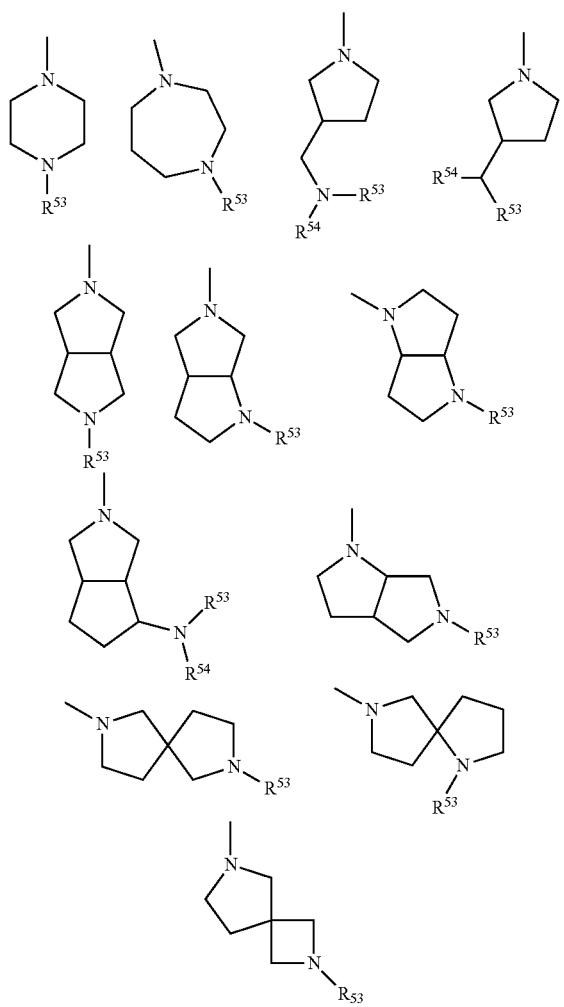

where the groups may, apart from R53 and R54, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

Q is particularly preferably:

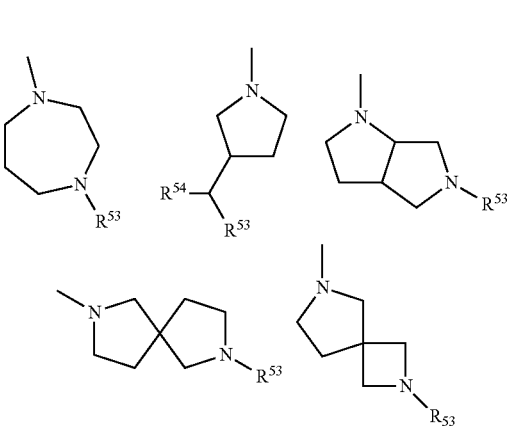

where the groups may, apart from R53 and R54, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

Q is very particularly preferably:

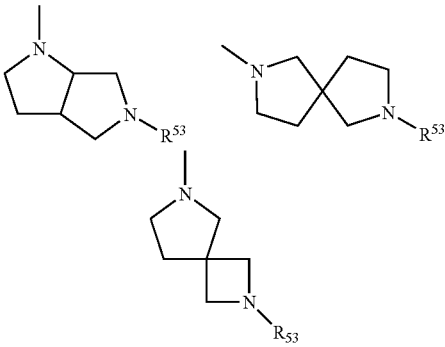

where the groups may, apart from R53, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

In a further very particularly preferred embodiment Q has the meaning:

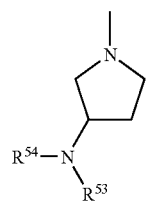

where the group may, apart from R53 and R54, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

In a further very particularly preferred embodiment Q has the meaning:

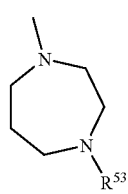

where the group may, apart from R53, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

where the radicals and groups R45, R53, R54 and o have the aforementioned meanings.

The conditions apply that
in the case where
Q is a monocyclic saturated 6- to 7-membered ring structure having one nitrogen atom and a further nitrogen atom, where the group Q is linked to the group

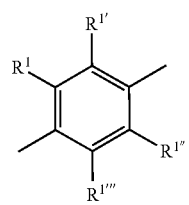

via a ring nitrogen atom of group Q;
B is a non-aromatic ring with the meanings mentioned above for B;
and
in the case where
Q is a monocyclic saturated 5- to 7-membered ring structure having one nitrogen atom and no further heteroatom, where the ring structure is substituted by a substituent $(C(R45)(R46))_o$—R47,
where
R47 is N(R53)(R54), and
the group Q is linked to the group

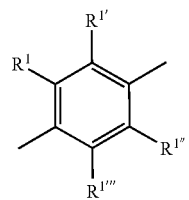

via a ring nitrogen atom of group Q;
B is not an unsubstituted phenyl ring.

In a preferred embodiment, the present invention relates to compounds of the general formula I in which X has the meaning X or O.

In a further preferred embodiment, the present invention relates to compounds of the general formula Ia

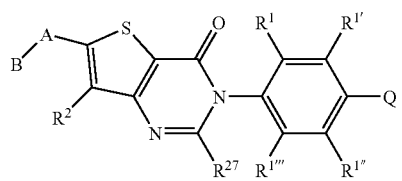

in which
Q is a group of the general formula:

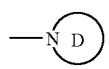

in which the ring D has the following meanings:
saturated monocyclic 5-7-membered azacycle which comprises an element N(R53) or C(R45)((CH$_2$)$_o$—N(R53)(R54)); saturated 6-11-membered azabicycle or spirocycle which comprises an element N(R53) or C(R45)((CH$_2$)$_o$—N(R53)(R54));

Q is preferably:

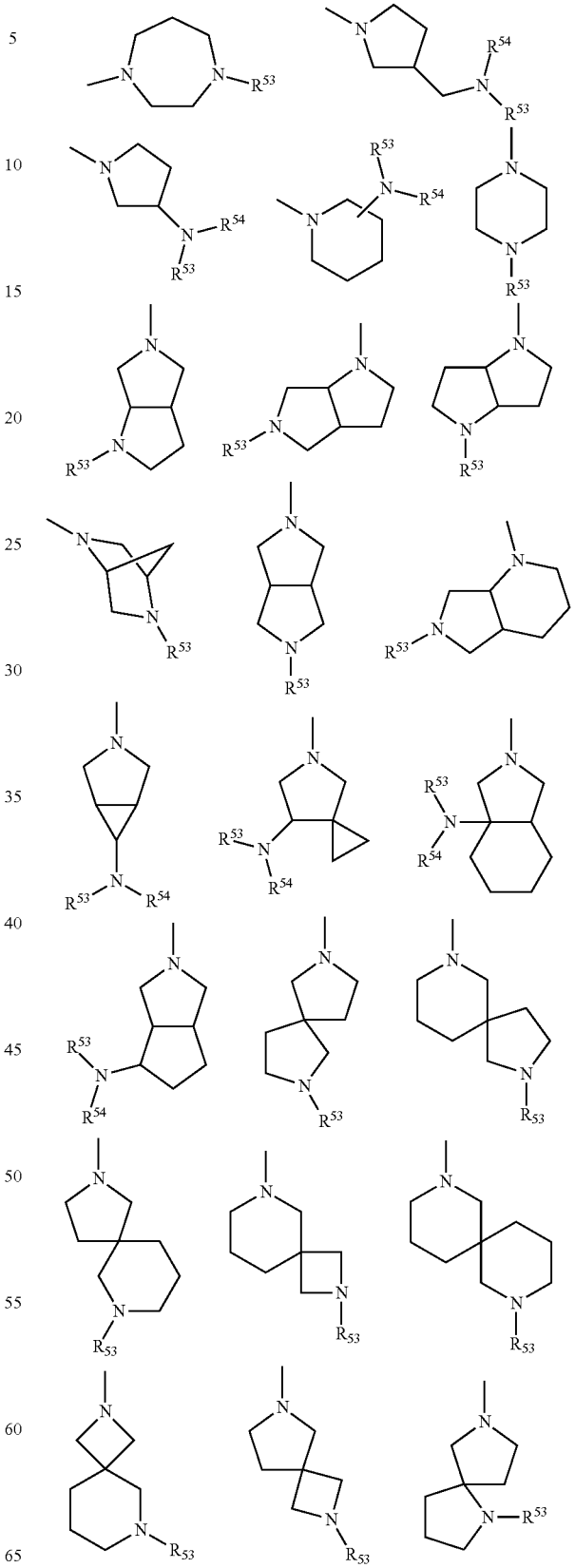

where the groups may, apart from R53 and R54, optionally be substituted by one or more substituents selected from F, OH, oxo, ($C_1$-$C_6$)-alkyl, O—($C_1$-$C_6$)-alkyl, ($C_1$-$C_4$)-alkoxy-($C_1$-$C_4$)-alkyl; the aforementioned groups Q preferably have no further substituents;

Q is particularly preferably:

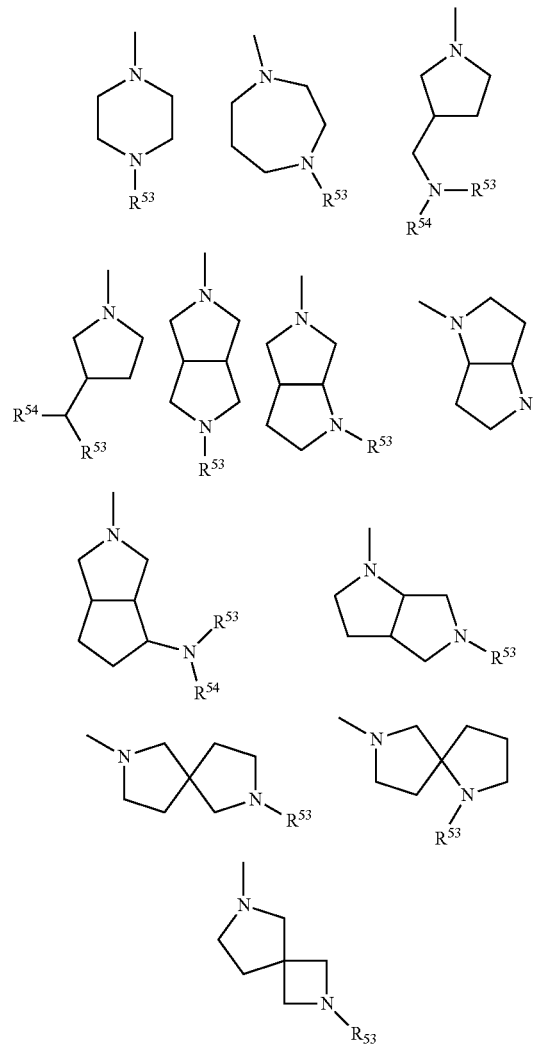

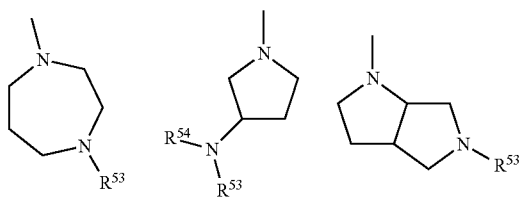

where the groups may, apart from R53 and R54, optionally be substituted by one or more substituents selected from F, OH, oxo, ($C_1$-$C_6$)-alkyl, O—($C_1$-$C_6$)-alkyl, ($C_1$-$C_4$)-alkoxy-($C_1$-$C_4$)-alkyl; the aforementioned groups Q preferably have no further substituents;

Q is particularly preferably:

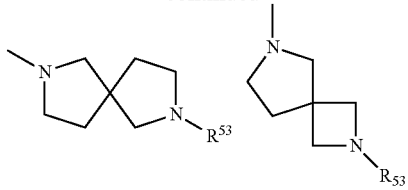

where the groups may, apart from R53 and R54, optionally be substituted by one or more substituents selected from F, OH, oxo, ($C_1$-$C_6$)-alkyl, O—($C_1$-$C_6$)-alkyl, ($C_1$-$C_4$)-alkoxy-($C_1$-$C_4$)-alkyl; the aforementioned groups Q preferably have no further substituents;

Q is very particularly preferably:

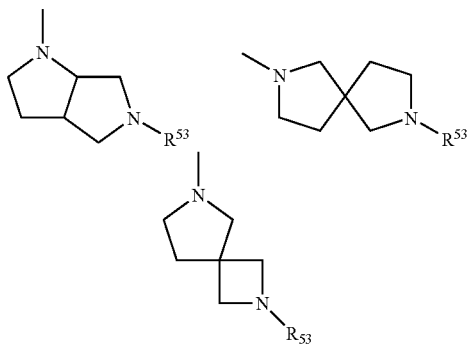

where the groups may, apart from R53, optionally be substituted by one or more substituents selected from F, OH, oxo, ($C_1$-$C_6$)-alkyl, O—($C_1$-$C_6$)-alkyl, ($C_1$-$C_4$)-alkoxy-($C_1$-$C_4$)-alkyl; the aforementioned groups Q preferably have no further substituents;

R45 H, ($C_1$-$C_6$)-alkyl; preferably H;

0, 1, 2, 3, 4, 5, 6; preferably 0, 1, 2; particularly preferably 0, 1; very particularly preferably 0;

R53, R54
independently of one another H, ($C_1$-$C_8$)-alkyl, ($C_1$-$C_4$)-alkoxy-($C_1$-$C_4$)-alkyl, ($C_3$-$C_8$)-alkenyl, ($C_3$-$C_8$)-alkynyl, CO(R57), (C(R58)(R59))$_q$—R60, CO(C(R61)(R62))$_r$—R63, CO—O($C_1$-$C_8$)-alkyl; or R53 and R54 form together with the nitrogen atom to which they are bonded a 4 to 10-membered mono-, bi- or spirocyclic ring which, apart from the nitrogen atom, comprises 0 to 3 additional heteroatoms selected from the group of N, O and S, and may additionally be substituted by one or more of the following substituents: F, Cl, Br, CF$_3$, O—($C_1$-$C_8$)-alkyl, ($C_1$-$C_6$)-alkyl, CO(R64), oxo, OH, ($C_1$-$C_4$)-alkoxy-($C_1$-$C_4$)-alkyl, hydroxy-($C_1$-$C_4$)-alkyl, CON(R65)(R66), N(R67)CO(R68), N(R69)(R70), CO$_2$(R71), SO$_2$($C_1$-$C_6$)-alkyl;

R53 is preferably:
H, ($C_1$-$C_8$)-allyl, (C(R58)(R59))$_q$—R60, ($C_1$-$C_4$)-alkoxy-($C_1$-$C_4$)-alkyl, ($C_3$-$C_8$)-alkenyl, ($C_3$-$C_8$)-alkynyl, CO—($C_1$-$C_8$)-alkyl, CO—O($C_1$-$C_8$)-alkyl, CO(C(R61)(R62))$_r$N(R76)(R77);

R54 is preferably:
($C_1$-$C_8$)-alkyl, (C(R58)(R59))$_q$—R60, ($C_1$-$C_4$)-alkoxy-($C_1$-$C_4$)-alkyl, ($C_3$-$C_8$)-alkenyl, ($C_3$-$C_8$)-alkynyl;

or

R53 and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, oxo, CO(R64), CON(R65)(R66), hydroxy, COO(R71), N(R67)CO$(C_1-C_6)$-alkyl, N(R69)(R70) or $SO_2(C_1-C_6)$-alkyl;

R53, R54 are very particularly preferably:
$(C_1-C_8)$-alkyl, $(C(R58)(R59))_q$—R60, $(C_1-C_4)$-alkoxy-$(C_1-C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, oxo, CO(R64), hydroxy, N(R67)CO$(C_1-C_6)$-alkyl, or $SO_2(C_1-C_6)$-alkyl;

R58, R59
independently of one another H, $(C_1-C_6)$-alkyl, OH;

R57, R61, R62, R64, R65, R66, R67, R68, R69, R70, R71
independently of one another H, $(C_1-C_6)$-alkyl;

or
R69 and R70
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

q, r independently of one another 0, 1, 2, 3, 4, 5, 6;

R60, R63
independently of one another OH, F, $O—(C_1-C_6)$-alkyl, CN, COO(R78), N(R74)CO$(C_1-C_6)$-alkyl, N(R76)(R77), CON(R72)(R73), $SO_2(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, $O—(C_1-C_6)$-alkyl, $(C_1-C_4)$-alkoxy-$(C_1-C_4)$-alkyl, $S—(C_1-C_6)$-alkyl, $(C_1-C_6)$-alkyl, $(C_2-C_6)$-alkenyl, $(C_3-C_8)$-cycloalkyl, $O—(C_3-C_8)$-cycloalkyl, $(C_3-C_8)$-cycloalkenyl, $O—(C_3-C_8)$-cycloalkenyl, $(C_2-C_6)$-alkynyl, N(R76)(R77), COO(R78), $SO_2(C_1-C_6)$-alkyl and COOH;
preferably OH, F, $O—(C_1-C_6)$-alkyl, N(R74)CO$(C_1-C_6)$-alkyl, $SO_2(C_1-C_6)$-alkyl, 3-12 membered mono-, bi- or spirocyclic ring which may comprise one to three heteroatoms from the group of N, O and S, and the 3-12 membered ring may comprise further substituents such as F, Cl, Br, OH, $CF_3$, $NO_2$, CN, $OCF_3$, oxo, $O—(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, N(R76)(R77) and $SO_2(C_1-C_6)$-alkyl;

R72, R73, R74, R76, R77, R78
independently of one another H, $(C_1-C_8)$-alkyl;
or
R72 and R73, R76 and R77
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur.

The radicals and groups R2 and B in the compounds of the general formula Ia particularly preferably have the following meanings:

R2 is H, F, Cl, Br, $O—(C_1-C_6)$-alkyl, preferably H, F, Cl, $(C_1-C_6)$-alkyl; particularly preferably H;
and
B H, N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic nonaromatic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43), $SO_2CH_3$, $SCF_3$ or $S—(C_1-C_6)$-alkyl; or where the ring system may be linked to A by =C(R43');

preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic nonaromatic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$; or where the ring system may be linked to A by =C(R43');

particularly preferably Hydroxy-$(C_1-C_4)$-alkyl, $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, oxo, oxo, CO(R37), hydroxy, N(R41)CO$(C_1-C_6)$-alkyl or $SO_2CH_3$;

very particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl, N(R42)(R43) or $SO_2CH_3$;

in particular preferably hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, 3-6 membered nonaromatic monocyclic ring selected from the group:

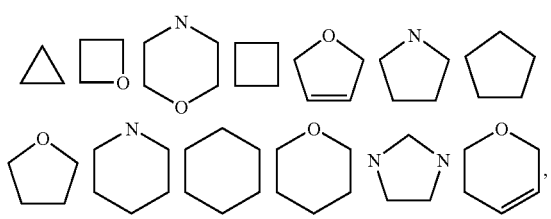

where the ring system may additionally be substituted by methyl, ethyl, OH, Oxo;

R35, R36, R37, R38, R39, R40, R41, R42, R43, R43'
independently of one another H, $(C_1-C_8)$-alkyl;

or

R38 and R39, R42 and R43
form independently of one another optionally together with the nitrogen atom to which they are bonded a 5-6 membered ring which, apart from the nitrogen atom, may also comprise 0-1 further heteroatoms from the group of NH, N—($C_1$-$C_6$)-alkyl, oxygen and sulfur; where R35, R36, R37, R38, R39, R40, R41, R42, R43, R43'
are preferably independently of one another H, ($C_1$-$C_8$)-alkyl;

where the further radicals and groups in the compound of the formula Ia have the aforementioned meanings.

The compounds of the invention of the general formula I can be prepared in analogy to processes known to the skilled worker. Suitable processes for preparing the compounds of the invention of the general formula I are mentioned by way of example below (see in particular methods A, B, C, D, E, F, G, H, I, J, K, L, M, N, O, P, Q, R, S, T, U, V, W, X, Y, Z, AA, BA, and schemes 1 to 10).

A reaction sequence for preparing the compounds of the invention of the general formula I, where R27 is H, includes the following steps:
resulting in the compounds of the formula I:
i) reaction of an aromatic ortho-amino carboxylic ester of the general formula (II) with dimethylformamide dimethyl acetal to give the corresponding aminal of the general formula (III):

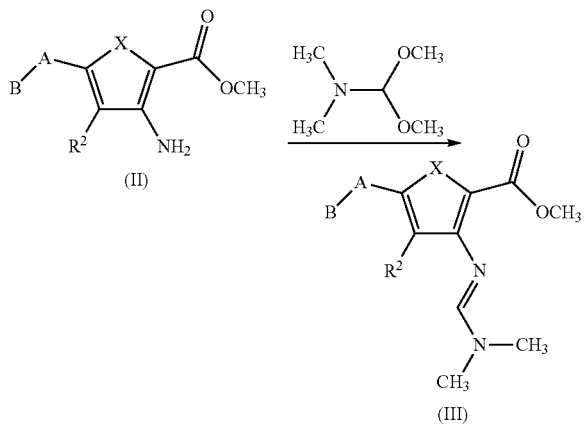

ii) reaction of the resulting animal (III) with a substituted primary aromatic amine to give a fused pyrimidinone, and
iii) where appropriate further reaction,
resulting in compounds of the formula I:

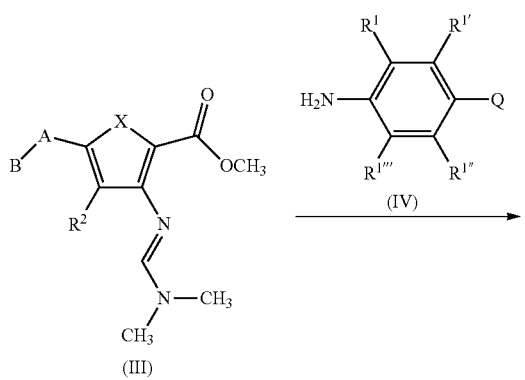

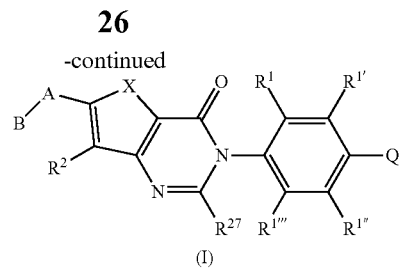

The symbols used in the compounds of the formulae II, III and IV have the meanings mentioned above in relation to the general formula I.

Depending on the substitution pattern of the compounds of the general formula I, the desired compounds are obtained directly after the reaction in step ii), or a further reaction (step iii)) is necessary where appropriate in order to obtain the desired compounds of the general formula I. Suitable reaction conditions for carrying out the individual steps of the aforementioned process are known to the skilled worker.

Preferred embodiments of said steps, as well as the preparation of the starting substances employed in the steps, are known to the skilled worker below and mentioned by way of example in said schemes and methods, and examples.

This invention further relates to the use of compounds of the formula I and their pharmaceutical compositions as MCH receptor ligands. The MCH receptor ligands of the invention are particularly suitable as modulators of the activity of the MCH1R.

The role of MCH in regulating the energy balance has now been well documented (Qu, D. et al. Nature 1996, 380, 243-7; Shimada, M. et al. Nature 1998, 396, 670-4; Chen, Y et al. Endocrinology 2002, 143, 2469-77; Endocrinology 2003, 144, 4831-40; Review: G. Hervieu, Expert Opin. Ther. Targets 2003, 7, 495-511; Shi, Y., Peptides 2004, 25, 1605-11).

There are also indications that MCH antagonists can have a beneficial influence on centrally related disorders such as, for example, anxiety states, depressions (Borowsky, B. et al. Nature Medicine 2002, 8, 825-30; Review: G. Hervieu, Expert Opin. Ther. Targets 2003, 7, 495-511; Chaki, S. et al., Drug Dev. Res. 2005, 65, 278-290; Dyck, B., Drug Dev. Res. 2005, 65, 291-300).

Compounds of this type are particularly suitable for the treatment and/or prevention of
1. Obesity
2. Diabetes mellitus, especially type 2 diabetes, including the prevention of the sequelae associated therewith.
    Particular aspects in this connection are
    hyperglycemia,
    improvement in insulin resistance,
    improvement in glucose tolerance,
    protection of the pancreatic β cells
    prevention of macro- and microvascular disorders
3. Dyslipidemias and the sequelae thereof such as, for example, atherosclerosis, coronary heart disease, cerebrovascular disorders etc, especially those (but not restricted thereto) which are characterized by one or more of the following factors:
    high plasma triglyceride concentrations, high postprandial plasma triglyceride concentrations
    low HDL cholesterol concentration
4. Various other conditions which may be associated with the metabolic syndrome, such as:
    thromboses, hypercoagulable and prothrombotic stages (arterial and venous)
    high blood pressure heart failure such as, for example (but not restricted thereto), following myocardial infarction, hypertensive heart disease or cardiomyopathy 5. Psychiatric indications such as
   depressions
   anxiety states
   disturbances of the circadian rhythm
   affection disorders
   schizophrenia
   addictive disorders Formulations The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of body weight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contains a defined amount of at least one compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain at least one compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of at least one compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing at least one compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished as selective MCH1R antagonists by their low toxicity, the small effect on metabolizing enzymes and their few side effects. In particular, preferred compounds of the invention are notable for low blockade of the HERG channel. In addition, preferred compounds of the formula I are noticeably soluble in aqueous systems and thus particularly suitable for pharmaceutical development. The pharmacological effect is moreover achieved in in vivo test models after oral administration from well-tolerated vehicles.

The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with Other Medicaments

The compounds of the invention can be administered alone or in combination with one or more further pharmacologically active substances which have, for example, beneficial effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes
11. active ingredients for the treatment of neurodegenerative conditions
12. active ingredients for the treatment of diseases of the central nervous system
13. active ingredients for the treatment of medicament-, nicotine- or alcohol addiction
14. pain killers They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples of active ingredients suitable for combination products are listed below:

All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or Apidra® (HMR 1964) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives such as, for example, exenatide, liraglutide or those which have been disclosed in WO98/08871 or WO2005027978 of Novo Nordisk A/S, in WO01/04156 of Zealand or in WO00/34331 of Beaufour-Ipsen, Pramlintide Acetate (Symlin; Amylin Pharmaceuticals), and orally effective hypoglycemic active ingredients.

The active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase
modulators of glucose transporter 4 (GLUT4),
inhibitors of glutamine-fructose-6-phosphate amidotransferase (GFAT),
GLP-1 agonists, potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, at least one compound of the formula I is administered in combination with an HMGCoA reductase inhibitor such as simvastatin, fluvastatin, pravastatin, lovastatin, atorvastatin, cerivastatin, rosuvastatin or L-659699

In one embodiment of the invention, at least one compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, at least one compound of the formula I is administered in combination with a PPAR gamma agonist such as, for example, rosiglitazone, pioglitazone, JTT-501, GI 262570, R-483 or CS-011 (rivoglitazone).

In one embodiment of the invention, at least one compound of the formula I is administered in combination with a PPAR alpha agonist such as, for example, GW9578, GW-590735, K-111, LY-674, KRP-101 or DRF-10945.

In one embodiment of the invention, at least one compound of the formula I is administered in combination with a mixed PPAR alpha/gamma agonist such as, for example, muraglitazar, tesaglitazar, naveglitazar, LY-510929, ONO-5129, E-3030 or as described in WO00/64888, WO00/64876, WO03/020269, WO2004075891, WO2004076402, WO2004075815, WO2004076447, WO2004076428, WO2004076401, WO2004076426, WO2004076427, WO2006018118, WO2006018115, und WO2006018116 or in J. P. Berger et al., TRENDS in Pharmacological Sciences 28(5), 244-251, 2005.

In one embodiment of the invention, at least one compound of the formula I is administered in combination with a PPAR delta agonist such as, for example, GW-501516 or as described in WO2005097762, WO2005097786, WO2005097763, und WO2006029699.

In one embodiment, at least one compound of the formula I is administered in combination with metaglidasen or with MBX-2044 or other partial PPAR gamma agonists/antagonists.

In one embodiment of the invention, at least one compound of the formula I is administered in combination with a fibrate such as, for example, fenofibrate, clofibrate or bezafibrate.

In one embodiment of the invention, at least one compound of the formula I is administered in combination with an MTP inhibitor such as, for example, implitapide, BMS-201038, R-103757 or those described in WO2005085226.

In one embodiment of the invention, at least one compound of the formula I is administered in combination with a CETP inhibitor such as, for example, torcetrapib or JTT-705.

In one embodiment of the invention, at least one compound of the formula I is administered in combination with a bile acid absorption inhibitor (see, for example, U.S. Pat. No. 6,245,744, U.S. Pat. No. 6,221,897 or WO00/61568), such as, for example, HMR 1741 or those as described in DE 10 2005 033099.1 and DE 10 2005 033100.9.

In one embodiment of the invention, at least one compound of the formula I is administered in combination with a polymeric bile acid adsorbent such as, for example, cholestyramine or colesevelam.

In one embodiment of the invention, at least one compound of the formula I is administered in combination with an LDL receptor inducer (see U.S. Pat. No. 6,342,512), such as, for example, HMR1171, HMR1586 or those as described in WO2005097738.

In one embodiment, at least one compound of the formula I is administered in combination with Omacor® (omega-3 fatty acids; highly concentrated ethyl esters of eicosapentaenoic acid and of docosahexaenoic acid).

In one embodiment of the invention, at least one compound of the formula I is administered in combination with an ACAT inhibitor such as, for example, avasimibe.

In one embodiment of the invention, at least one compound of the formula I is administered in combination with an antioxidant such as, for example, OPC-14117, probucol, tocopherol, ascorbic acid, β-carotene or selenium.

In one embodiment of the invention, at least one compound of the formula I is administered in combination with a vitamin such as, for example, vitamin B6 or vitamin B12.

In one embodiment of the invention, at least one compound of the formula I is administered in combination with a lipoprotein lipase modulator such as, for example, ibrolipim (NO-1886).

In one embodiment of the invention, at least one compound of the formula I is administered in combination with an ATP citrate lyase inhibitor such as, for example, SB-204990.

In one embodiment of the invention, at least one compound of the formula I is administered in combination with a squalene synthetase inhibitor such as, for example, BMS-188494 or as described in WO2005077907.

In one embodiment of the invention, at least one compound of the formula I is administered in combination with a lipoprotein(a) antagonist such as, for example, gemcabene (CI-1027).

In one embodiment of the invention, at least one compound of the formula I is administered in combination with an HM74A receptor agonist such as, for example, nicotinic acid.

In one embodiment of the invention, at least one compound of the formula I is administered in combination with a lipase inhibitor such as, for example, orlistat or cetilistat (ATL-962).

In one embodiment, at least one compound of the formula I is administered in combination with insulin.

In one embodiment, at least one compound of the formula I is administered in combination with a sulfonylurea such as, for example, tolbutamide, glibenclamide, glipizide or glimepiride.

In one embodiment, at least one compound of the formula I is administered in combination with a biguanide such as, for example, metformin.

In another embodiment, at least one compound of the formula I is administered in combination with a meglitinide such as, for example, repaglinide or nateglinide.

In one embodiment, at least one compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, at least one compound of the formula I is administered in combination with an α-glucosidase inhibitor such as, for example, miglitol or acarbose.

In one embodiment, at least one compound of the formula I is administered in combination with an active ingredient which acts on the ATP-dependent potassium channel of the beta cells, such as, for example, tolbutamide, glibenclamide, glipizide, glimepiride or repaglinide.

In one embodiment, at least one compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, at least one compound of the formula I is administered in combination with substances which influence hepatic glucose production, such as, for example an inhibitor of glycogen phosphorylase, such as, for example, PSN-357 or FR-258900 or those as described in WO2003084922, WO2004007455, WO2005073229-31 or WO2005067932.

In one embodiment, at least one compound of the formula I is administered in combination with glucagon receptor antagonists such as, for example, A-770077, NNC-25-2504 or as described in WO2004100875 or WO2005065680.

In one embodiment, at least one compound of the formula I is administered in combination with activators of glucokinase, such as, for example, RO-4389620, LY-2121260 (WO2004063179), PSN-105, PSN-1110, GKA-50 or such as described in WO2004072031, WO2004072066, WO 05103021, WO 06016178, WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 04,067,939, WO 04052869, EP 1532980, WO 03055482, WO 04002481, WO 05049019, WO 05066145, WO 05123132, WO 03080585, WO03097824, WO 04081001, WO 05063738, WO 05090332, WO 04063194, WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment, at least one compound of the formula I is administered in combination with an inhibitor of gluconeogenesis, such as, for example, FR-225654.

In one embodiment, at least one compound of the formula I is administered in combination with inhibitors of fructose-1,6-bisphosphatase (FBPase), such as, for example, CS-917.

In one embodiment, at least one compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, at least one compound of the formula I is administered in combination with inhibitors of glutamine-fructose-6-phosphate amidotransferase (GFAT), as are described for example in WO2004101528.

In one embodiment, at least one compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964× or as are described in WO2003074500, WO2003106456, WO200450658, WO2005058901, WO2005012312, WO2005012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, at least one compound of the formula I is administered in combination with inhibitors of 11-beta-hydroxysteroid dehydrogenase 1 (11β-HSD1), such as, for example, BVT-2733 or those as are described for example in WO200190090-94, WO200343999, WO2004112782, WO200344000, WO200344009, WO2004112779, WO2004113310, WO2004103980, WO2004112784, WO 2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment, at least one compound of the formula I is administered in combination with inhibitors of protein tyrosine phosphatase 1B (PTP1B), as are described for example in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment, at least one compound of the formula I is administered in combination with modulators of the sodium-dependent glucose transporter 1 or 2 (SGLT1, SGLT2), such as, for example, KGA-2727, T-1095, SGL-0010, AVE 2268 and SAR 7226 or as are described for example in WO2004007517, WO200452903, WO200452902, WO2005121161, PCT/EP2005/005959, WO2005085237, JP2004359630 or by A. L. Handlon in Expert Opin. Ther. Patents (2005) 15(11), 1531-1540.

In one embodiment, at least one compound of the formula I is administered in combination with modulators of GPR40.

In one embodiment, at least one compound of the formula I is administered in combination with inhibitors of hormone-sensitive lipase (HSL) as described for example in WO01/17981, WO01/66531, WO2004035550, WO2005073199 or WO03/051842.

In one embodiment, at least one compound of the formula I is administered in combination with inhibitors of acetyl-CoA carboxylase (ACC), such as, for example, those as described in WO199946262, WO200372197, WO2003072197 or WO2005044814.

In one embodiment, at least one compound of the formula I is administered in combination with an inhibitor of phosphoenolpyruvate carboxykinase (PEPCK), such as, for example, those as described in WO2004074288.

In one embodiment, at least one compound of the formula I is administered in combination with an inhibitor of glycogen synthase kinase 3 beta (GSK-3 beta), as described for example in US2005222220, WO2005085230, WO2005111018, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, at least one compound of the formula I is administered in combination with an inhibitor of protein kinase C beta (PKC beta), such as, for example, ruboxistaurin.

In one embodiment, at least one compound of the formula I is administered in combination with an endothelin A receptor antagonist such as, for example, avosentan (SPP-301).

In one embodiment, at least one compound of the formula I is administered in combination with inhibitors of "I-kappaB kinase" (IKK inhibitors), as are described for example in WO2001000610, WO2001030774, WO2004022553 or WO2005097129.

In one embodiment, at least one compound of the formula I is administered in combination with modulators of the glucocorticoid receptor, like those described for example in WO2005090336.

In a further embodiment, at least one compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-amino-quinazolin-2-ylamino)methyl] cyclohexylmethyl}amide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

cannabinoid receptor 1 antagonists (such as, for example, rimonabant, SR147778 or those as are described for example in EP 0656354, WO 00/15609, WO02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897);

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO2005009184, WO2005000339, EP1460069, WO2005047253, WO2005047251, EP1538159, WO2004072076 or WO2004072077;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403 or WO2005075458);

histamine H3 receptor agonists (e.g. ABT-834, ABT-239, 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893, FR2870846WO2005037810, Celanire, S., et al. Drug Discovery Today 2005, 10, 1613-1627);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NGD-4715, AMG-076, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, eg. 1-(3-ethylbenzofuran-7-yl)piperazine oxalic acid salt (WO 01/09111);

5-HT2C receptor agonists (such as, for example, APD-356, BVT-933 or those as are described in WO200077010, WO20077001-02, WO2005019180, WO2003064423, WO200242304 or WO2005082859);

5-HT6 receptor antagonists as are described for example in WO2005058858;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO2004094618, WO200058491, WO2005044250, WO2005072740, JP2005206492 or WO2005013907;

inhibitors of fatty acid synthase (FAS) such as, for example, C75 or those as described in WO2004005277;

oxyntomodulin;

oleoyl-estrone;

or thyroid hormone receptor agonists such as, for example: KB-2115 or those as described in WO20058279, WO200172692, WO200194293, WO2003084915, WO2004018421 or WO2005092316.

In one embodiment, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexanphetamine or amphetamrine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, at least one compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main. Combination with Caromax® is possible in one preparation or by separate administration of compounds of the formula I and Caromax®. Caromax® can in this connection also be administered in the form of food products such as, for example, in bakery products or muesli bars.

In one embodiment, at least one compound of the formula I is administered in combination with PDE (Phosphodiesterase) inhibitors such as, for example, described in WO2003/077949 or WO2005012485.

In one embodiment, at least one compound of the formula I is administered in combination with NAR-1 (Nicotinic acid receptor) agonists such as for example described in WO2004094429.

In one embodiment, at least one compound of the formula I is administered in combination with CB2 (Cannabinoid receptor 2) agonists such as for example described in US2005/143448.

In one embodiment, at least one compound of the formula I is administered in combination with H1 (Histamine receptor 1) agonists such as for example described in WO2005101979.

In one embodiment, at least one compound of the formula I is administered in combination with Bupropion, such as for example described in WO2006017504.

In one embodiment, at least one compound of the formula I is administered in combination with Opiate receptor-antagonists such as for example described in WO2005107806 or WO2004094429.

In one embodiment, at least one compound of the formula I is administered in combination with inhibitors of the neutral Endopeptidase such as for example described in WO200202513, WO2002/06492, WO 2002040008, WO2002040022 or WO2002047670.

In one embodiment, at least one compound of the formula I is administered in combination with NPY (Neuropeptide Y) modulators such as for example described in WO2002047670.

In one embodiment, at least one compound of the formula I is administered in combination with a inhibitor of the sodium/hydrogen replacement protein such as described for example in WO2003092694.

In one embodiment, at least one compound of the formula I is administered in combination with modulators of the glucocorticoid receptor such as for example described in WO2005090336.

In one embodiment, at least one compound of the formula I is administered in combination with nicotine receptor-agonists such as for example described in WO2004094429.

In one embodiment, at least one compound of the formula I is administered in combination with NRIs (Norepinephrine reuptake inhibitor) such as for example described in WO2002053140.

In one embodiment, at least one compound of the formula I is administered in combination with MOA (E-beta-Methoxyacrylate), such as for example segeline, or such as for example described in WO2002053140.

In one embodiment, at least one compound of the formula I is administered in combination with an antithrombotic active ingredient such as for example Clopidogrel.

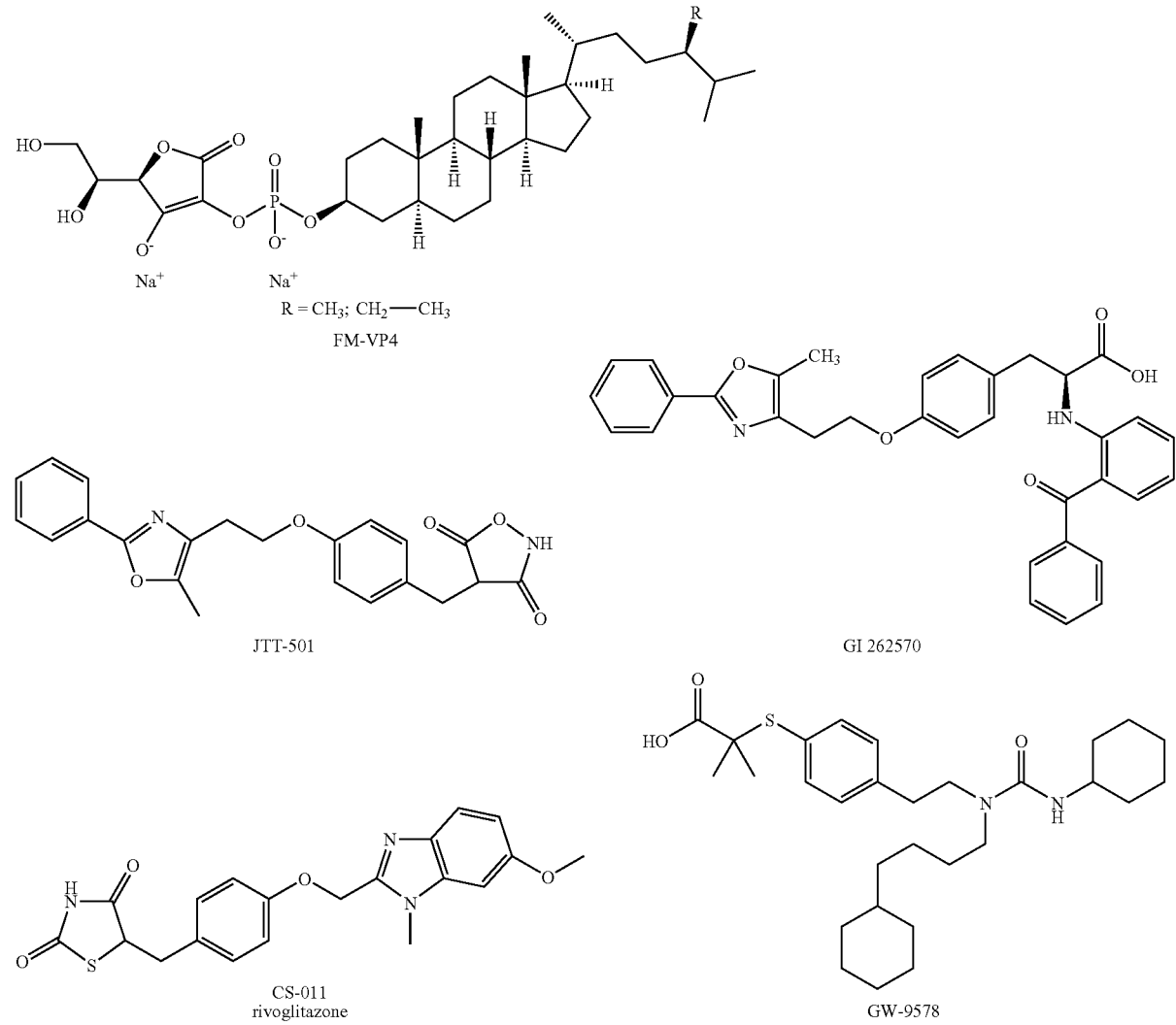

-continued
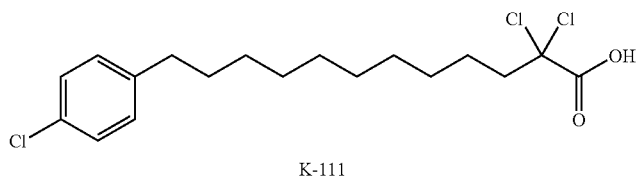
K-111
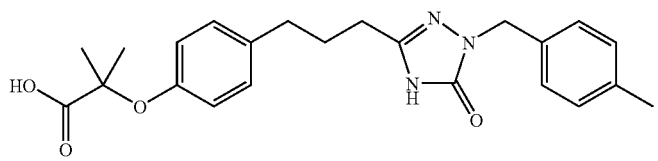
LY-674
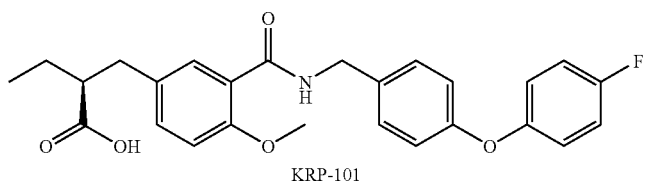
KRP-101
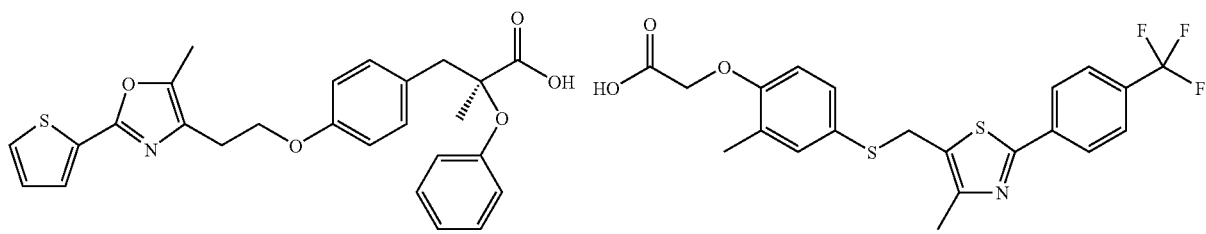
LY-510929
GW-501516
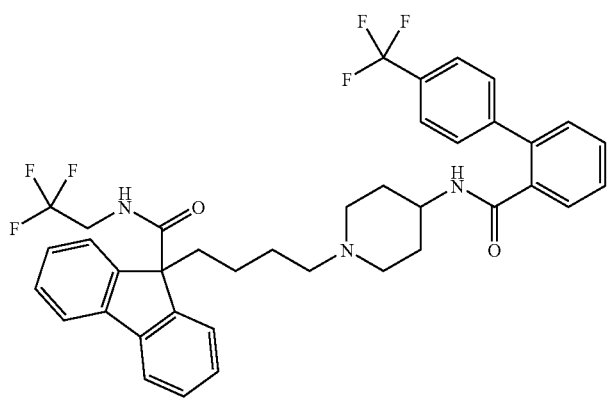
BMS-201038

-continued
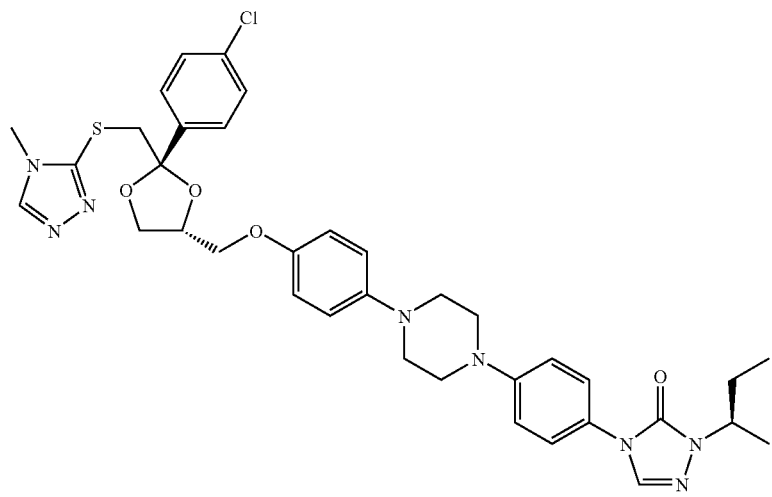
R-103757
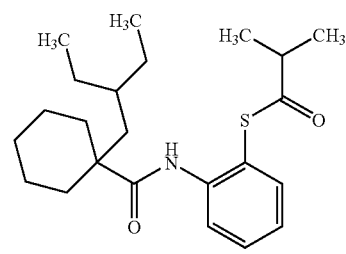
JTT-705
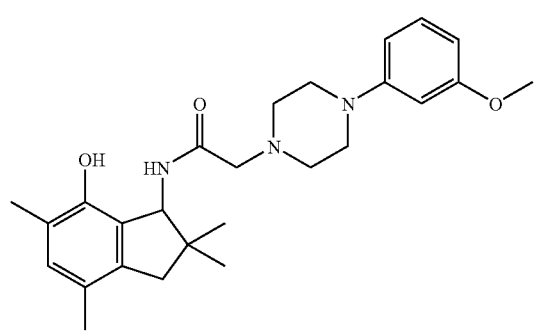
OPC-14117
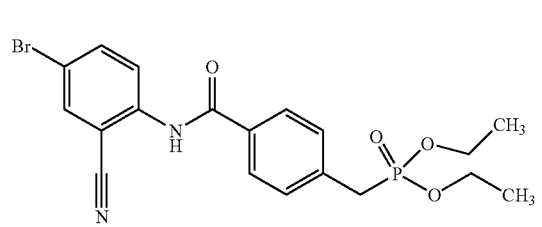
NO-1886
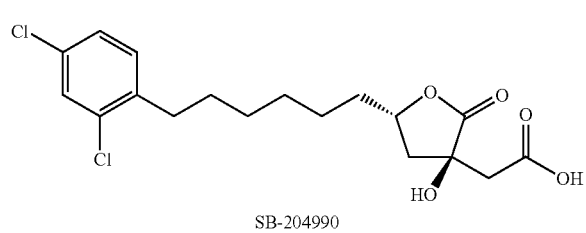
SB-204990
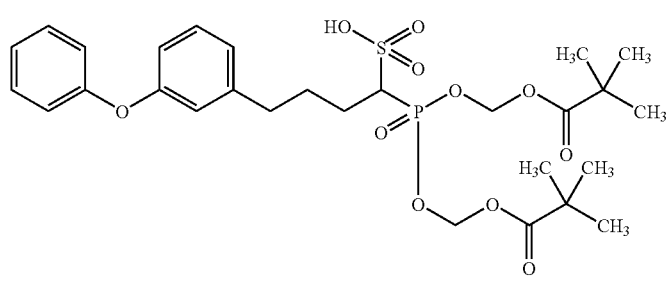
BMS-188494
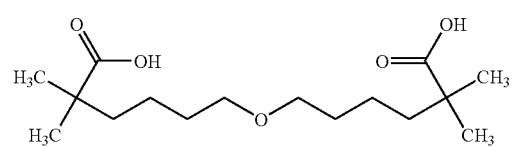
CI-1027
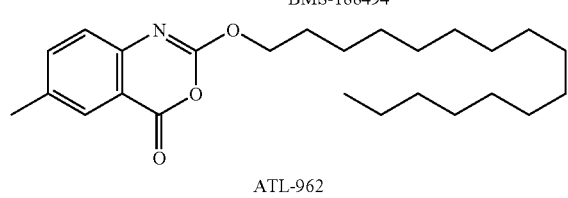
ATL-962

-continued
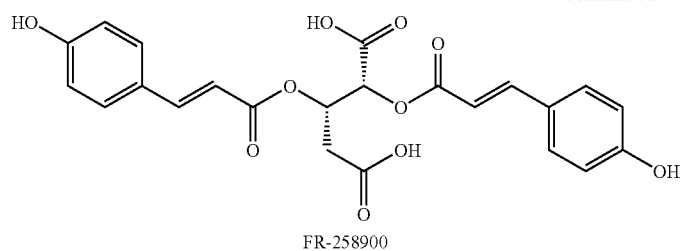
FR-258900
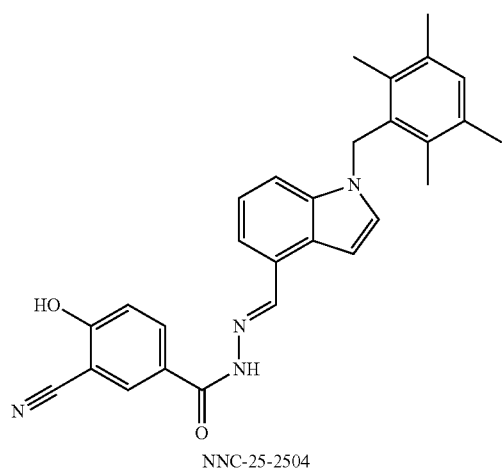
NNC-25-2504
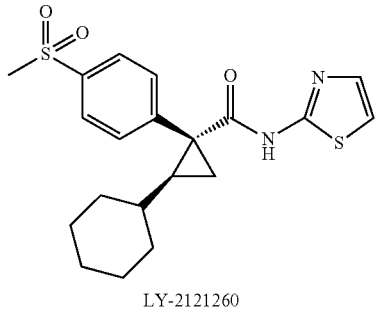
LY-2121260
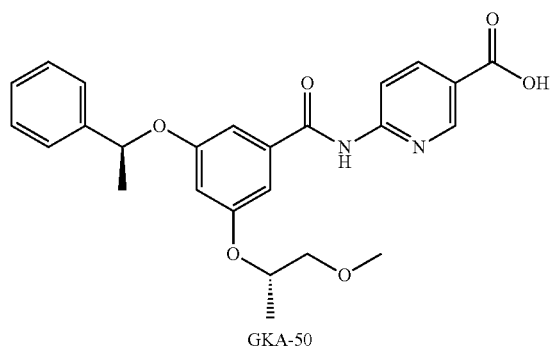
GKA-50
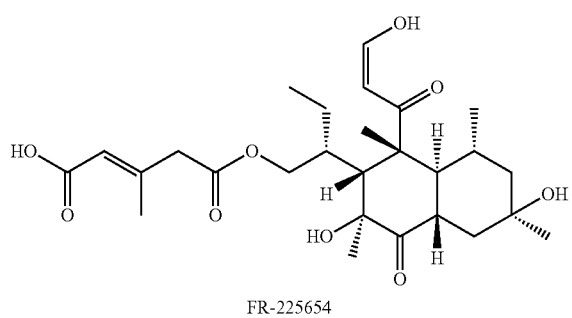
FR-225654
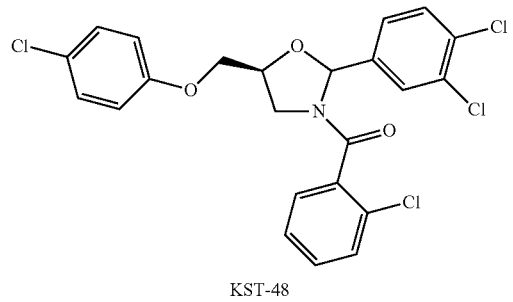
KST-48
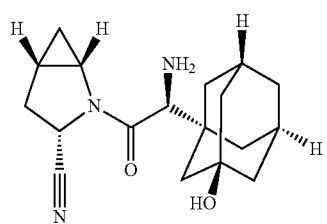
BMS-477118
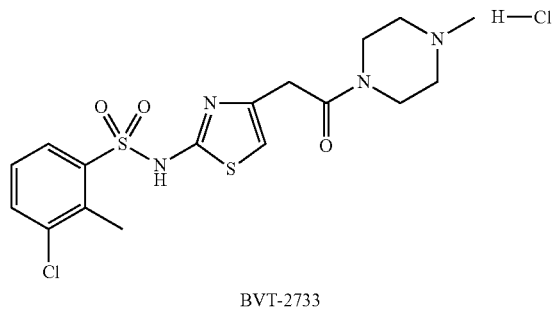
BVT-2733
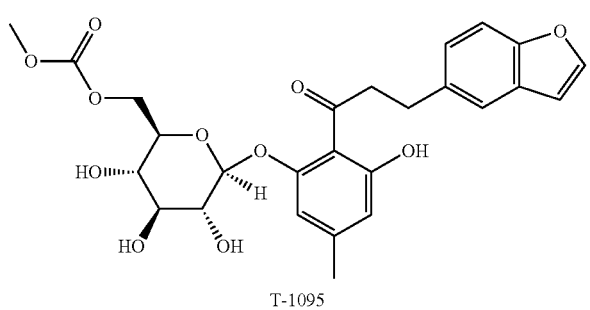
T-1095

-continued
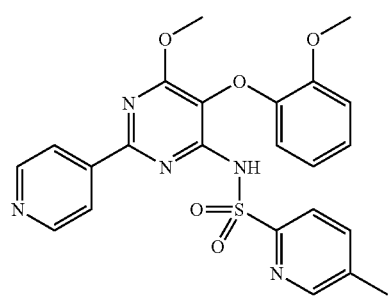
SPP-301
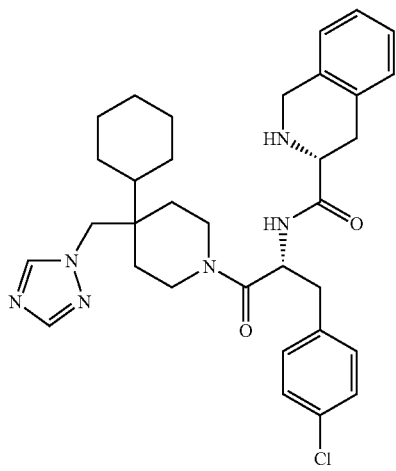
THIQ
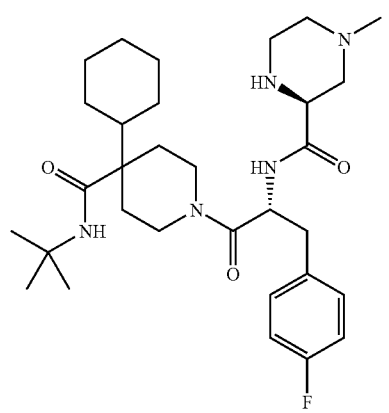
MB243
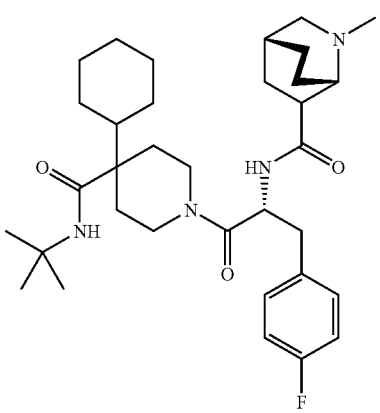
RY764
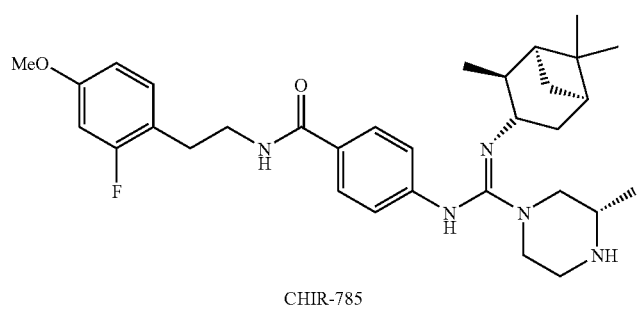
CHIR-785
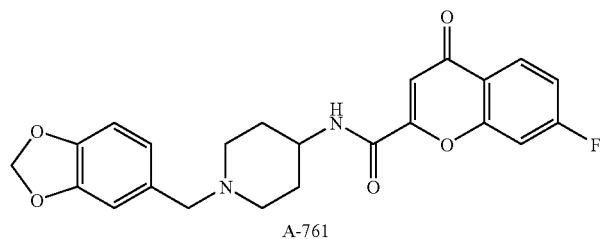
A-761

-continued
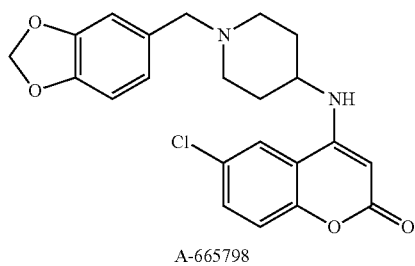
A-665798
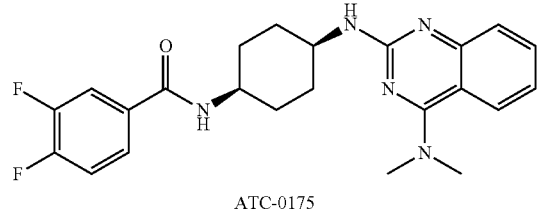
ATC-0175
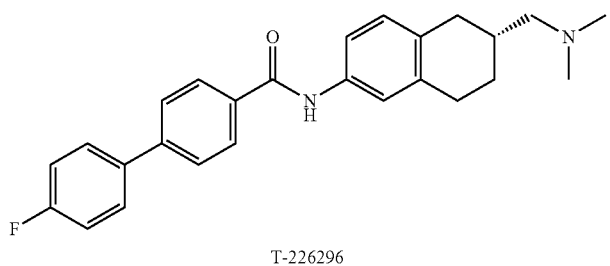
T-226296
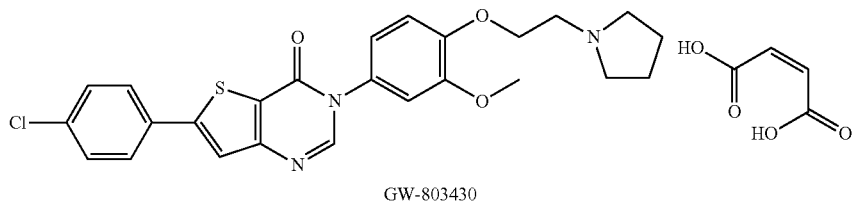
GW-803430
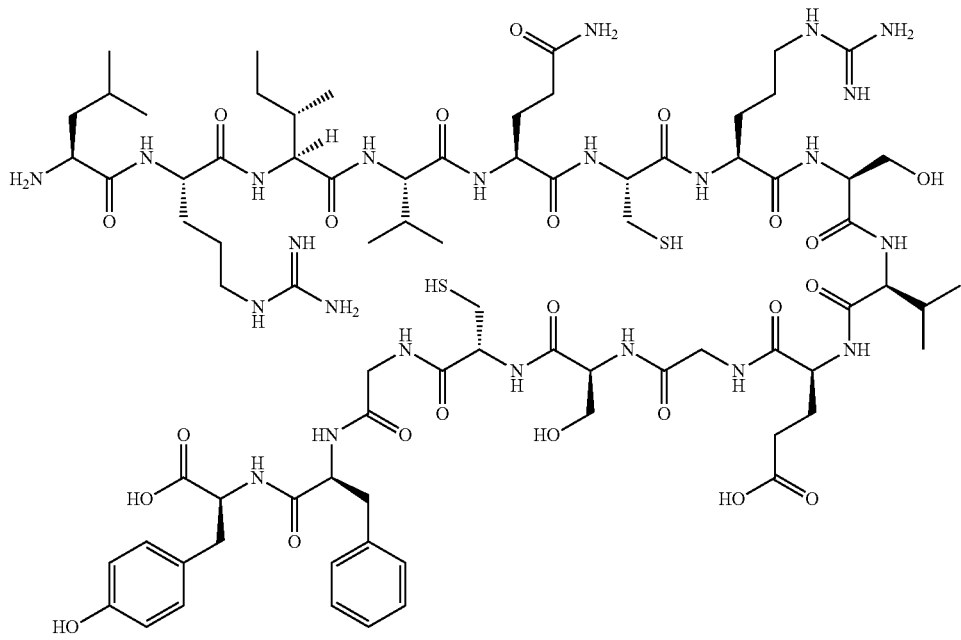
AOD-9604

-continued

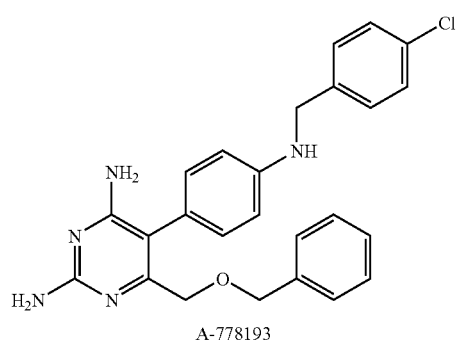

A-778193

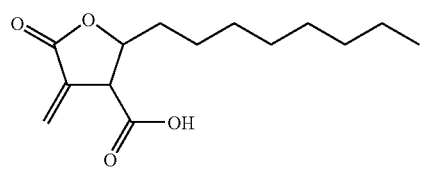

C75

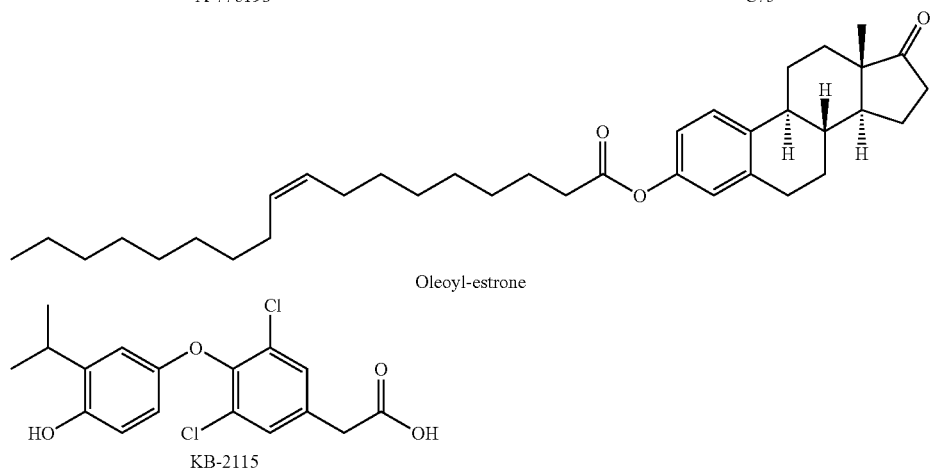

Oleoyl-estrone

KB-2115

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

Pharmacological Testing

Test Models

Suitability of the compounds of the invention as active pharmaceutical ingredient can be tested by means of various test models. Descriptions are given of such test models by way of example below.

Influence on the MCH receptor in vitro; determination of functional IC50 values of MCH1R antagonists Cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13554-13562, 2001). A difference from the reference was, however, the use of the plasmid pEAK8 from EDGE Biosystems (JSA) for the construction of the expression vector. The host used for the transfection was a transformed HEK cell line named "PEAK Stable Cells" (likewise from EDGE Biosystems). Functional measurements of the cellular calcium flux after addition of agonist (MCH) in the presence of ligand of the invention took place with the aid of the FLIPR apparatus from Molecular Devices (USA), using protocols of the apparatus manufacturer. The compounds of the invention show a significant inhibition (>30%) of the signal induced by the agonist at a concentration of 100 µM, preferably at 10 µM, particularly preferably at 1 µM, very particularly preferably at 100 nM and even more particularly preferably at 10 nM.

Besides the functional activity it is also possible to determine the affinity for the MCH1R according to Audinot et al. (Br. J. Pharmacol. 2001, 133, 371-378). Preferred compounds of the invention show an IC50 of less than 1 µM, particularly preferably of less than 100 nM, very particularly preferably of less than 10 nM and even more particularly preferably of less than 1 nM.

Milk Intake by Female NMRI Mice

The anorectic effect is tested on female NMRI mice. After withdrawal of feed for 24 hours, the test substance is administered intraperitoneally or preferably orally by gavage. The animals are housed singly with free access to drinking water and, 30 minutes after administration of product, are offered condensed milk. The condensed milk consumption is determined every half hour for 7 hours, and the general condition of the animals is observed. The measured milk consumption is compared with the vehicle-treated control animals.

The vehicle itself has no influence on feed intake. Preferred tolerated vehicles for the administration are, for example, hydroxyethylcellulose (0.5% in water) or Solutol HS15 (5% in hydroxyethylcellulose (0.5% in water)).

Feed and Water Intake of Female Wistar Rats

As alternative to testing the anorectic effect on NMRI mice, it is also possible analogously to use female Wistar rats weighing about 220-250 g. The animals are accustomed to the experimental environment before the start of the study. In one embodiment, the animals have free access to feed and water up to the start of the experiment. In another embodiment, access of the animals to feed is withdrawn 24 hours before the administration. For the investigation of the test substance, the animals are housed singly with free access to feed and water. Feed intake and water intake are measured continuously every 30 minutes over a period of 22 hours using a computer-assisted system (TSE Drinking & Feeding Monitor). The measured feed and water consumption is compared with the vehicle-treated control animals.

Body Weight Gain of Diet-Induced Obese and Standard-Fed Mice

For these investigations, male C57BL6J mice 5 weeks old (weaning age) are accustomed either to a standard maintenance diet or to a high-fat and thus high-energy diet. After 12 weeks, the normally fed, slim mice have typically reached a body weight of about 25 g, and the fat-fed mice have reached one of about 35 g. The animals are housed singly, and the feed intake and water intake are determined individually. There is free access to feed and water during the experiment.

The test substances are administered orally in a vehicle and always tested by comparison with the vehicle control which is included in parallel. The vehicle itself has no influence on the feed intake, and is normally hydroxyethylcellulose (0.5% in water) or Solutol HS15 (5% in hydroxyethylcellulose (0.5% in water)). A corresponding group of slim mice is kept for each group of diet-induced obese mice.

Feed consumption and water consumption are determined each day in the first week and then once per week by reweighing the offered feed and water, respectively. The body weight is measured each day.

Blood samples are taken before and at the end of the treatment in order to determine serum parameters which provide information about changes in intermediary metabolism. It is additionally possible to determine the body fat content on the living animal by means of an impedance measurement (TO-BEC method).

Micronucleus Test (In Vitro)

The aim of the micronucleus test (in vitro) is to examine whether a test compound has the potential to elicit the formation of micronuclei (small membrane-bound DNA fragments) in various cell lines or primary cultures, with or without metabolic activation by S9 liver homogenate. The test system allows differentiation between the clastogenic and aneugenic potential of a test compound by an immunochemical labeling of the kinetochores or by staining the DNA fragments by the FISH (fluorescence in situ hybridization) method.

Brief description: The cells are treated in a 96-well microtiter plate with the test compound. The treatment time is typically 3 hours with metabolic activation or 24 hours without metabolic activation. Twenty four hours after the end of the treatment, the cells are isolated, fixed and stained. The cytotoxicity of the test compound is assessed according to the relative cell growth expressed as percentage growth or taking account of the doubling time as population doubling compared with the negative control. The highest test concentration should show not less than 30% surviving cells, or should be the concentration at which a precipitate of the test compound is observed. Duplicate determinations should be carried out with each test concentration. An accurate detailed description of the experiment is to be found in Kirsch-Volders et al. (Mutation Res. 2003, 540, 153-163).

Evaluation: The structural or numerical chromosomal damage is reported as the increase in the number of cells with micronuclei in an ensemble of 1000 cells at three analyzable test concentrations. The test is regarded as positive in the following cases:

a) the increase in the number of cells with micronuclei is significant by comparison with the negative control (solvent or untreated), or b) the number of micronuclei is increased to a biologically relevant extent, concentration-dependently by comparison with the negative control.

A positive control must show a clear statistically significant effect by comparison with the negative control.

Preferred compounds of the invention are negative in the micronucleus test.

AMES II Test

The aim of the AMES II test is to examine whether a test compound has mutagenic potential.

Brief description: A mixed bacterial strain (mixed strains, 6 different *Salmonella typhimurium* strains with in each case a missence point mutation in the histidine operon) and the *Salmonella typhimurium* strain TA98 for detecting frame shift mutations is treated in a 384-well microtiter plate with various concentrations of the test substance with or without metabolic activation through addition of S9 liver homogenate (accurate descriptions of the experiment are to be found in the literature: P. Gee, D. M. Maron, B. N. Ames; Proc. Natl. Acad. Sci. USA 1994, 91, 11606 and Flückiger-Isler et al.; Mutation Res. 2004, 558, 181 and cit. lit.).

Mutagenic test compounds cause back-mutations and thus restore the functionality of endogenous histidine biosynthesis. Mutated bacteria are thus able to divide and expand to bacterial colonies.

Evaluation: If there is enhanced bacterial growth owing to mutations of the bacteria, then enzymes are digested in the growth medium. As a result, the pH in the medium falls and the color of the added indicator (bromocresol purple) changes from pale violet to yellow. The test is regarded as positive if the number of wells in which a color change is observed per concentration increases significantly by comparison with the control.

Preferred compounds of the invention are negative in the AMES II test.

Cytotoxicity Tests a) LDH Release

The aim of the test for LDH (lactate dehydrogenase) release is to examine whether a compound damages the integrity of the cell wall and may thus cause cell death.

Brief description: The LDH activity which enters the cell supernatant from the cytosol due to cell damage is measured by colorimetry. The cells are treated with the test compound. Fifty microliters of the culture supernatant are removed and mixed with the reaction solution (LDH kit, Roche, Mannheim) in accordance with the manufacturer's information. LDH catalyzes the conversion of lactate into pyruvate. During this, NAD+ is reduced to NADH/H+. The latter in turn reduces, under the influence of the added diaphorase, a likewise added yellow tetrazolium salt to the red formazan.

Evaluation: The formazan is quantified by measuring the absorption at 492 nM (e.g. with TECAN SPECTRAFluor Plus).

Preferred compounds of the invention show no significant increase in LDH activity at concentrations below 10 µM. Particularly preferred compounds show no increase below a concentration of 50 µM. Even further preferred compounds show no increase below a concentration of 250 µM.

b) Intracellular ATP Content

The aim of the test is to determine the total intracellular ATP content, which is a measure of the energy level and thus the vitality of a cell.

Brief description: 100 µL of cell culture medium are mixed in a well of a microtiter plate with 100 µL of the CellTiter-Glo reagent (following the manufacturer's instructions: Promega Technical Bulletin No. 228, CellTiter-Glo Luminescent Cell Viability Assay). The cultures are shaken at room temperature for 2 minutes and then incubated for 10 minutes until the luminescence signal has stabilized.

Evaluation: The luminescence is recorded, integrating over one second (e.g. with TECAN SPECTRAFluor Plus).

Preferred compounds of the invention show no significant reduction in the ATP levels at concentrations below 10 µM. Particularly preferred compounds show no reduction below a concentration of 50 µM. Even further preferred compounds show no reduction below a concentration of 250 µM.

c) Neutral Red Uptake

The aim of the test is to measure the uptake of neutral red (NR) into the lysosomes/endosomes and vacuoles of living cells, which is a quantitative measure of the number and vitality of the cells.

Brief description: The cells are washed with 150 µL of a preheated phosphate buffer solution (PBS) and incubated with 100 µL of the NR medium at 37° C. in a humidified atmosphere with 7.5% carbon dioxide for 3 hours. After the incubation, the NR medium is removed and the cells are washed with 150 µL of PBS. Removal of the PBS is followed by addition of exactly 150 µL of an ethanol/glacial acetic acid solution. After shaking for 10 minutes, the dye is extracted from the cells to give a homogeneous dye solution. An exact description of the test is to be found in the literature (E. Borenfreund, J. A. Puemer, Toxicol. Lett. 1985, 24(2-3), 119-124).

Evaluation: The absorption of the dye solution is determined at 540 nM using a microtiter plate reader as difference from the absorption of the ethanol/glacial acetic acid solution.

HERG Channel Blockade

The aim of the test is to determine the concentration range in which the test compound blocks the cardiac HERG channel. Blockade of the HERG channel, which is responsible for the lkr current in the human heart, is associated with potentially fatal arrhythmias.

For expression of the cDNA encoding the HERG channel it was cloned into the pcDNA3 vector (Invitrogen). Chinese hamster oocytes (CHO, American Type Culture Collection, Rockville, Md.) were transfected using lipofectamine (GIBCO/BRL, Grand Island, N.Y.) with the HERG cDNA and selected using G418 (GIBCO/BRL, Grand Island, N.Y.; 500 µg/mL). CHO cells with stable expression of the HERG channel were cultured on a HAM F-12 medium which was supplemented with 10% native bovine serum, 1× penicillin/streptomycin and 500 µg/mL G418 in an atmosphere of 95% air/5% carbon dioxide.

The cells selected for the patch clamp experiment are seeded on a plastic support 18-24 hours before the experiment. HERG channel currents are recorded at room temperature by the whole-cell variant of the patch clamp technique using an Axopatch 200B amplifier (Axon Instruments, Foster City, Calif.). The electrodes (3-6 megaohms resistance) are prepared from TW150F glass capillaries (World Precision Instruments, Sarasota, Fla.) and filled with the pipette solution (120 mM potassium aspartate, 20 mM KCl, 4 mM Na2ATP, 5 mM HEPES, 1 mM MgCl2; adjusted to pH 7.2 with KOH). The HERG channel currents are induced by a positive voltage pulse (20 mV) followed by a negative pulse (−40 mV) and are recorded for later analysis. As soon as the hERG channel current of the cell flushed with the control solution (130 mM NaCl, 5 mM KCl, 2.8 mM NaOAc, 1 mM MgCl2, 10 mM HEPES; 10 mM glucose, 1 mM CaCl2; adjusted to pH 7.4 with NaOH) is stable, the cell is perfused with the test compound dissolved in the above control solution (by dilution of a 10 or 100 mM DMSO solution of the test compound so that the DMSO content is no more than 0.1%). The current is followed continuously until no further changes occur. The same procedure is repeated with increasing concentrations of the test compound. The maximum amplitude of the hERG current is measured in picoAmperes (pA) for each concentration and for each cell. The maximum amplitude in pA for each concentration of the test compound is compared with that of the pure control solution in the same cell and calculated as % of the control value.

Evaluation: The test compound is tested at various concentrations in 3-5 CHO cells which express hERG channel. The IC50 is obtained by use of nonlinear least squares regression (GraphPAD Software, San Diego, Calif.).

General Selectivity

In order to minimize the risk of unwanted side effects, it is desirable to keep the nonselective effect on biologically important functional units (e.g. receptors, ion channels and enzymes; for lists, see, for example, Whitebread, S. et al.; Drug Discovery Today 2005, 10, 1421-33 and Rolland, C. et al.; J. Med. Chem. 2005, 48, 6563-6574) by an active pharmaceutical ingredient as small as possible. General selectivity tests in a large number of in vitro test systems can be carried out by various specialized services (e.g. Cerep, Panlabs).

The compounds of the invention of the formula I exhibit, as selective MCH1R antagonists, selectivity factors of at least 30, preferably of 100, more preferably of 300 and even more preferably of 1000 vis à vis the affinity to other proteins. Examples of such proteins are serotonin receptor subtypes (e.g. the 5-HT2a receptor), muscarine receptor subtypes (e.g. the M1 receptor), adrenergic receptor subtypes (e.g. AR alpha1a), sodium and calcium channels (e.g. the L-type calcium channel).

Solubility in Aqueous Systems

Adequate solubility of a substance in aqueous solvent systems is an important prerequisite for a (reproducible) pharmacological effect. Solubilities in aqueous systems can be determined by various methods. Suitable examples of solution precipitation methods ("kinetic solubility") and methods which investigate the dissolution of a solid sample until an equilibrium is set up ("thermodynamic solubility").

a) Kinetic Solubility

A DMSO solution of the test compound (2.5 mM; 0.5 µL) is pipetted into 200 µL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 µM using a nephelometer (e.g. Nephelostar Galaxy, BMG Labtech). The concentration of the test compound in the aqueous test solution is then raised to a theoretical 12.5 µM by adding further DMSO solution (2.5 mM; 0.5 µL), and the turbidity measurement is repeated. Further additions of DMSO solutions (1 µL, 2.5 mM; 0.5 µL, 10 mM; then 9×1 µL, 10 mM resulting in theoretical concentrations of 25 µM, 50 µM, 100 µM, 150 µM, 200 µM, 250 µM, 300 µM, 350 µM, 400 µM, 450 µM and 500 µM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values <6.25 µM, 6.25-500 µM and >500 µM.

Preferred compounds of the invention show a kinetic solubility in phosphate buffer (pH 7.4) of at least 12.5 µM; more preferably of at least 50 µM and even more preferably of at least 250 µM.

b) Thermodynamic Solubility

The integrated UV absorption from HPLC UV measurement of serial dilutions of the test compound in DMSO (500 µM, 100 µM, 50 µM, 10 µM and 1 µM) shows a linear correlation with the concentration in a calibration line. The test compound (500 µg) is shaken together with the aqueous test solution (250 µL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods.

Preferred compounds of the invention show a solubility in phosphate buffer (pH 7.4) of at least 12.5 µM; more preferably of at least 50 µM and even more preferably of at least 250 µM.

Permeability

The test for permeability is carried out in CACO-2/TC7 cells which have been cultured (DMEM/Glutamax I/Gibco with high glucose content, HEPES 25 mM, 1% NEAA, 10% FBS, 40 µg/mL gentamycin; 37° C. surrounding temperature; 95% humidity and 10% CO2 content) on Becton Dickinson filters (24-well, uncoated) for 21 days. The permeability is tested at a concentration of 20 µM for the test compound (1% DMSO in HBSS) with a pH gradient (apical: pH 6.5 and 0.5% BSA; basolateral: pH 7.4 and 5% BSA). Analysis takes place by means of LCMS/MS. Further descriptions of the test system and references for the experimental procedure are to be found in Balimane, P. V.; Drug Discovery Today 2005, 10(5), 335-343.

Inhibition of CYP Enzymes

The inhibition of CYP enzymes is determined on recombinant enzymes (obtained from Becton Dickinson) and fluorescent substrates (BD/Gentest) as recommended by the manufacturer (see Website http://www.bdbiosciences.com). Further descriptions of the test system and references for the experimental procedure are to be found in Zlokarnik, G.; Drug Discovery Today 2005, 10(21), 1443-1450.

Metabolic Stability

The metabolic stability is determined by incubating the test compound (5 µM) with microsomal liver fractions (1 mg/mL protein with 0.1% w/v BSA; 1 mM NADPH, 0.5% DMSO) at 37° C. Analysis at an incubation time of 0 and 20 minutes takes place by means of LCMS/S. Further descriptions of the test system and references for the experimental procedure are to be found in Plant, N.; Drug Discovery Today 2004, 9(7), 328-336 and Lau, Y. Y. et al.; Pharmaceutical Res. 2002, 19(11), 1606-1610.

EXAMPLES

The examples and preparation methods detailed below serve to illustrate the invention without, however, restricting it.

The compounds of the invention of the formula I can be prepared by means of reactions known in principle. For example, the compounds according to the following general reaction schemes were obtained.

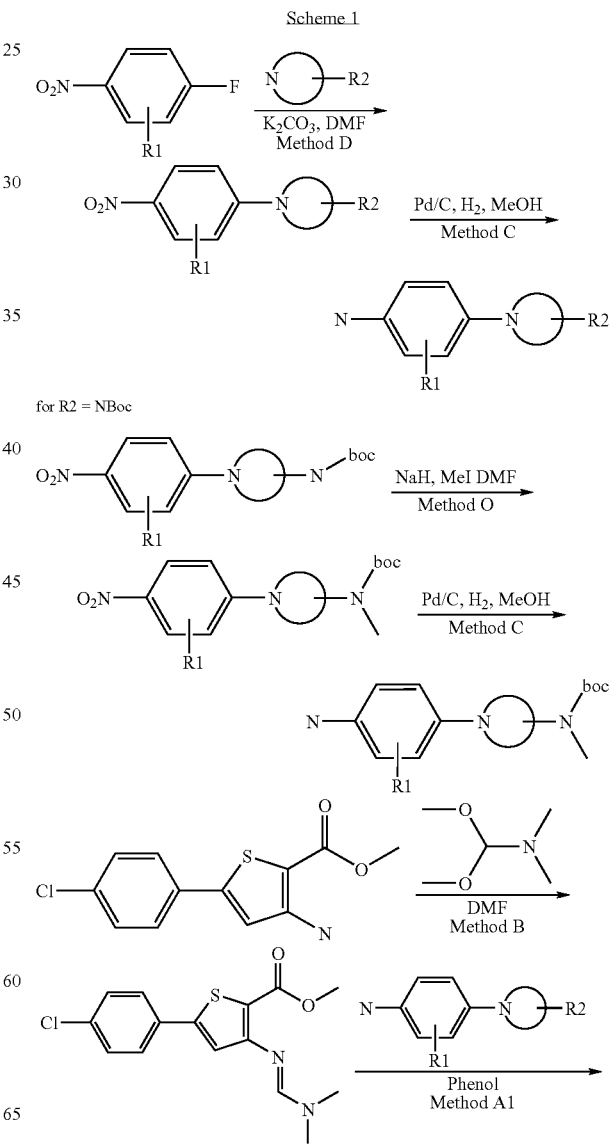

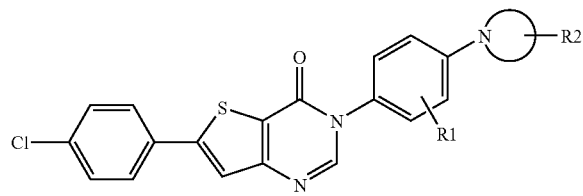
Other compounds of the invention can be obtained by further routes which are outlined by way of example in the following scheme.
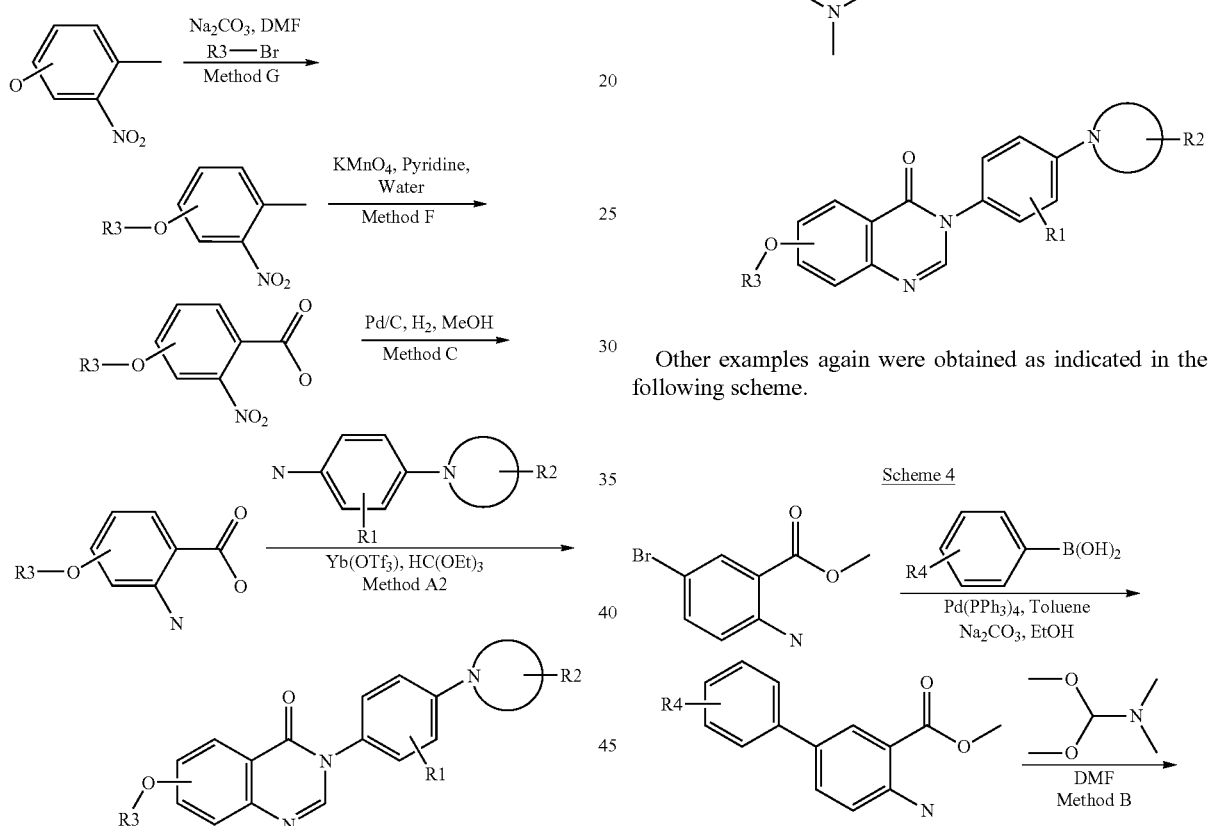
Other examples again were obtained as indicated in the following scheme.
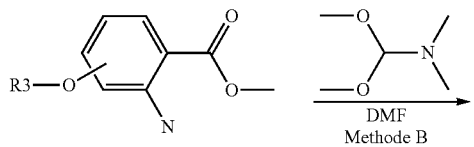
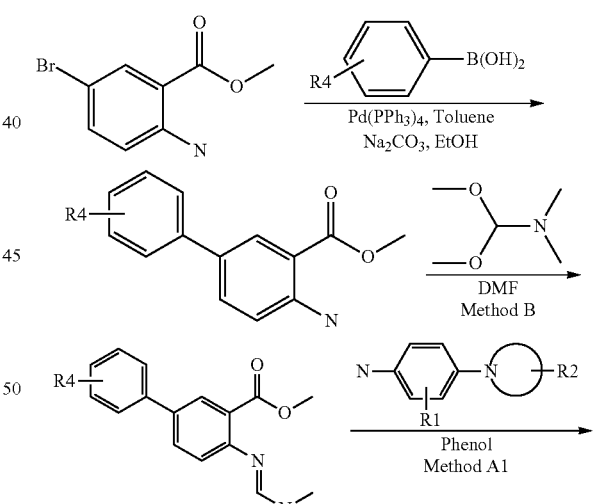
Other examples again were obtained as indicated in the following scheme.
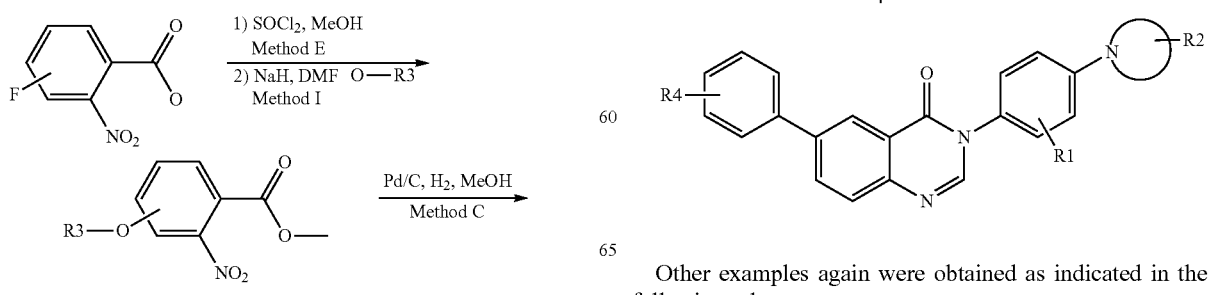
Other examples again were obtained as indicated in the following scheme.

Scheme 5
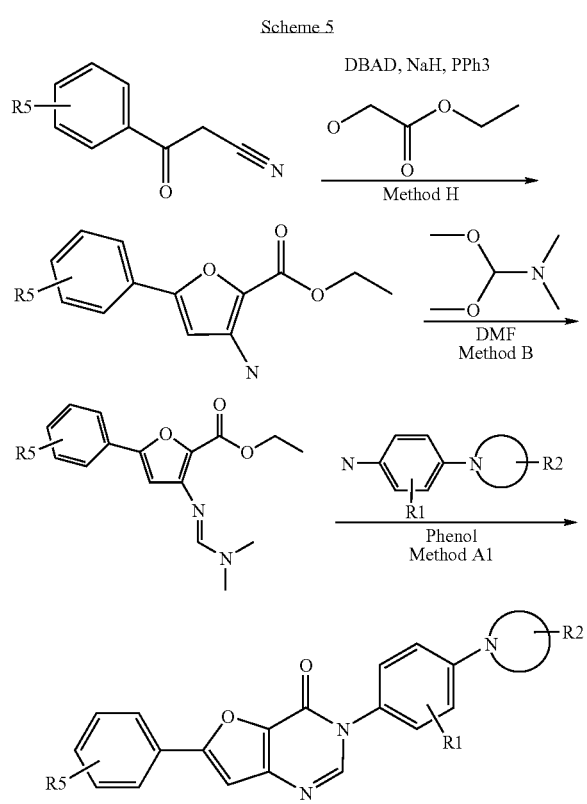
Other examples again were obtained as indicated in the following scheme.
Scheme 6
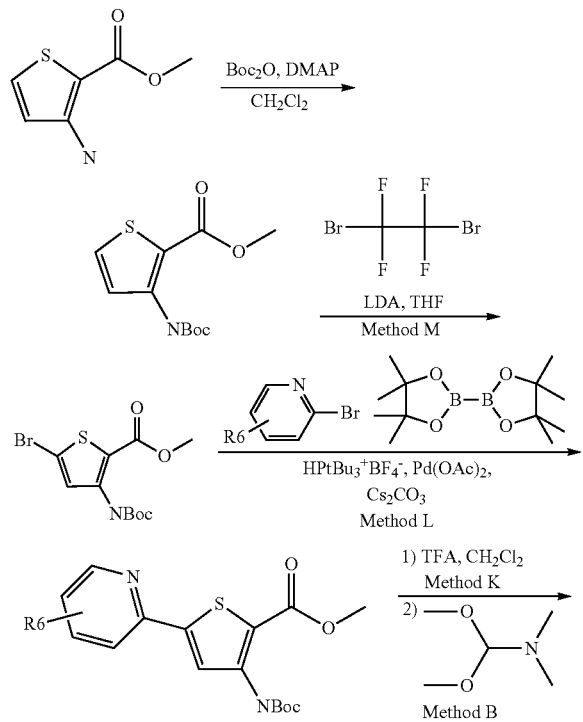
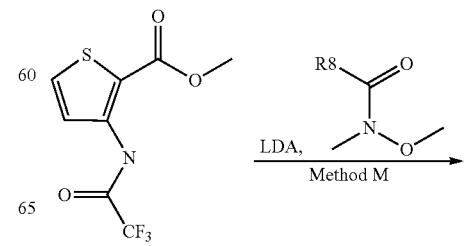
Other examples again were obtained as indicated in the following scheme.
Scheme 7

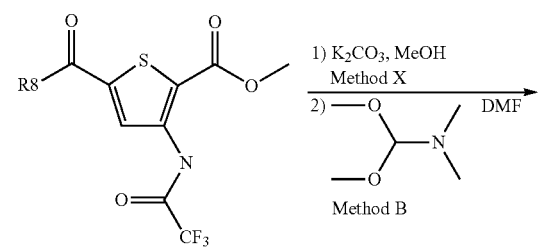
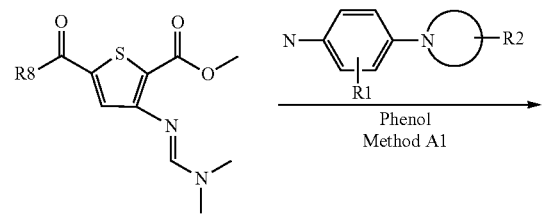
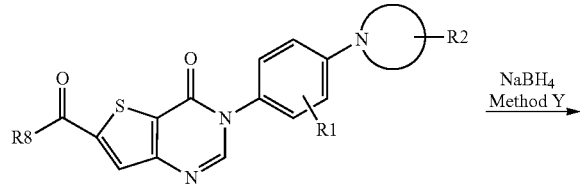
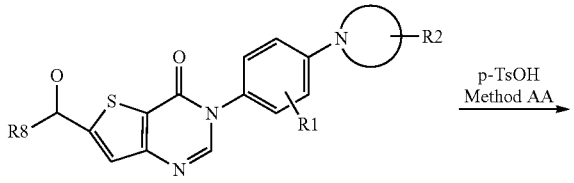
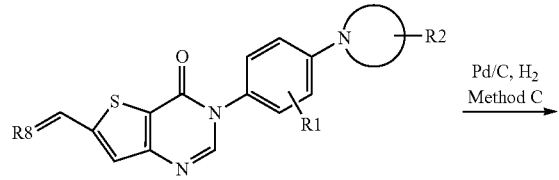
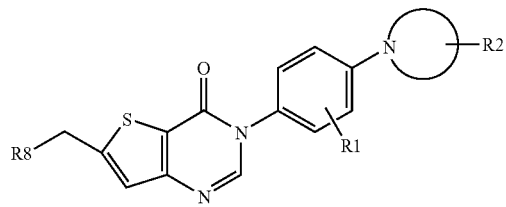
Other examples again were obtained as indicated in the following scheme.
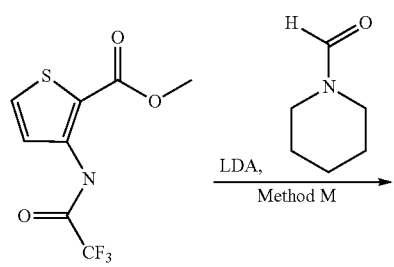
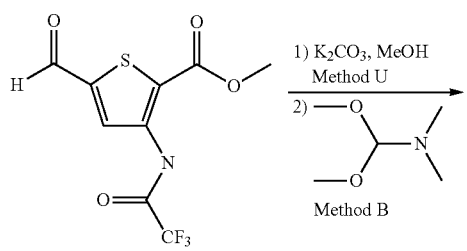
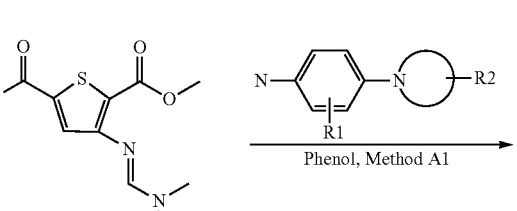
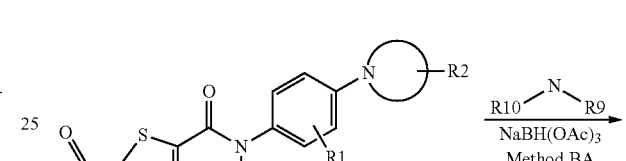
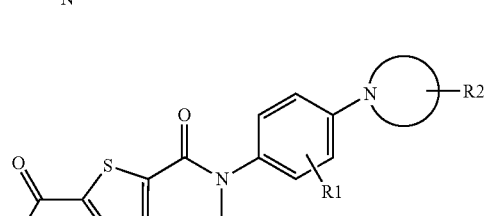
Other examples again were obtained as indicated in the following scheme.
Scheme 9
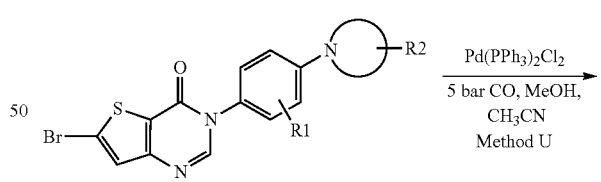
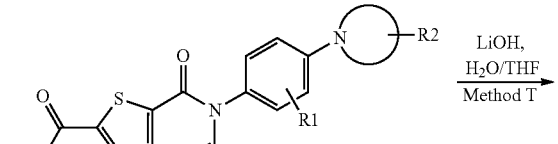

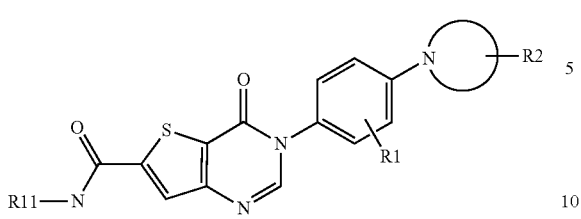

Other examples again were obtained as indicated in the following scheme.

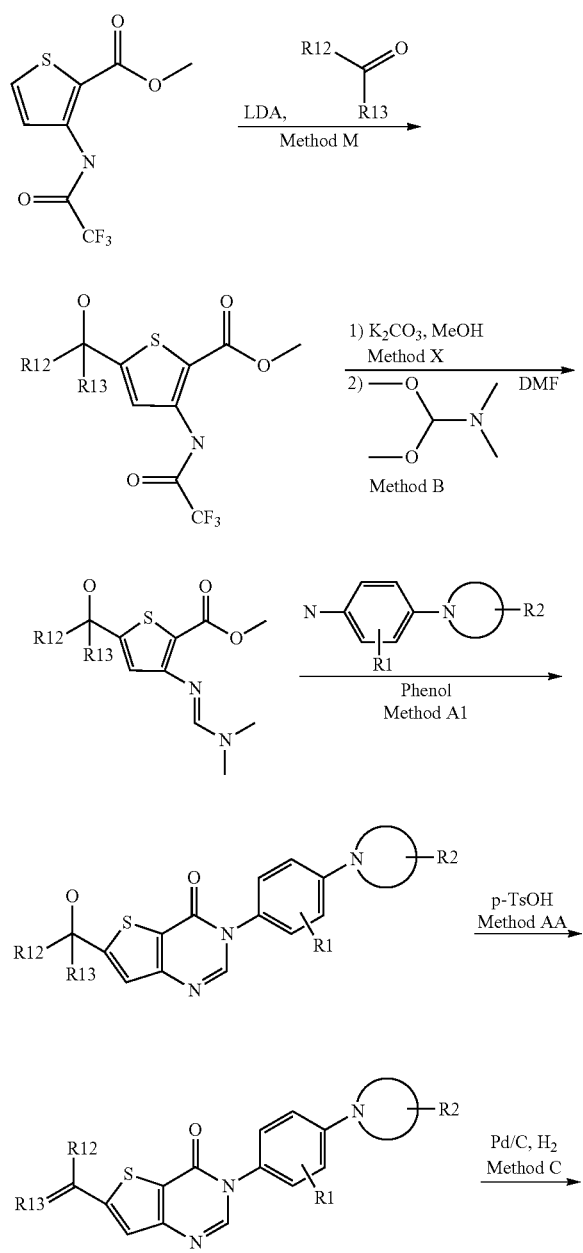

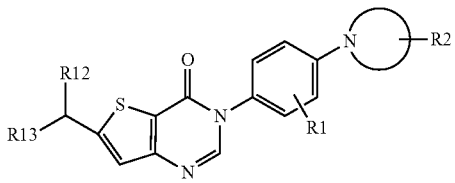

Descriptions of the general methods used are described by way of example in the following places:
Method A1, B, C and D in example 1;
Method A2, E, F and G in example 2;
Method H, I, J, K, L, M, N according to table 1;
Method O in example 19;
Method P in example 21;
Method Q in example 24;
Method R in example 66;
Method S, T and U in example 69
Method V and W in example 74;
Method X in example 75;
Method Y in example 76;
Method Z in example 79;
Method AA in example 85;
Method BA in example 93.

General Explanations a) Mode of Drawing the Structural Formulae

Only non-hydrogen atoms are depicted for clarity in the structural formulae of the given examples.

b) Salt Forms

Many of the compounds of the invention are bases and can form salts with appropriately strong acids. The compounds can in particular be in the form of hydrotrifluoroacetates after purification by HPLC chromatography using a mobile phase containing trifluoroacetic acid. These can be converted into the free bases shown by simple treatment of a solution of the salts for example with sodium carbonate solution.

c) Units of the Characterizing Data

The unit of the indicated molecular weights is "g/mol". Peaks observed in the mass spectrum are stated as integral quotient of the molar molecular ion mass and the charge of the molecular ion (m/z).

Example 1

6-(4-Chlorophenyl)-3-[4-(3-dimethylaminopyrrolidin-1-yl)-2-methylphenyl]-3H-thieno[3,2-d]pyrimidin-4-one

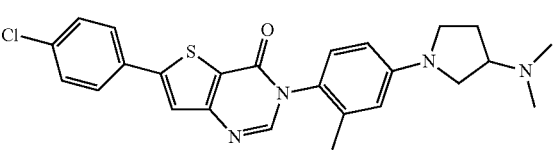 [SMILES: Cc1cc(N2CCC(N(C)C)C2)ccc1-n1cnc2cc(-c3ccc(Cl)cc3)sc2c1=O]

Method A1

A mixture of 5-(4-chlorophenyl)-3-(dimethylaminomethyleneamino)thiophene-2-carboxylic acid methyl ester (100 mg), [1-(4-amino-3-methylphenyl)pyrrolidin-3-yl]dimethylamine (68 mg) and Phenol (29 mg) was heated at 80° C. for 2 hours. The crude product was purified by preparative HPLC.

(An alternative possibility is also to dilute the reaction mixture with a little ethyl acetate and to isolate the crystalline product by filtration). The product with the molecular weight of 465.02 (C25H25ClN4OS) was obtained in this way; MS (ESI): 465 (M+H+).
Method B 5-(4-Chlorophenyl)-3-(dimethylaminomethylene-amino)thiophene-2-carboxylic acid methyl ester A solution of 3-amino-5-(4-chlorophenyl)thiophene-2-carboxylic acid methyl ester (5.0 g) in DMF (30 μL) was mixed with dimethoxymethyldimethylamine (5 mL) and stirred for 36 hours. The reaction solution was partitioned between water and ethyl acetate. The organic phase was dried over magnesium sulfate and concentrated. The product with the molecular weight of 322.82 (C15H15ClN2O2S) was obtained in this way; MS (ESI): 323 (M+H+).
Method C

[1-(4-Amino-3-methylphenyl)pyrrolidin-3-yl]dimethylamine

A suspension of dimethyl-[1-(3-methyl-4-nitrophenyl) pyrrolidin-3-yl]amine (200 mg) and palladium (10% on carbon, 10 mg) in methanol (10 mL) was vigorously stirred under an atmosphere of hydrogen at atmospheric pressure for 5 hours. The catalyst was then filtered off with suction and the filtrate was concentrated. The product with the molecular weight of 219.33 (C13H21N3) was obtained in this way; MS (ESI): 220 (M+H+).
Method D Dimethyl-[1-(3-methyl-4-nitrophenyl)pyrrolidin-3-yl]amine A mixture of 4-fluoro-2-methyl-1-nitrobenzene (13.6 g), dimethylpyrrolidin-3-ylamine (10.0 g), potassium carbonate (12 g) and DMF (100 mL) was stirred at room temperature for 4 hours. The reaction mixture was partitioned between water and ethyl acetate. The organic phase was dried and concentrated. The product with the molecular weight of 249.32 (C13H19N3O2) was obtained in this way; MS (ESI): 250 (M+H+).

Example 2

7-Butoxy-3-[4-((R)-3-dimethylaminopyrrolidin-1-yl)-2-methylphenyl]-3H-quinazolin-4-one

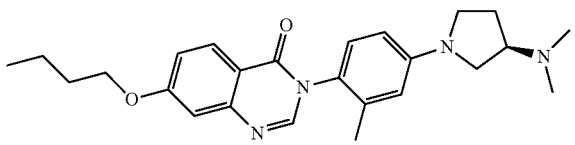 [SMILES: CCCCOc1ccc2c(=O)n(-c3ccc(N4CC[C@@H](N(C)C)C4)cc3C)cnc2c1]

Method A2
A mixture of 2-amino-4-butoxybenzoic acid (70 mg), [(R)-1-(4-amino-3-methylphenyl)-pyrrolidin-3-yl]dimethylamine (73.4 mg), ytterbium(III) triflate (2.1 mg) and ethyl orthoformate (49.6 mg) was heated at 100° C. for 7 hours. The crude product was purified directly by preparative HPLC. The product with the molecular weight of 420.56 (C25H32N4O2) was obtained in this way; MS (ESI): 421 (M+H+).

4-Butoxy-2-(dimethylaminomethyleneamino)benzoic acid methyl ester

2-Amino-4-butoxybenzoic acid methyl ester was reacted with dimethoxymethyldimethylamine by method B. The product with the molecular weight of 278.35 (C15H22N2O3) was obtained in this way; MS (ESI): 279 (M+H+).
Method E 2-Amino-4-butoxybenzoic acid methyl ester A mixture of 2-amino-4-butoxybenzoic acid (2.0 g), thionyl chloride (1.2 g) and methanol (33 mL) was boiled under reflux for 24 hours. The reaction solution was diluted with MTBE and washed with sodium hydroxide solution. The organic phase was dried and concentrated. The product with the molecular weight of 223.27 (C12H17NO3) was obtained in this way; MS (ESI): 224 (M+H+).

2-Amino-4-butoxybenzoic acid

4-Butoxy-2-nitrobenzoic acid was hydrogenated by method C1. The product with the molecular weight of 209.25 (C11H15NO3) was obtained in this way; MS (ESI): 210 (M+H+).
Method F 4-Butoxy-2-nitrobenzoic acid Potassium permanganate (9.8 g) was added in portions to a mixture of 4-butoxy-1-methyl-2-nitrobenzene (13.0 g), pyridine (100 mL) and water (100 mL) at 100° C. The same amount of potassium permanganate was added four more times after 1.5 hours on each occasion. The cooled reaction mixture was filtered with suction to remove solids, and the filtrate was partitioned between water and MTBE. The aqueous phase was acidified and extracted with ethyl acetate. The organic phase was dried and concentrated. The product with the molecular weight of 239.23 (C11H13NO5) was obtained in this way; MS (ESI): 240 (M+H+).
Method G 4-Butoxy-1-methyl-2-nitrobenzene A mixture of 4-methyl-3-nitrophenol (10.0 g), butyl bromide (9.4 g), sodium carbonate (6.9 g) and DMF (50 mL) was heated at 80° C. for 7 hours. The cooled reaction solution was diluted with MTBE and washed twice each with water and sodium hydroxide solution. The organic phase was dried and concentrated. The product with the molecular weight of 209.25 (C11H15NO$_3$) was obtained in this way; MS (ESI): 210 (M+H+).

The exemplary compounds in table 1 were obtained by method A1 or A2 from the appropriate esters and the appropriate anilines.

TABLE 1

| Ex. No. | Structure | Molecular formula | Molecular weight | ESI-MS [M + H]+ |
|---|---|---|---|---|
| 3 | 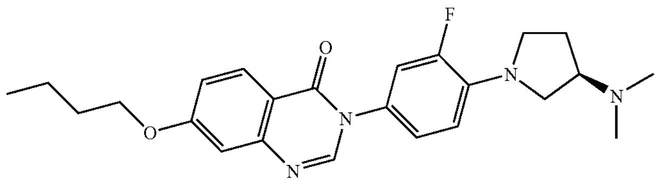 [SMILES: CCCCOc1ccc2c(=O)n(-c3ccc(N4CC[C@@H](N(C)C)C4)c(F)c3)cnc2c1] | C24H29FN4O2 | 424.52 | 425 |
| 4 | 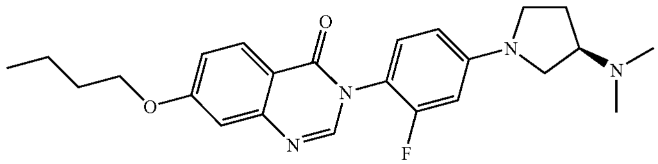 [SMILES: CCCCOc1ccc2c(=O)n(-c3ccc(N4CC[C@@H](N(C)C)C4)cc3F)cnc2c1] | C24H29FN4O2 | 424.52 | 425 |
| 5 | 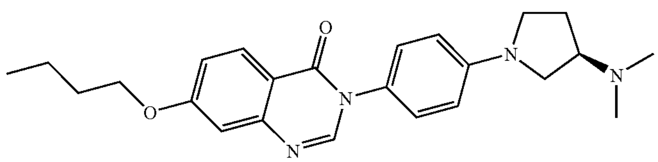 [SMILES: CCCCOc1ccc2c(=O)n(-c3ccc(N4CC[C@@H](N(C)C)C4)cc3)cnc2c1] | C24H30N4O2 | 406.53 | 407 |
| 6 | 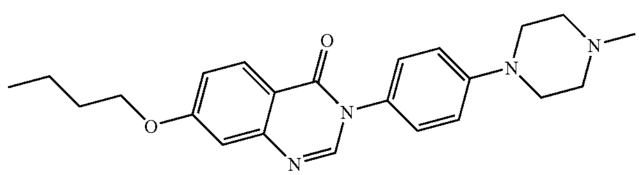 [SMILES: CCCCOc1ccc2c(=O)n(-c3ccc(N4CCN(C)CC4)cc3)cnc2c1] | C23H28N4O2 | 392.51 | 393 |
| 7 | 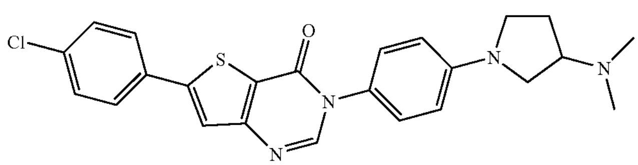 [SMILES: CN(C)C1CCN(c2ccc(-n3cnc4cc(-c5ccc(Cl)cc5)sc4c3=O)cc2)C1] | C24H23ClN4OS | 450.99 | 451 |
| 8 | 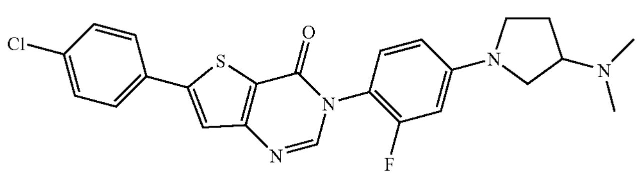 [SMILES: CN(C)C1CCN(c2ccc(-n3cnc4cc(-c5ccc(Cl)cc5)sc4c3=O)c(F)c2)C1] | C24H22ClFN4OS | 468.98 | 469 |
| 9 | 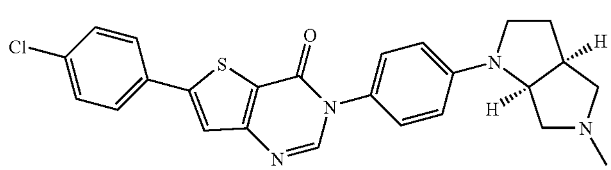 [SMILES: CN1C[C@@H]2CCN(c3ccc(-n4cnc5cc(-c6ccc(Cl)cc6)sc5c4=O)cc3)[C@@H]2C1] | C25H23ClN4OS | 463.01 | 463 |
| 10 | 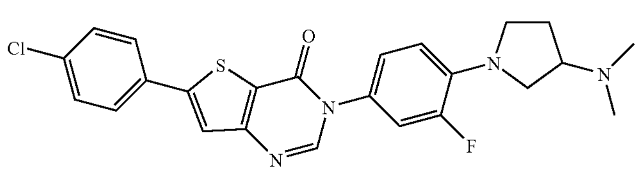 [SMILES: CN(C)C1CCN(c2ccc(-n3cnc4cc(-c5ccc(Cl)cc5)sc4c3=O)cc2F)C1] | C24H22ClFN4OS | 468.98 | 469 |
| 11 | 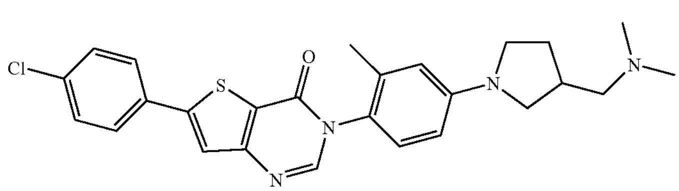 [SMILES: Cc1cc(N2CCC(CN(C)C)C2)ccc1-n1cnc2cc(-c3ccc(Cl)cc3)sc2c1=O] | C26H27ClN4OS | 479.05 | 479 |

TABLE 1-continued

| Ex. No. | Structure | Molecular formula | Molecular weight | ESI-MS [M + H]+ |
|---|---|---|---|---|
| 12 | 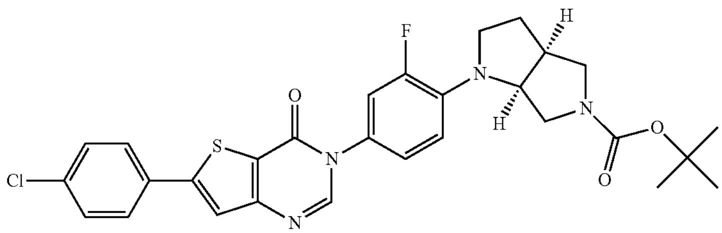 [SMILES: CC(C)(C)OC(=O)N1C[C@@H]2CCN(c3ccc(-n4cnc5cc(-c6ccc(Cl)cc6)sc5c4=O)cc3F)[C@@H]2C1] | C29H28ClFN4O3S | 567.09 | 567 |
| 13 | 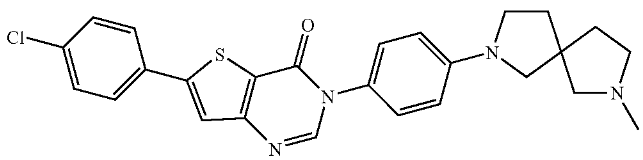 [SMILES: CN1CCC2(CCN(c3ccc(-n4cnc5cc(-c6ccc(Cl)cc6)sc5c4=O)cc3)C2)C1] | C26H25ClN4OS | 477.03 | 477 |
| 14 | 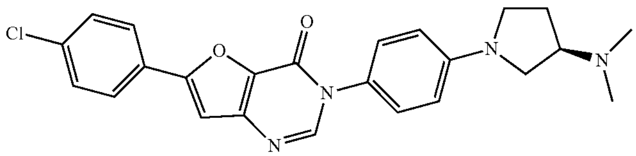 [SMILES: CN(C)[C@@H]1CCN(c2ccc(-n3cnc4cc(-c5ccc(Cl)cc5)oc4c3=O)cc2)C1] | C24H23ClN4O2 | 434.93 | 435 |
| 15 | 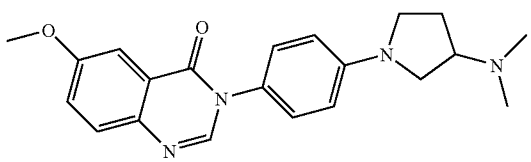 | C21H24N4O2 | 364.45 | 365 |
| 16 | 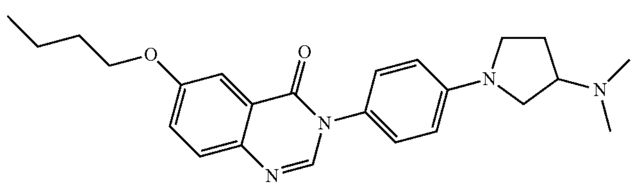 [SMILES: CCCCOc1ccc2ncn(-c3ccc(N4CCC(N(C)C)C4)cc3)c(=O)c2c1] | C24H30N4O2 | 406.53 | 407 |
| 17 | 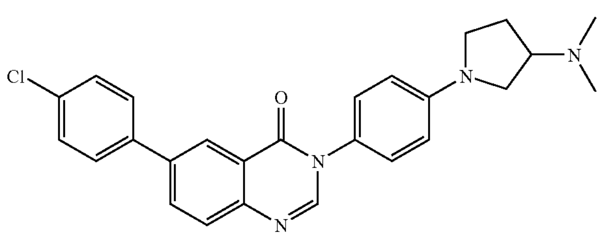 [SMILES: CN(C)C1CCN(c2ccc(-n3cnc4ccc(-c5ccc(Cl)cc5)cc4c3=O)cc2)C1] | C26H25ClN4O | 444.97 | 445 |
| 18 | 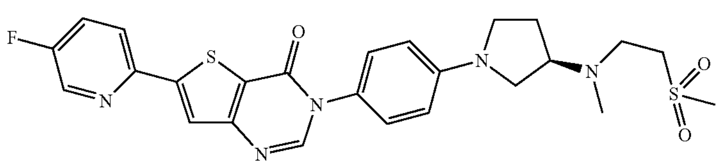 [SMILES: CN(CCS(C)(=O)=O)[C@@H]1CCN(c2ccc(-n3cnc4cc(-c5ccc(F)cn5)sc4c3=O)cc2)C1] | C25H26FN5O3S2 | 527.64 | 528 |

Reaction of the appropriate amino carboxylic acids with dimethoxymethyldimethylamine resulted in the following compounds:

5-(4-Chlorophenyl)-3-(dimethylaminomethyleneamino)-furan-2-carboxylic acid methyl ester;

2-(dimethylaminomethyleneamino)-5-methoxy-benzoic acid methyl ester;

5-butoxy-2-(dimethylaminomethyleneamino)-benzoic acid methyl ester;

4'-chloro-4-(dimethylaminomethyleneamino)-biphenyl-3-carboxylic acid methyl ester;

3-(dimethylaminomethyleneamino)-5-(5-fluoropyridin-2-yl)-thiophene-2-carboxylic acid methyl ester.

Method H

3-Amino-5-(4-chlorophenyl)-furan-2-carboxylic acid methyl ester

Di-tert-butyl azodicarboxylate (8.98 g) was added to a mixture of 3-(4-chlorophenyl)-3-oxopropionitrile (5.0 g), hydroxyacetic acid ethyl ester (4.06 g), triphenylphosphine (10.2 g) and THF (100 mL). After 15 hours, sodium hydride (55% in oil; 3.4 g) was added. After 5 hours, the reaction mixture was cautiously hydrolyzed with water and extracted with ethyl acetate. The organic phase was washed with hydrochloric acid, dried and concentrated. The residue was purified by preparative HPLC. The methyl ester was prepared by treatment with sodium methanolate in methanol. The product with the molecular weight of 251.67 (C12H10ClNO3) was obtained in this way; MS (ESI): 252 (M+H+).

2-Amino-5-butoxybenzoic acid methyl ester

5-Butoxy-2-nitrobenzoic acid methyl ester was reduced by method C. The product with the molecular weight of 223.27 (C12H17NO3) was obtained in this way; MS (ESI): 224 (M+H+).

Method I

5-Butoxy-2-nitrobenzoic acid methyl ester

Sodium hydride (302.4 mg) was added to a solution of 1-butanol (0.634 mL) in DMF (15 mL). The reaction mixture was stirred until there was no further evolution of CO2 and then 5-fluoro-2-nitrobenzoic acid methyl ester (1.15 g) was added and the mixture was stirred at room temperature overnight. The reaction was then mixed with ethyl acetate, washed with 10% sodium bicarbonate and 10% citric acid solution, dried over sodium sulfate and concentrated. The crude product was purified by preparative HPLC. The product with the molecular weight of 253.26 (C12H15NO5) was obtained in this way; MS (ESI): 254 (M+H+).

5-Fluoro-2-nitrobenzoic acid methyl ester

5-Fluoro-2-nitrobenzoic acid was esterified by method E. The product with the molecular weight of 199.14 (C8H6FNO4) was obtained in this way; MS (ESI): 200 (M+H+).

3-[4-(3-Dimethylaminopyrrolidin-1-yl)phenyl]-6-methoxy-3H-quinazolin-4-one

[1-(4-Aminophenyl)pyrrolidin-3-yl]dimethylamine was reacted with 5-butoxy-2-[2-methylprop-(Z)-ylideneamino] benzoic acid methyl ester, which had previously been rinsed with methanol, by method A1. Methanol residues resulted in a transetherification, resulting in the product.

Method J

4-Amino-4'-chlorobiphenyl-3-carboxylic acid methyl ester

A solution of 2-amino-5-bromobenzoic acid methyl ester (460.1 mg) in degassed toluene was mixed with tetrakis (triphenylphosphine)palladium (0) (62.4 mg) and stirred at room temperature for 10 min. Then 4-chlorophenylboronic acid (344 mg) in ethanol (0.76 mL) and 2 M sodium carbonate solution (1.34 mL) were added, and the reaction mixture was heated at 100° C. overnight. The reaction was then mixed with ethyl acetate and water. The aqueous phase was extracted several times with ethyl acetate. The combined organic phases were dried over sodium sulfate and concentrated. The crude product was purified by preparative HPLC. The product with the molecular weight of 261.71 (C14H12ClNO2) was obtained in this way; MS (ESI): 262 (M+H+).

Method K

3-Amino-5-(5-fluoropyridin-2-yl)thiophene-2-carboxylic acid methyl ester

A solution of 3-tert-butoxycarbonylamino-5-(5-fluoropyridin-2-yl)-thiophene-2-carboxylic acid methyl ester (80 mg) in dichloromethane (1.35 mL) was mixed with trifluoroacetic acid (0.15 mL) and stirred at room temperature overnight. The solvent was then removed in vacuo, and the residue was taken up again in dichloromethane and washed twice with saturated NaHCO3 solution and once with water. The dichloromethane phase was dried over sodium sulfate and concentrated. The product with the molecular weight of 252.27 (C11H9FN2O2S) was obtained in this way; MS (ESI): 253 (M+H+).

Method L

3-tert-Butoxycarbonylamino-5-(5-fluoropyridin-2-yl)thiophene-2-carboxylic acid methyl ester Palladium(II) acetate (20 mg) was added to a solution of 5-bromo-3-tert-butoxycarbonylaminothiophene-2-carboxylic acid methyl ester (300 mg), 2-bromo-5-fluoropyridine (235.5 mg), bis(pinacolato)diboron (462.2 mg), tri-t-butylphosphonium tetrafluoroborate (77.64 mg) and cesium carbonate (871.9 mg) in dioxane/water (6 mL/1.5 mL). The solution was heated at 90° C. for 3 h. The reaction solution was then mixed with ethyl acetate and water. The aqueous phase was extracted several times with ethyl acetate. The combined organic phases were dried over sodium sulfate and concentrated. The crude product was purified by preparative HPLC. The product with the molecular weight of 352.39 (C16H17FN2O4S) was obtained in this way; MS (ESI): 353 (M+H+).

Method M

5-Bromo-3-tert-butoxycarbonylaminothiophene-2-carboxylic acid methyl ester

A 1.6 M solution of n-butyllithium in hexane (7.4 mL) was added to a solution of diisopropylamine (1.27 g) in THF (18 mL) at −78° C. in a flask which had been heat-dried and flushed with argon. The solution was warmed to 0° C. and stirred at this temperature for 10 min. The reaction solution was then cooled to −78° C. again and a solution of 3-tert-butoxycarbonylaminothiophene-2-carboxylic acid methyl ester (0.93 g) in THF (10 mL) was added. The mixture was stirred at −78° C. for 30 min. 1,2-dibromotetrafluoroethane (5.61 g) was then added to the reaction solution, which was stirred at −78° C. for a further hour. After addition of a saturated ammonium chloride solution, the solution was allowed to warm to room temperature. The reaction solution was extracted twice with ethyl acetate and then the combined organic phases were washed with water and saturated sodium chloride solution, dried over sodium sulfate and concentrated. The residue was purified by chromatography on silica gel. The product with the molecular weight of 336.21 (C11H14BrNO4S) was obtained in this way; MS (ESI): 335, 337 (M+H+).

Method N 3-tert-Butoxycarbonylaminothiophene-2-carboxylic acid methyl ester

Di-tert-butyldicarbonate (41.6 g) and 4-dimethylaminopyridine (0.77 g) were added to a mixture of methyl 3-aminothiophene-2-carboxylate (20 g) in dichloromethane (350 mL). The reaction was stirred at room temperature for 1 h, and then the solvent was removed in vacuo. The residue was taken up in ethyl acetate and washed with saturated sodium bicarbonate solution, 10% strength citric acid solution and saturated sodium chloride solution. The ethyl acetate phase was then dried over sodium sulfate and concentrated. The residue was purified by chromatography on silica gel. The product with the molecular weight of 257.31 (C11H15NO4S) was obtained in this way; MS (ESI): 158 (N-Boc+H+).

The following anilines were prepared by method D and C1 from the appropriate 4-fluoro-nitrobenzenes and the appropriate amines:

[(R)-1-(4-amino-3-methylphenyl)pyrrolidin-3-yl]dimethylamine;
[(R)-1-(4-amino-2-fluorophenyl)pyrrolidin-3-yl]dimethylamine;
[(R)-1-(4-amino-3-fluorophenyl)pyrrolidin-3-yl]dimethylamine (from 2-chloro-1,3-difluoro-4-nitrobenzene and dimethyl-(R)-pyrrolidin-3-ylamine);
[(R)-1-(4-aminophenyl)pyrrolidin-3-yl]dimethylamine;
4-(4-methylpiperazin-1-yl)phenylamine;
4-(4-methyl[1,4]diazepan-1-yl)phenylamine;
[1-(4-aminophenyl)pyrrolidin-3-yl]dimethylamine;
[1-(4-amino-3-fluorophenyl)pyrrolidin-3-yl]dimethylamine (from 2-chloro-1,3-difluoro-4-nitrobenzene and dimethylpyrrolidin-3-yl-amine);
4-((3aS,6aS)-5-methylhexahydropyrrolo[3,4-b]pyrrol-1-yl)phenylamine;
[1-(4-amino-2-fluorophenyl)pyrrolidin-3-yl]dimethylamine;
4-(3-dimethylaminomethylpyrrolidin-1-yl)-2-methylphenylamine;
(3aS,6aS)-1-(4-amino-2-fluorophenyl)hexahydropyrrolo[3,4-b]pyrrole-5-carboxylic acid tert-butyl ester;
4-(7-methyl-2,7-diazaspiro[4,4]non-2-yl)phenylamine
(3R)-4-[1,3']bipyrrolidinyl-1'-yl-3-methylphenylamine.
[(R)-1-(4-Aminophenyl)pyrrolidin-3-yl]-(2-methanesulfonylethyl)methylamine
[(R)-1-(2-Chloro-4-nitrophenyl)pyrrolidin-3-yl]-(2-methanesulfonylethyl)methylamine was dechlorinated and the nitro group was reduced to the amine under the conditions of method C1. The crude product was purified by preparative HPLC. The product with the molecular weight of 297.42 (C14H23N3O2S) was obtained in this way; MS (ESI): 298 (M+H+).

[(R)-1-(2-Chloro-4-nitrophenyl)pyrrolidin-3-yl]-(2-methanesulfonylethyl)methylamine A mixture of [(R)-1-(2-chloro-4-nitrophenyl)pyrrolidin-3-yl]methylamine (384 mg), methanesulfonylethene (318 mg) and methanol (5 mL) was stirred at room temperature for 12 hours. Volatiles were evaporated off, and the residue was purified by preparative HPLC. The product with the molecular weight of 361.85 (C14H20ClN3O4S) was obtained in this way; MS (ESI): 362 (M+H+).

[(R)-1-(2-Chloro-4-nitrophenyl)pyrrolidin-3-yl]methylamine

[(R)-1-(2-Chloro-4-nitrophenyl)pyrrolidin-3-yl]methylcarbamic acid tert-butyl ester was deblocked by method K. The product with the molecular weight of 255.71 (C11H14ClN3O2) was obtained in this way; MS (ESI): 256 (M+H+).

[(R)-1-(2-Chloro-4-nitrophenyl)pyrrolidin-3-yl]methylcarbamic acid tert-butyl ester was obtained from 2-chloro-1-fluoro-4-nitrobenzene and methyl-(R)-pyrrolidin-3-yl-carbamic acid tert-butyl ester by method D.

(R)-[1,3']Bipyrrolidinyl

Methanesulfonyl chloride was added to a mixture of (S)-3-hydroxypyrrolidine-1-carboxylic acid tert-butyl ester (40 g) and pyridine (17.4 g) in dichloromethane (400 mL) at 0° C. The reaction mixture was stirred at this temperature for 15 min and then heated at 50° C. for 8 h. The reaction mixture was subsequently mixed with ethyl acetate and water, and the ethyl acetate phase was washed with dil. HCl solution. The ethyl acetate phase was dried over sodium sulfate and the solvent was removed in vacuo. The (R)-3-methanesulfonyloxypyrrolidine-1-carboxylic acid tert-butyl ester obtained in this way was dissolved in pyrrolidine (18.2 mL), and the reaction mixture was heated to 100° C. The reaction mixture was then mixed with ethyl acetate and water. The ethyl acetate phase was washed several times with water. The organic phase was dried over sodium sulfate and the solvent was removed in vacuo.

(R)-[1,3']Bipyrrolidinyl-1'-carboxylic acid tert-butyl ester was deblocked by method K. The product with the molecular weight of 140.13 (C8H16N2) was obtained in this way; MS (ESI): 141 (M+H+).

Example 19

7-Butoxy-3-[2-fluoro-4-((R)-3-methylaminopyrrolidin-1-yl)phenyl]-3H-quinazolin-4-one

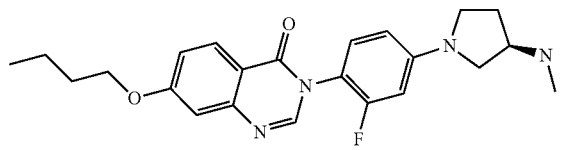 [SMILES: CCCCOc1ccc2c(=O)n(-c3ccc(N4CC[C@@H](NC)C4)cc3F)cnc2c1]

{(R)-1-[4-(7-Butoxy-4-oxo-4H-quinazolin-3-yl)-3-fluorophenyl]pyrrolidin-3-yl}methylcarbamic acid tert-butyl ester was treated by method K. The product with the molecular weight of 410.50 (C23H27FN4O2) was obtained in this way; MS (ESI): 411 (M+H+).

{(R)-1-[4-(7-Butoxy-4-oxo-4H-quinazolin-3-yl)-3-fluorophenyl]pyrrolidin-3-yl}methylcarbamic acid tert-butyl ester 2-Amino-4-butoxybenzoic acid was reacted with [(R)-1-(4-amino-3-fluorophenyl)pyrrolidin-3-yl]methylcarbamic acid tert-butyl ester by method A2. The product with the molecular weight of 510.61 (C28H35FN4O4) was obtained in this way; MS (ESI): 511 (M+H+).

[(R)-1-(4-Amino-3-fluorophenyl)pyrrolidin-3-yl]methylcarbamic acid tert-butyl ester

[(R)-1-(3-Fluoro-4-nitrophenyl)pyrrolidin-3-yl]methylcarbamic acid tert-butyl ester was hydrogenated under the conditions of method C1. The product with the molecular weight of 309.39 (C16H24FN3O2) was obtained in this way; MS (ESI): 310 (M+H+).

Method O

[(R)-1-(3-fluoro-4-nitrophenyl)pyrrolidin-3-yl]methylcarbamic acid tert-butyl ester Sodium hydride (0.6 g) was added in portions to a solution of [(R)-1-(3-fluoro-4-nitro-phenyl)pyrrolidin-3-yl]carbamic acid tert-butyl ester (4.09 g) in DMF (10 mL). After gas evolution ceased, iodomethane (2.37 mL) was added dropwise. After 12 hours, the mixture was partitioned between water and ethyl acetate/hexane (1:1), and the organic phase was dried and concentrated. The product with the molecular weight of 339.37 (C16H22FN3O4) was obtained in this way; MS (ESI): 340 (M+H+).

[(R)-1-(3-Fluoro-4-nitrophenyl)pyrrolidin-3-yl]carbamic acid tert-butyl ester was obtained by method D from 1,3-difluoro-4-nitrobenzene and (R)-pyrrolidin-3-ylcarbamic acid tert-butyl ester.

Example 20

6-(4-Chlorophenyl)-3-((3aS,6aS)-3-fluoro-4-hexahydropyrrolo[3,4-b]pyrrol-1-yl-phenyl)-3H-thieno[3,2-d]pyrimidin-4-one

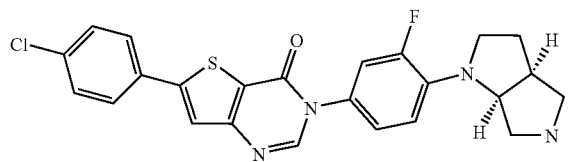 [SMILES: O=c1c2sc(-c3ccc(Cl)cc3)cc2ncn1-c1ccc(N2CC[C@H]3CNC[C@H]32)c(F)c1]

(3aS,6aS)-1-{4-[6-(4-Chlorophenyl)-4-oxo-4H-thieno[3,2-d]pyrimidin-3-yl]-2-fluoro-phenyl}hexahydropyrrolo[3,4-b]pyrrole-5-carboxylic acid tert-Butyl ester was treated by method K. The product with the molecular weight of 466.97 (C24H20ClFN4OS) was obtained in this way; MS (ESI): 467 (M+H+).

Example 21

6-(3-Hydroxy-but-1-ynyl)-3-[4-(4-methyl[1,4]diazepan-1-yl)phenyl]-3H-thieno[3,2-d]pyrimidin-4-one

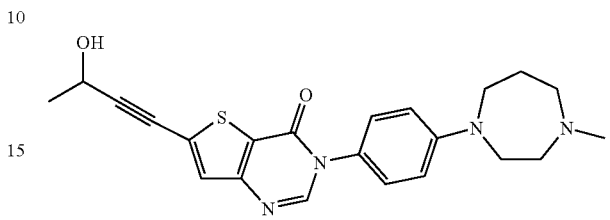

Method P

6-Bromo-3-[4-(4-methyl[1,4]diazepan-1-yl)phenyl]-3H-thieno[3,2-d]pyrimidin-4-one (33.6 mg), palladium bis(tri-tert-butylphosphine) (4.1 mg), copper iodide (1.5 mg) were introduced into a flask which had been heat-dried and ventilated with argon, and a solution of 3-methyl-1-butyne (28.0 mg), morpholine (0.469 mL) in dioxane/water (0.47 mL/0.0111 mL) was added. The reaction mixture was stirred at room temperature overnight. The solvent was then removed in vacuo, and the residue was taken up again in ethyl acetate and water. The aqueous phase was extracted several times with ethyl acetate. The combined organic phases were dried over sodium sulfate and concentrated. The crude product was purified by preparative HPLC. The product with the molecular weight of 408.52 (C22H24N4OS) was obtained in this way; MS (ESI): 409 (M+H+).

The compounds in table 2 were synthesized analogously.

6-Bromo-3-[4-(4-methyl[1,4]diazepan-1-yl)phenyl]-3H-thieno[3,2-d]pyrimidin-4-one 5-Bromo-3-(dimethylaminomethyleneamino)thiophene-2-carboxylic acid methyl ester was reacted with 4-(4-methyl[1,4]diazepan-1-yl)phenylamine by method A1 with addition of isopropanol in addition. The product with the molecular weight of 419.34 (C18H19BrN4OS) was obtained in this way; MS (EST): 419, 421 (N+H+).

TABLE 2

| Ex. No. | Structure | Molecular formula | Molecular weight | ESI-MS [M + H]+ |
|---|---|---|---|---|
| 22 | 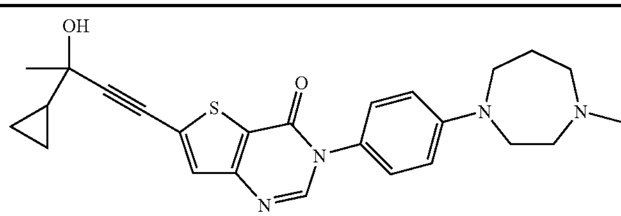 | C25H28N4O2S | 448.58 | 449 |
| 23 | 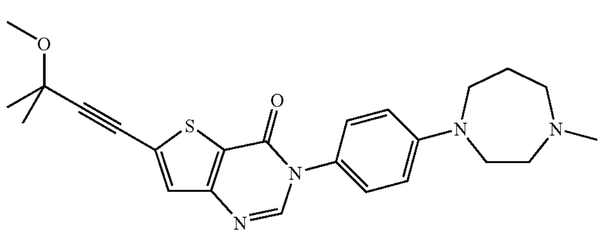 [SMILES: COC(C)(C)C#Cc1cc2ncn(-c3ccc(N4CCCN(C)CC4)cc3)c(=O)c2s1] | C24H28N4O2S | 436.57 | 437 |

Example 24

6-(1-Hydroxycyclopentylethynyl)-3-[4-(4-methyl[1,4]diazepan-1-yl)phenyl]-3H-thieno[3,2-d]pyrimidin-4-one

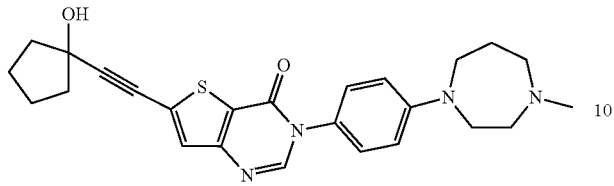

Method Q

6-Bromo-3-[3-methoxy-4-(2-pyrrolidin-1-yl-ethoxy)phenyl]-3H-thieno[3,2-d]pyrimidin-4-one (50.3 mg), triphenylphosphine (6.3 mg), 1-ethynylcyclopentanol (66.1 mg), bis(triphenylphosphine)palladium(II) chloride (4.2 mg) were introduced into NMP (1.5 mL) in a flask which had been heat-dried and ventilated with argon, and copper iodide (4.6 mg) was added. The reaction mixture was stirred at 85° C. for 4 h. The solvent was then removed in vacuo, and the residue was taken up again in ethyl acetate and water. The aqueous phase was freeze dried. The crude product was purified by preparative HPLC. The product with the molecular weight of 448.59 (C25H28N4O2S) was obtained in this way; MS (ESI): 449 (N+H+).

The compounds in table 3 were synthesized analogously.

Example 29

6-Cyclopropylethynyl-3-[4-(4-methyl[1,4]diazepan-1-yl)phenyl]-3H-thieno[3,2-d]pyrimidin-4-one

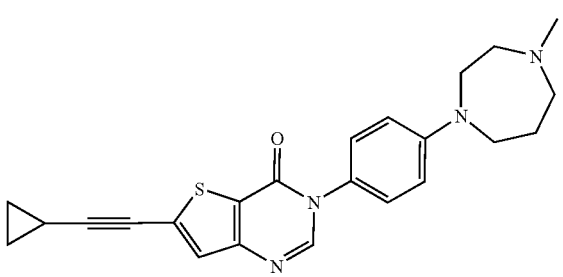

5-Cyclopropylethynyl-3-(dimethylaminomethyleneamino)thiophene-2-carboxylic acid methyl ester was reacted with 4-(4-methyl[1,4]diazepan-1-yl)phenylamine by method A1. The product with the molecular weight of 404.53 (C23H24N4OS) was obtained in this way; MS (ESI): 405 (M+H+).

TABLE 3

| Ex. No. | Structure | Molecular formula | Molecular weight | ESI-MS [M + H]+ |
|---|---|---|---|---|
| 25 | 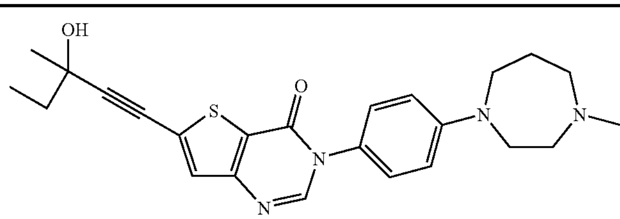 | C24H28N4O2S | 436.57 | 437 |
| 26 | 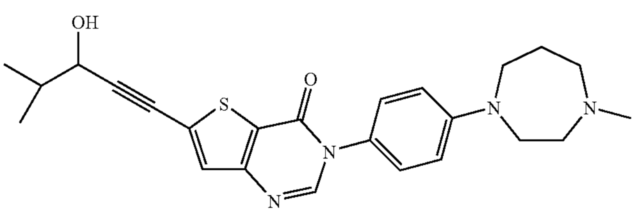 [SMILES: CC(C)C(O)C#Cc1cc2ncn(-c3ccc(N4CCCN(C)CC4)cc3)c(=O)c2s1] | C24H28N4O2S | 436.57 | 437 |
| 27 | 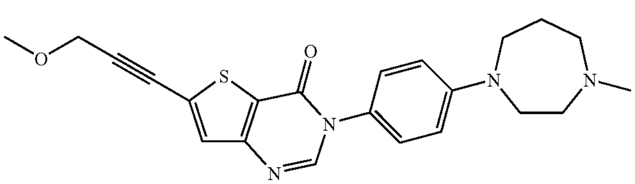 | C22H24N4O2S | 408.52 | 409 |
| 28 | 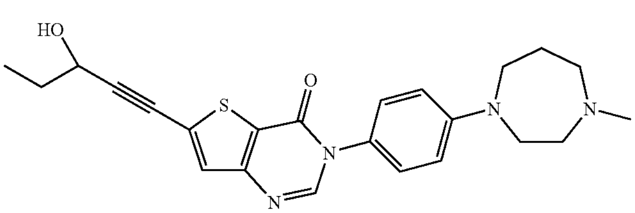 [SMILES: CCC(O)C#Cc1cc2ncn(-c3ccc(N4CCCN(C)CC4)cc3)c(=O)c2s1] | C23H26N4O2S | 422.55 | 423 |

5-Cyclopropylethynyl-3-(dimethylaminomethylene-amino)thiophene-2-carboxylic acid methyl ester 3-Amino-5-cyclopropylethynylthiophene-2-carboxylic acid methyl ester was reacted by method B. The product with the molecular weight of 276.35 (C14H16N2O2S) was obtained in this way; MS (ESI): 277 (M+H+).

3-Amino-5-cyclopropylethynylthiophene-2-carboxylic acid methyl ester

Tin chloride (11.8 g) was added to a solution of 5-cyclopropylethynyl-3-nitrothiophene-2-carboxylic acid methyl ester (6.26 g) in ethanol (250 ml), and the reaction mixture was heated to reflux for 4 h. The solvent was then removed in vacuo, and the residue was taken up again in ethyl acetate and washed with sat. Rochelle salt solution. The organic phase was dried over sodium sulfate and the solvent was removed in vacuo. The product with the molecular weight of 221.27 (C11H11NO2S) was obtained in this way; MS (ESI): 222 (M+H+).

5-Cyclopropylethynyl-3-nitrothiophene-2-carboxylic acid methyl ester

5-Bromo-3-nitrothiophene-2-carboxylic acid methyl ester was reacted with ethynylcyclopropane by method Q. The product with the molecular weight of 251.26 (C11H9NO4S) was obtained in this way; MS (ESI): 252 (M+H+).

Example 30

3-[4-((R)-3-Dimethylaminopyrrolidin-1-yl)phenyl]-6-(3-hydroxybut-1-ynyl)-3H-thieno[3,2-d]pyrimidin-4-one

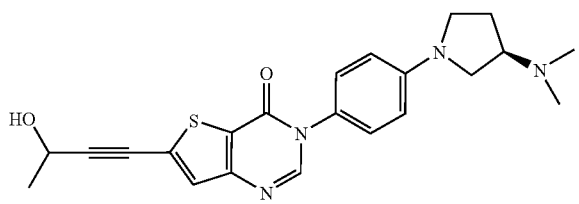 [SMILES: CC(O)C#Cc1cc2ncn(-c3ccc(N4CC[C@@H](N(C)C)C4)cc3)c(=O)c2s1]

6-Bromo-3-[4-((R)-3-dimethylaminopyrrolidin-1-ylphenyl]-3H-thieno[3,2-d]pyrimidin-4-one was reacted with but-3-yn-2-ol by method P. The product with the molecular weight of 408.52 (C22H24N4O2S) was obtained in this way; MS (ESI): 409 (M+H+).

The compounds in table 4 were prepared analogously.

6-Bromo-3-[4-((R)-3-dimethylaminopyrrolidin-1-yl)phenyl]-3H-thieno[3,2-d]pyrimidin-4-one 5-Bromo-3-(dimethylaminomethyleneamino)thiophene-2-carboxylic acid methyl ester was reacted with [(R)-1-(4-aminophenyl)pyrrolidin-3-yl]dimethylamine by method A1. The product with the molecular weight of 418.05 (C18H19BrN4OS) was obtained in this way; MS (ESI): 419 (M+H+).

TABLE 4

| Ex. No. | Structure | Molecular formula | Molecular weight | ESI-MS [M + H]+ |
|---|---|---|---|---|
| 31 | 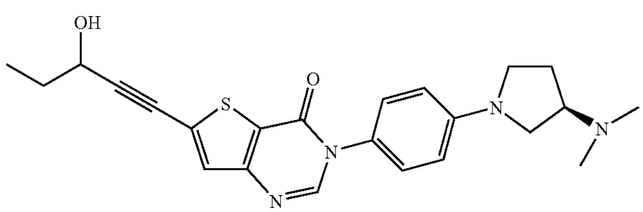 [SMILES: CCC(O)C#Cc1cc2ncn(-c3ccc(N4CC[C@@H](N(C)C)C4)cc3)c(=O)c2s1] | C23H26N4O2S | 422.55 | 423 |
| 32 | 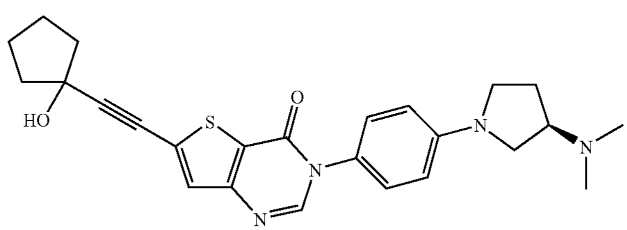 [SMILES: CN(C)[C@@H]1CCN(c2ccc(-n3cnc4cc(C#CC5(O)CCCC5)sc4c3=O)cc2)C1] | C25H28N4O2S | 448.58 | 449 |
| 33 | 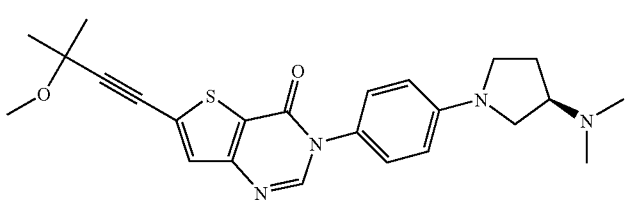 | C24H28N4O2S | 436.57 | 437 |

TABLE 4-continued
| Ex. No. | Structure | Molecular formula | Molecular weight | ESI-MS [M + H]+ |
|---|---|---|---|---|
| 34 | 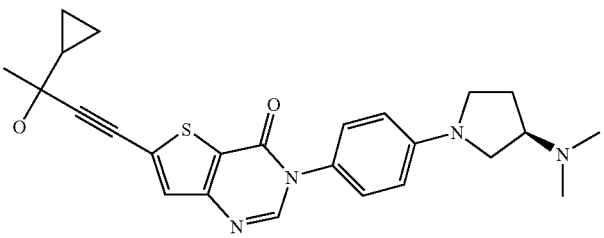 [SMILES: CN(C)[C@@H]1CCN(c2ccc(-n3cnc4cc(C#CC(C)(O)C5CC5)sc4c3=O)cc2)C1] | C25H28N4O2S | 448.58 | 449 |
| 35 | 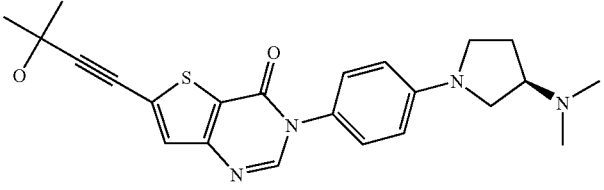 [SMILES: CN(C)[C@@H]1CCN(c2ccc(-n3cnc4cc(C#CC(C)(C)O)sc4c3=O)cc2)C1] | C23H26N4O2S | 422.55 | 423 |
| 36 | 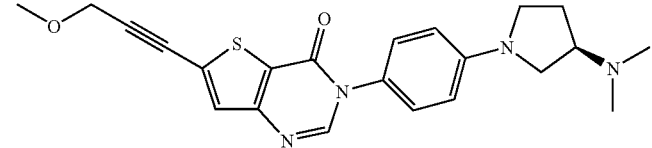 | C22H24N4O2S | 408.52 | 409 |
| 37 | 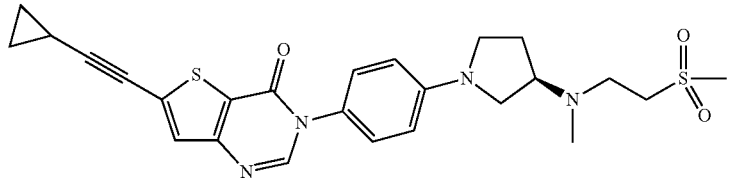 [SMILES: CN(CCS(C)(=O)=O)[C@@H]1CCN(c2ccc(-n3cnc4cc(C#CC5CC5)sc4c3=O)cc2)C1] | C25H28N4O3S2 | 496.64 | 497 |
| 38 | 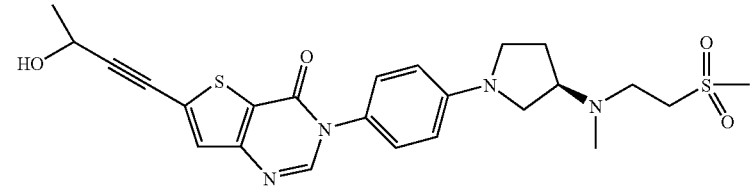 [SMILES: CC(O)C#Cc1cc2ncn(-c3ccc(N4CC[C@@H](N(C)CCS(C)(=O)=O)C4)cc3)c(=O)c2s1] | C24H28N4O4S2 | 500.63 | 501 |
| 39 | 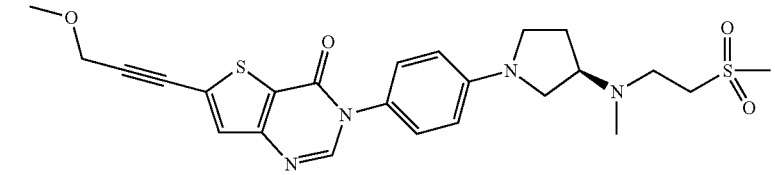 | C24H28N4O4S2 | 500.63 | 501 |
| 40 | 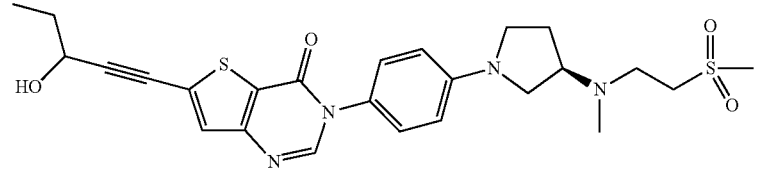 [SMILES: CCC(O)C#Cc1cc2ncn(-c3ccc(N4CC[C@@H](N(C)CCS(C)(=O)=O)C4)cc3)c(=O)c2s1] | C25H30N4O4S2 | 514.66 | 515 |

TABLE 4-continued

| Ex. No. | Structure | Molecular formula | Molecular weight | ESI-MS [M + H]+ |
|---|---|---|---|---|
| 41 | 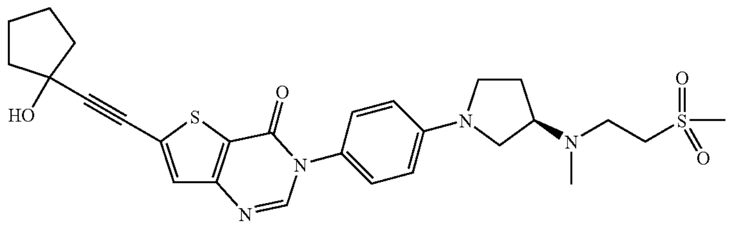 [SMILES: CN(CCS(C)(=O)=O)[C@@H]1CCN(c2ccc(-n3cnc4cc(C#CC5(O)CCCC5)sc4c3=O)cc2)C1] | C27H32N4O4S2 | 540.70 | 541 |
| 42 | 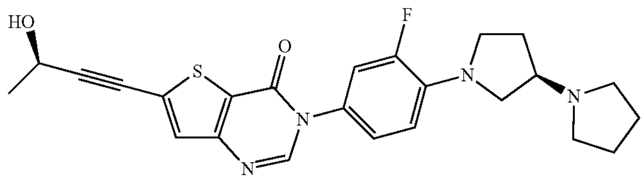 [SMILES: C[C@@H](O)C#Cc1cc2ncn(-c3ccc(N4CC[C@@H](N5CCCC5)C4)c(F)c3)c(=O)c2s1] | C24H25FN4O2S | 452.55 | 453 |
| 43 | 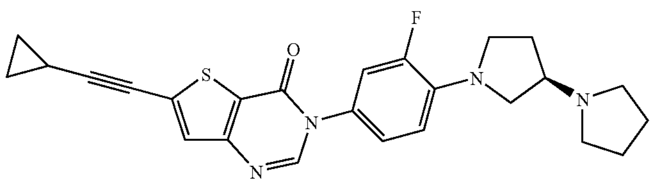 [SMILES: O=c1c2sc(C#CC3CC3)cc2ncn1-c1ccc(N2CC[C@@H](N3CCCC3)C2)c(F)c1] | C25H25FN4OS | 448.56 | 449 |

Example 44

6-Cyclopropylethynyl-3-{4-[4-(2-methanesulfonyl-ethyl)-[1,4]diazepan-1-yl]-phenyl}-3H-thieno[3,2-d]pyrimidin-4-one

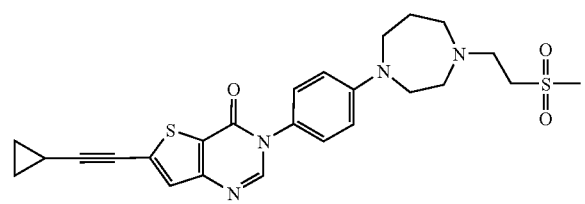 [SMILES: CS(=O)(=O)CCN1CCCN(c2ccc(-n3cnc4cc(C#CC5CC5)sc4c3=O)cc2)CC1]

5-Cyclopropylethynyl-3-(dimethylamino-methylene-amino)-thiophene-2-carboxylic acid methyl ester was reacted with 4-[4-(2-Methanesulfonyl-ethyl)-[1,4]diazepan-1-yl]-phenylamine by method A1. The product with the molecular weight of 496.64 (C25H28N4O3S2) was obtained in this way; MS (ESI): 497 (M+H+).

4-[4-(2-Methanesulfonyl-ethyl)-[1,4]diazepan-1-yl]-phenylamine 1-(2-Methanesulfonyl-ethyl)-4-(4-nitro-phenyl)-[1,4]diazepane was reduced by method C1. The product with the molecular weight of 297.42 (C14H23N3O2S) was obtained in this way; MS (ESI): 298 (M+H+).

1-(2-Methanesulfonyl-ethyl)-4-(4-nitro-phenyl)-[1,4]diazepane

A mixture of 1-(4-Nitro-phenyl)-[1,4]diazepane (4.90 g), Methansulfonyl-ethene (2.35 g) and Methanol (50 mL) was stirred for 2 h at room temperature. The volatiles were removed in vacuo. The product with the molecular weight of 327.40 (C14H21N3O4S) was obtained in this way; MS (ESI): 328 (M+H+).

1-(4-Nitro-phenyl)-[1,4]diazepane 4-(4-Nitro-phenyl)-[1,4]diazepane-1-carboxylic acid tert-butyl ester was reacted by method K. The product with the molecular weight of 221.26 (C11H15N3O2) was obtained in this way; MS (ESI): 222 (M+H+).

4-(4-Nitro-phenyl)-[1,4]diazepane-1-carboxylic acid tert-butyl ester

[1,4]Diazepane-1-carboxylic acid tert-butyl ester was reacted with 1-Fluoro-4-nitro-benzene at 60° C. by method D. The product with the molecular weight of 321.38 (C16H23N3O4) was obtained in this way; MS (ESI): 322 (M+H+).

Example 45

6-Cyclopropylethynyl-3-[4-((R)-3-dimethylamino-pyrrolidin-1-yl)-phenyl]-3H-thieno[3,2-d]pyrimidin-4-one

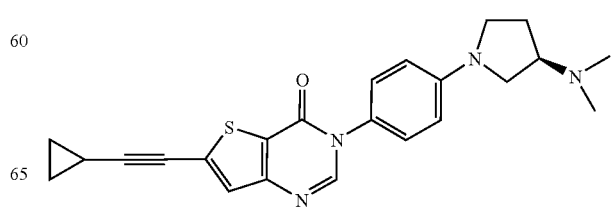

5-Cyclopropylethynyl-3-(dimethylamino-methylene-amino)-thiophene-2-carboxylic acid methyl ester was reacted with [(R)-1-(4-amino-phenyl)-pyrrolidin-3-yl]-dimethylamine by method A1. The product with the molecular weight of 404.53 (C23H24N4OS) was obtained in this way; MS (ESI): 405 (M+H+).

The compounds in table 5 were synthesized analogously.

5-(2-Cyclopropylethyl)-3-(dimethylaminomethylene-amino)thiophene-2-carboxylic acid methyl ester was reacted with [(R)-1-(4-aminophenyl)pyrrolidin-3-yl]-(2-methanesulfonylethyl)methylamine by method A1. The product with the molecular weight of 500.57 (C25H32N4O3S2) was obtained in this way; MS (ESI): 501 (M+H+).

TABLE 5

| Ex. No. | Structure | Molecular formula | Molecular weight | ESI-MS [M + H]+ |
|---|---|---|---|---|
| 46 | 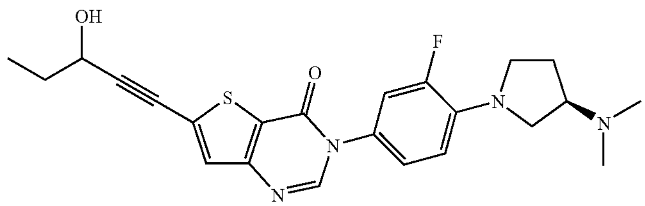 [SMILES: CCC(O)C#Cc1cc2ncn(-c3ccc(N4CC[C@@H](N(C)C)C4)c(F)c3)c(=O)c2s1] | C23H25FN4O2S | 440.54 | 441 |
| 47 | 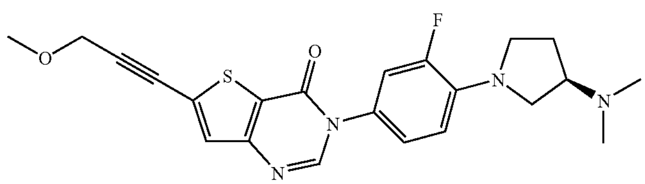 | C22H23FN4O2S | 426.51 | 427 |
| 48 | 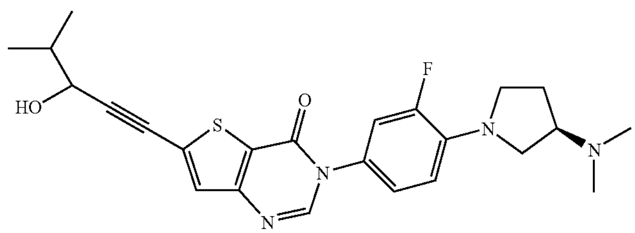 [SMILES: CC(C)C(O)C#Cc1cc2ncn(-c3ccc(N4CC[C@@H](N(C)C)C4)c(F)c3)c(=O)c2s1] | C24H27FN4O2S | 454.56 | 455 |
| 49 | 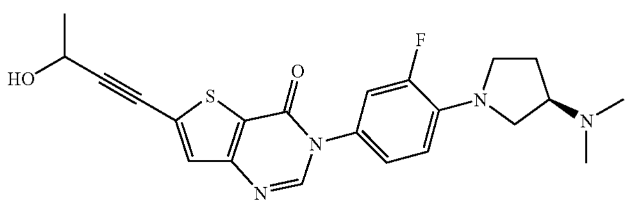 [SMILES: CC(O)C#Cc1cc2ncn(-c3ccc(N4CC[C@@H](N(C)C)C4)c(F)c3)c(=O)c2s1] | C22H23FN4O2S | 426.51 | 427 |

The precursors were obtained from the corresponding alkyne by reaction with 5-Bromo-3-nitrothiophene-2-carboxylic acid methyl ester by method Q and subsequent reduction of the nitro group by method C2 and further reaction by method B (analogous to example 29).

Example 50

6-(2-Cyclopropylethyl)-3-(4-{(R)-3-[(2-methanesulfonylethyl)methylamino]pyrrolidin-1-yl}phenyl)-3H-thieno[3,2-d]pyrimidin-4-one

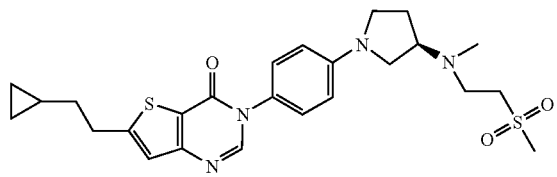 [SMILES: CN(CCS(C)(=O)=O)[C@@H]1CCN(c2ccc(-n3cnc4cc(CCC5CC5)sc4c3=O)cc2)C1]

5-(2-Cyclopropylethyl)-3-dimethylaminomethylene-amino)thiophene-2-carboxylic acid methyl ester 3-Amino-5-(2-cyclopropylethyl)thiophene-2-carboxylic acid methyl ester was reacted by method B. The product with the molecular weight of 280.39 (C14H20N2O2S) was obtained in this way; MS (ESI): 281 (M+H+).

3-Amino-5-(2-cyclopropylethyl)thiophene-2-carboxylic acid methyl ester

Method C3

A suspension of 5-cyclopropylethynyl-3-nitrothiophene-2-carboxylic acid methyl ester (1.0 g) and palladium (5% on carbon) (170 mg) in methanol (50 mL) was vigorously stirred under an atmosphere of hydrogen at atmospheric pressure for 5 h. The catalyst was then filtered off through kieselguhr, and the solvent was removed in vacuo. The product with the molecular weight of 225.31 (C11H15NO2S) was obtained in this way; MS (ESI): 226 (M+H+).

The compounds in table 6 were prepared analogously.

TABLE 6

| Bsp. No. | Structure | Molecular Formula | Molecular Weight | ESI-MS [M + H]+ |
|---|---|---|---|---|
| 51 | 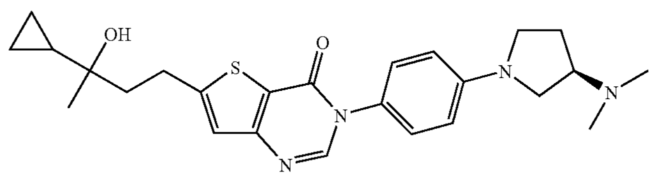 [SMILES: CN(C)[C@@H]1CCN(c2ccc(-n3cnc4cc(CCC(C)(O)C5CC5)sc4c3=O)cc2)C1] | C25H32N4O2S | 452.61 | 453 |
| 52 | 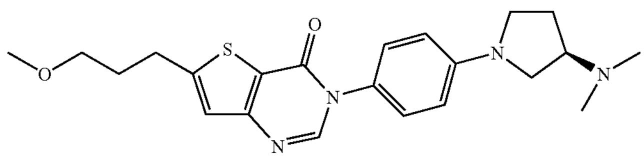 | C22H28N4O2S | 412.55 | 413 |
| 53 | 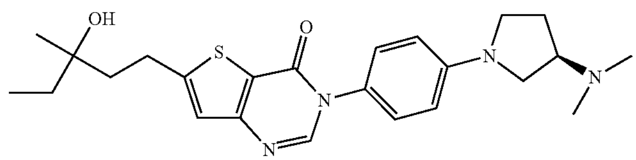 [SMILES: CCC(C)(O)CCc1cc2ncn(-c3ccc(N4CC[C@@H](N(C)C)C4)cc3)c(=O)c2s1] | C24H32N4O2S | 440.60 | 441 |
| 54 | 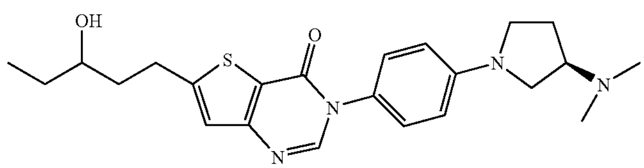 [SMILES: CCC(O)CCc1cc2ncn(-c3ccc(N4CC[C@@H](N(C)C)C4)cc3)c(=O)c2s1] | C23H30N4O2S | 426.58 | 427 |
| 55 | 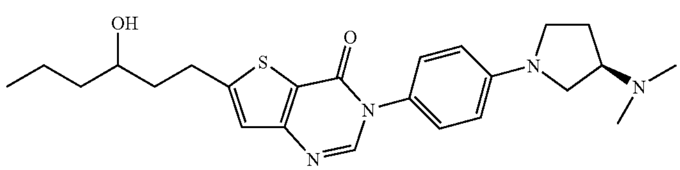 [SMILES: CCCC(O)CCc1cc2ncn(-c3ccc(N4CC[C@@H](N(C)C)C4)cc3)c(=O)c2s1] | C24H32N4O2S | 440.60 | 441 |
| 56 | 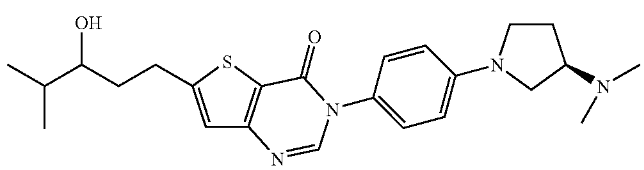 [SMILES: CC(C)C(O)CCc1cc2ncn(-c3ccc(N4CC[C@@H](N(C)C)C4)cc3)c(=O)c2s1] | C24H32N4O2S | 440.60 | 441 |
| 57 | 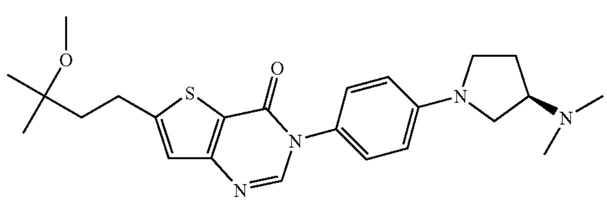 [SMILES: COC(C)(C)CCc1cc2ncn(-c3ccc(N4CC[C@@H](N(C)C)C4)cc3)c(=O)c2s1] | C24H32N4O2S | 440.60 | 441 |
| 58 | 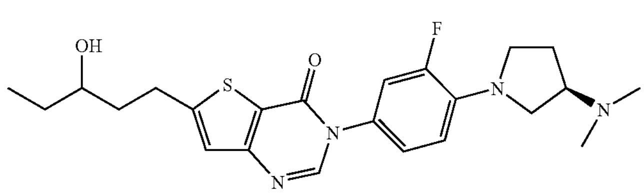 [SMILES: CCC(O)CCc1cc2ncn(-c3ccc(N4CC[C@@H](N(C)C)C4)c(F)c3)c(=O)c2s1] | C23H29FN4O2S | 444.57 | 445 |

TABLE 6-continued

| Bsp. No. | Structure | Molecular Formula | Molecular Weight | ESI-MS [M + H]+ |
|---|---|---|---|---|
| 59 | 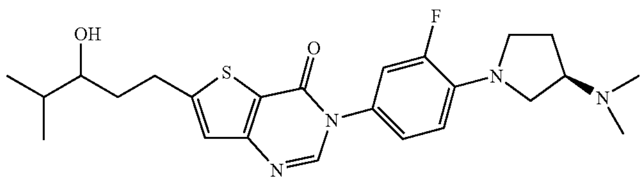 [SMILES: CC(C)C(O)CCc1cc2ncn(-c3ccc(N4CC[C@@H](N(C)C)C4)c(F)c3)c(=O)c2s1] | C24H31FN4O2S | 458.59 | 459 |
| 60 | 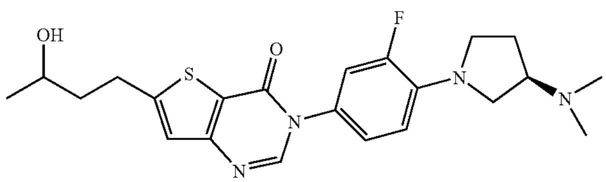 [SMILES: CC(O)CCc1cc2ncn(-c3ccc(N4CC[C@@H](N(C)C)C4)c(F)c3)c(=O)c2s1] | C22H27FN4O2S | 430.54 | 431 |
| 61 | 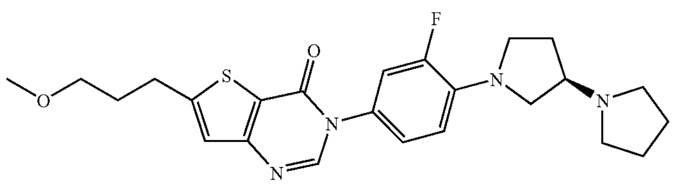 [SMILES: COCCCc1cc2ncn(-c3ccc(N4CC[C@@H](N5CCCC5)C4)c(F)c3)c(=O)c2s1] | C24H29FN4O2S | 456.58 | 457 |
| 62 | 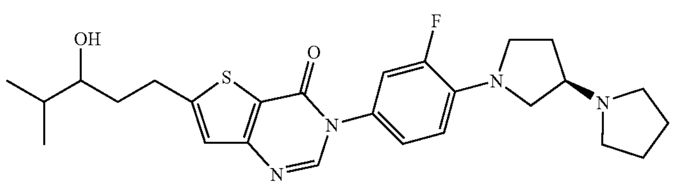 [SMILES: CC(C)C(O)CCc1cc2ncn(-c3ccc(N4CC[C@@H](N5CCCC5)C4)c(F)c3)c(=O)c2s1] | C26H33FN4O2S | 484.63 | 485 |
| 63 | 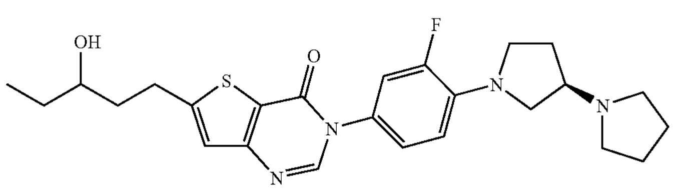 [SMILES: CCC(O)CCc1cc2ncn(-c3ccc(N4CC[C@@H](N5CCCC5)C4)c(F)c3)c(=O)c2s1] | C25H31FN4O2S | 470.61 | 471 |
| 64 | 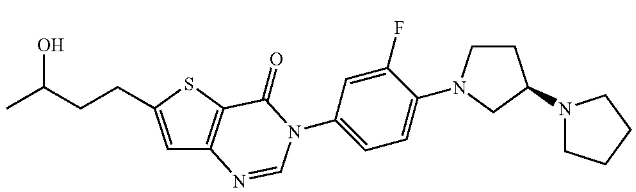 [SMILES: CC(O)CCc1cc2ncn(-c3ccc(N4CC[C@@H](N5CCCC5)C4)c(F)c3)c(=O)c2s1] | C24H29FN4O2S | 456.58 | 457 |

The precursors were obtained from the corresponding alkyne by reaction with 5-Bromo-3-nitrothiophene-2-carboxylic acid methyl ester by method Q and subsequent reduction of the nitro group by method C3 and further reaction by method B (analogous to example 50).

Example 65

3-[4-((R)-3-Dimethylaminopyrrolidin-1-yl)phenyl]-6-piperidin-1-yl-3H-thieno[3,2-d]pyrimidin-4-one

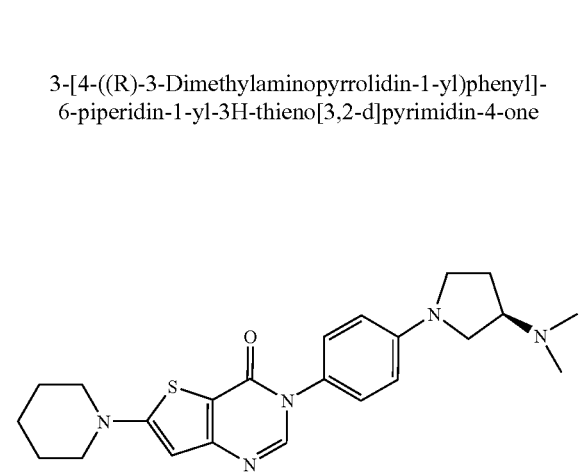

A mixture of 6-bromo-3-[4-((R)-3-dimethylaminopyrrolidin-1-yl)phenyl]-3H-thieno[3,2-d]pyrimidin-4-one (40 mg) and piperidine (492 mg) was heated at 100° C. for 2 days. Water and ethyl acetate were then added, and the organic phase was washed twice with water. The ethyl acetate phase was dried over sodium sulfate and the solvent was removed in vacuo. The residue was purified by preparative HPLC. The product with the molecular weight of 423.58 (C23H29N5OS) was obtained in this way; MS (ESI): 424 (M+H+).

Example 66

3-[4-(4-Methyl[1,4]diazepan-1-yl)phenyl]-6-(2-oxopyrrolidin-1-yl)-3H-thieno[3,2-d]pyrimidin-4-one

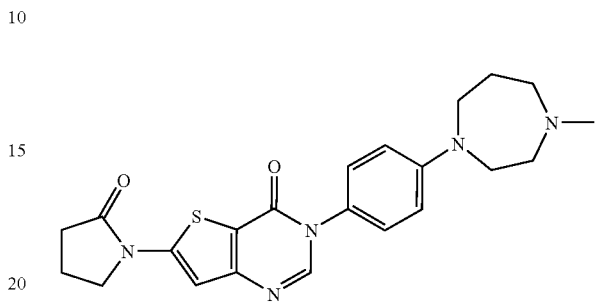

Method R

A mixture of 6-bromo-3-[4-(4-methyl[1,4]diazepan-1-yl)phenyl]-3H-thieno[3,2-d]pyrimidin-4-one (100 mg), cesium carbonate (116.6 mg) and tri(dibenzylideneacetone)dipalladium(0)-chloroform adduct (0.25 mg) was introduced into a heat-dried vessel in a glove box. 2-pyrrolidone (24.4 mg), 9,9-dimethyl-4,5-bis(diphenylphoshino)xanthene (0.27 mg) in dioxane (2.5 mL) were added thereto. The reaction was stirred at 100° C. for 22 h. The resulting precipitate was then filtered off. The product with the molecular weight of 423.53 (C22H25N5O2S) was obtained in this way; MS (ESI): 424 (M+H+).

The compounds in table 7 were synthesized analogously.

TABLE 7

| Ex. No. | Structure | Molecular formula | Molecular weight | ESI-MS [M + H]+ |
|---|---|---|---|---|
| 67 | 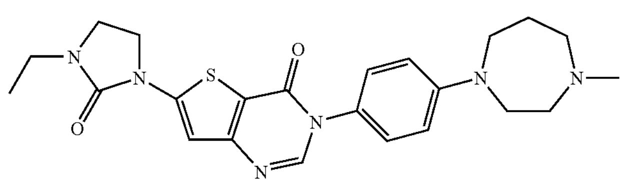 [SMILES: CCN1CCN(c2cc3ncn(-c4ccc(N5CCCN(C)CC5)cc4)c(=O)c3s2)C1=O] | C23H28N6O2S | 452.57 | 453 |
| 68 | 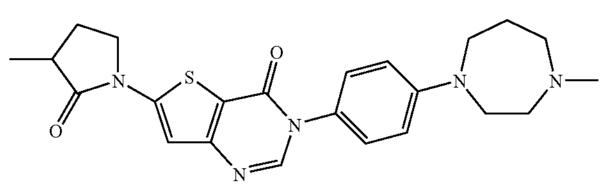 | C23H27N5O2S | 437.56 | 438 |

1-Ethyl-imidazolidin-2-one

1-Ethyl-1,3-dihydro-imidazol-2-one was hydrogenated by method C1. The product with the molecular weight of 114.15 (C5H10N2O) was obtained in this way; MS (ESI): 115 (M+H+).

1-Ethyl-1,3-dihydro-imidazol-2-one was obtained according to reference: O. Wong et al., Heterocycles 1987, 26(12), 3153-8.

Example 69

3-[4-(4-Methylperhydro-1,4-diazepin-1-yl)phenyl]-6-(pyrrolidine-1-carbonyl)-3H-thieno[3,2-d]pyrimidin-4-one

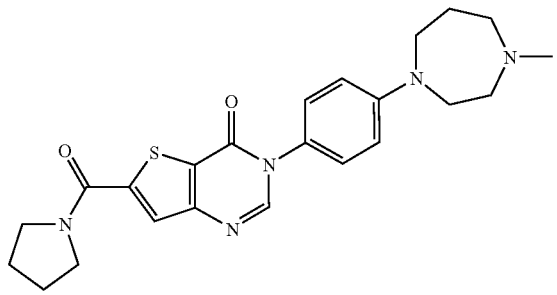 [SMILES: CN1CCCN(c2ccc(-n3cnc4cc(C(=O)N5CCCC5)sc4c3=O)cc2)CC1]

Method S

HATU (39.9 mg), HOAt (13.6 mg) and triethylamine (0.028 mL) were added to a mixture of 3-[4-(4-methylperhydro-1,4-diazepin-1-yl)phenyl]-4-oxo-3,4-dihydrothieno[3,2-d]pyrimidine-6-carboxylic acid (38.5 mg) and pyrrolidine (7.2 mg) in NMP (1 mL). The reaction mixture was stirred at room temperature overnight. The mixture was then mixed with ethyl acetate and water. The aqueous phase was extracted several times with ethyl acetate. The combined organic phases were dried over sodium sulfate and the solvent was removed in vacuo. The crude product was purified by preparative HPLC. The product with the molecular weight of 437.56 (C23H27N5O2S) was obtained in this way; MS (ESI): 438 (M+H+).

3-[4-(4-Methylperhydro-1,4-diazepin-1-yl)phenyl]-4-oxo-3,4-dihydrothieno[3,2-d]-pyrimidine-6-carboxylic acid Method T A 2M LiOH solution (1.2 mL) was added to a solution of 3-[4-(4-methylperhydro-1,4-diazepin-1-yl)phenyl]-4-oxo-3,4-dihydrothieno[3,2-d]pyrimidine-6-carboxylic acid methyl ester (477.8 mg) in THF (5 mL) and water (5 mL), and the mixture was stirred at room temperature for 5 h. The solvent was then removed in vacuo and the crude product was purified by preparative HPLC. The product with the molecular weight of 384.45 (C19H20N4O3S) was obtained in this way; MS (ESI): 385 (M+H+).

3-[4-(4-Methylperhydro-1,4-diazepin-1-yl)phenyl]-4-oxo-3,4-dihydrothieno[3,2-d]-pyrimidine-6-carboxylic acid methyl ester Method U Bis(triphenylphosphine)palladium(II) chloride (84.2 mg) and triethylamine (0.25 mL) were added to a mixture of 6-bromo-3-[4-(4-methylperhydro-1,4-diazepin-1-yl)phenyl]-3H-thieno[3,2-d]pyrimidin-4-one (503.2 mg) in methanol (15 mL) and acetonitrile (15 mL). The reaction mixture was stirred under a pressure of 5 bar of CO at 60° C. for 24 h. The reaction mixture was then filtered off through Celite and the solvent was removed in vacuo. The crude product was purified by preparative HPLC. The product with the molecular weight of 398.48 (C20H22N4O3S) was obtained in this way; MS (ESI): 399 (M+H+).

The examples in table 8 were prepared analogously.

TABLE 8

| Ex. No. | Structure | Molecular formula | Molecular weight | ESI-MS [M + H]+ |
|---|---|---|---|---|
| 70 | 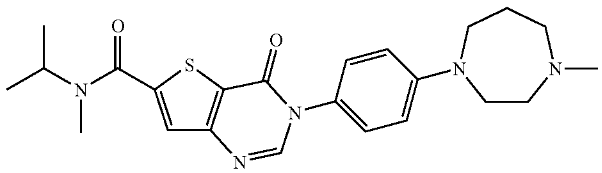 [SMILES: CC(C)N(C)C(=O)c1cc2ncn(-c3ccc(N4CCCN(C)CC4)cc3)c(=O)c2s1] | C23H29N5O2S | 439.58 | 440 |
| 71 | 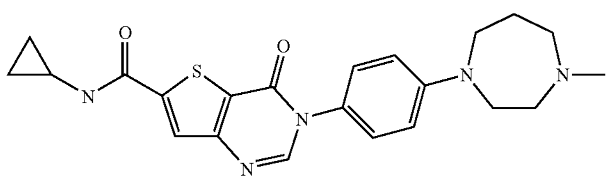 [SMILES: CN1CCCN(c2ccc(-n3cnc4cc(C(=O)NC5CC5)sc4c3=O)cc2)CC1] | C22H25N5O2S | 423.53 | 424 |
| 72 | 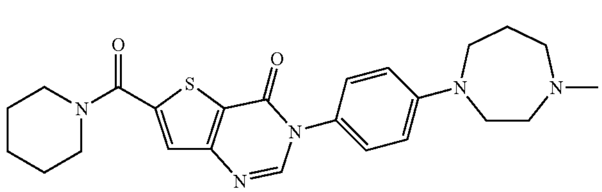 [SMILES: CN1CCCN(c2ccc(-n3cnc4cc(C(=O)N5CCCCC5)sc4c3=O)cc2)CC1] | C24H29N5O2S | 451.59 | 452 |

TABLE 8-continued

| Ex. No. | Structure | Molecular formula | Molecular weight | ESI-MS [M + H]+ |
|---|---|---|---|---|
| 73 | 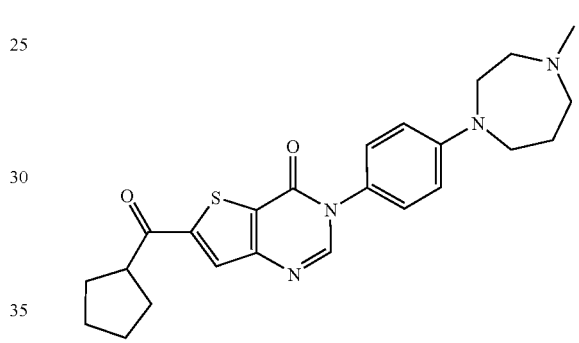 | C23H27N5O3S | 453.56 | 454 |

Example 74

6-((Z)-2-Ethoxyvinyl)-3-[4-(4-methyl[1,4]diazepan-1-yl)phenyl]-3H-thieno[3,2-d]pyrimidin-4-one

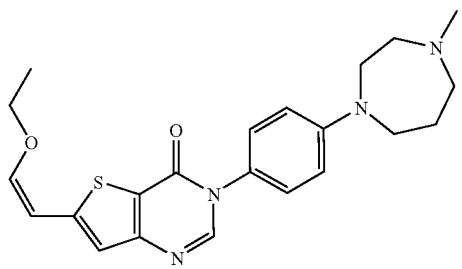 [SMILES: CCO/C=C\c1cc2ncn(-c3ccc(N4CCCN(C)CC4)cc3)c(=O)c2s1]

Method V

A solution of ethoxyethyne (85 mg) and tributyltin hydride (236 mg) in n-heptane (2 mL) was stirred at 80° C. for 5 h. The solution was concentrated. 6-Bromo-3-[4-(4-methyl[1,4]diazepan-1-yl)phenyl]-3H-thieno[3,2-d]pyrimidin-4-one (85 mg), tetrakis(triphenylphosphone)palladium(0) (12 mg) and DMF (1 mL) were added, and the mixture was stirred at 80° C. for 2 h. The solvent was removed. The crude product was purified by preparative HPLC. The product with the molecular weight of 410.54 (C22H26N4O2S.C2HF3O2) was obtained in this way; MS (ESI): 411 (M+H+).

Example 75

6-(2-Ethoxyethyl)-3-[4-(4-methyl[1,4]diazepan-1-yl)phenyl]-3H-thieno[3,2-d]pyrimidin-4-one

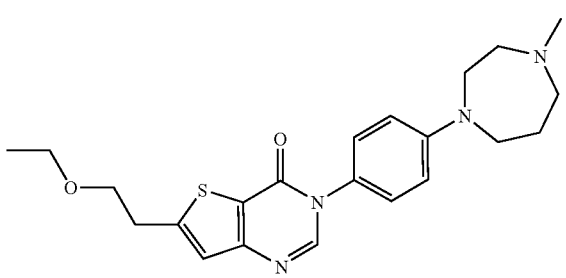 [SMILES: CCOCCc1cc2ncn(-c3ccc(N4CCCN(C)CC4)cc3)c(=O)c2s1]

6-((Z)-2-Ethoxyvinyl)-3-[4-(4-methyl[1,4]diazepan-1-yl)phenyl]-3H-thieno[3,2-d]pyrimidin-4-one was reduced by method C1. The product with the molecular weight of 412.56 (C22H28N4O2S) was obtained in this way; MS (ESI): 413 (M+H+).

Example 76

6-Cyclopentanecarbonyl-3-[4-(4-methyl[1,4]diazepan-1-yl)phenyl]-3H-thieno[3,2-d]pyrimidin-4-one 5-Cyclopentanecarbonyl-3-(dimethylaminomethyleneamino)thiophene-2-carboxylic acid methyl ester and 4-(4-methyl[1,4]diazepan-1-yl)phenylamine were reacted by method A1. The product with the molecular weight of 436.58 (C24H28N4O2S) was obtained in this way; MS (ESI): 437 (M+H+).

5-Cyclopentanecarbonyl-3-(dimethylaminomethyleneamino)thiophene-2-carboxylic acid methyl ester 3-Amino-5-cyclopentanecarbonylthiophene-2-carboxylic acid methyl ester and dimethoxymethyldimethylamine were reacted by method B. The product with the molecular weight of 308.40 (C15H20N2O3S) was obtained in this way; MS (ESI): 309 (14+H+).

3-Amino-5-cyclopentanecarbonylthiophene-2-carboxylic acid methyl ester

Method X

Potassium carbonate (2.275 g) was added to a solution of 5-cyclopentanecarbonyl-3-(2,2,2-trifluoroacetylamino)thiophene-2-carboxylic acid methyl ester (1.150 g) in methanol (17 mL), and the mixture was stirred at room temperature for 2 h. Water and ethyl acetate were added. The organic phase was separated off, and the aqueous phase was re-extracted twice with ethyl acetate. The combined organic phases were dried over magnesium sulfate and concentrated. The product with the molecular weight of 253.32 (C12H15NO3S) was obtained in this way; MS (ESI): 254 (M+H+).

5-Cyclopentanecarbonyl-3-(2,2,2-trifluoroacetylamino)thiophene-2-carboxylic acid methyl ester 3-(2,2,2-Trifluoroacetylamino)thiophene-2-carboxylic acid methyl ester and cyclopentanecarboxylic acid methoxymethylamide were reacted by method M. The product with the molecular weight of 349.33 (C14H14F3NO4S) was obtained in this way; MS (ESI): 350 (M+H+).

Example 77

6-(Cyclopentylhydroxymethyl)-3-[4-(4-methyl[1,4]diazepan-1-yl)phenyl]-3H-thieno[3,2-d]-pyrimidin-4-one

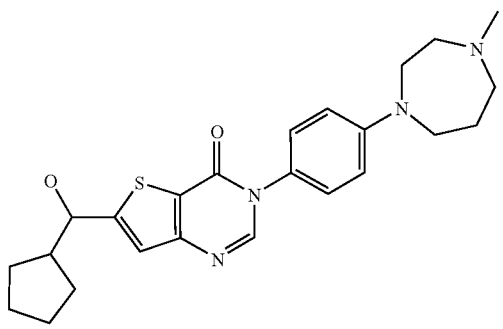 [SMILES: CN1CCCN(c2ccc(-n3cnc4cc(C(O)C5CCCC5)sc4c3=O)cc2)CC1]

Method Y

Sodium borohydride (100 mg) was added in portions to a solution of 6-cyclopentanecarbonyl-3-[4-(4-methyl[1,4]diazepan-1-yl)phenyl]-3H-thieno[3,2-d]pyrimidin-4-one (180 mg) in methanol (30 mL). After 1 h, methanol (150 mL) was added, and the solvent was removed in vacuo. Sodium bicarbonate solution and dichloromethane were added. The organic phase was separated off, and the aqueous phase was re-extracted twice with dichloromethane. The combined organic phases were dried over magnesium sulfate and concentrated. The crude product was purified by preparative HPLC. The product with the molecular weight of 438.60 (C24H30N4O2S) was obtained in this way; MS (ESI): 439 (M+H+).

Example 78

3-[4-(4-Methyl[1,4]diazepan-1-yl)phenyl]-6-(tetrahydropyran-4-carbonyl)-3H-thieno[3,2-d]pyrimidin-4-one

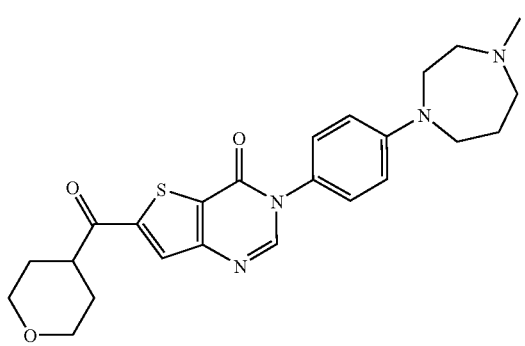 [SMILES: CN1CCCN(c2ccc(-n3cnc4cc(C(=O)C5CCOCC5)sc4c3=O)cc2)CC1]

3-(Dimethylaminomethyleneamino)-5-(tetrahydropyran-4-carbonyl)thiophene-2-carboxylic acid methyl ester and 4-(4-methyl[1,4]diazepan-1-yl)phenylamine were reacted by method A1. The product with the molecular weight of 452.58 (C24H28N4O3S) was obtained in this way; MS (EST): 453 (M+H+).

3-(Dimethylaminomethyleneamino)-5-(tetrahydropyran-4-carbonyl)thiophene-2-carboxylic acid methyl ester 3-Amino-5-(tetrahydropyran-4-carbonyl)thiophene-2-carboxylic acid methyl ester and dimethoxymethyldimethylamine were reacted by method B. The product with the molecular weight of 324.40 (C15H20N2O4S) was obtained in this way; MS (ESI): 325 (M+H+).

3-Amino-5-(tetrahydropyran-4-carbonyl)thiophene-2-carboxylic acid methyl ester 5-(Tetrahydropyran-4-carbonyl)-3-(2,2,2-trifluoroacetylamino)thiophene-2-carboxylic acid methyl ester and potassium carbonate were reacted by method X. The product with the molecular weight of 269.32 (C12H15NO4S) was obtained in this way; MS (ESI): 270 (M+H+).

5-(Tetrahydropyran-4-carbonyl)-3-(2,2,2-trifluoroacetylamino)thiophene-2-carboxylic acid methyl ester 3-(2,2,2-Trifluoroacetylamino)thiophene-2-carboxylic acid methyl ester and tetrahydropyran-4-carboxylic acid methoxymethylamide were reacted by method M. The product with the molecular weight of 365.33 (C14H14F3NO5S) was obtained in this way; MS (ESI): 366 (M+H+).

Example 79

3-[4-(4-Methyl[1,4]diazepan-1-yl)phenyl]-6-vinyl-3H-thieno[3,2-d]pyrimidin-4-one

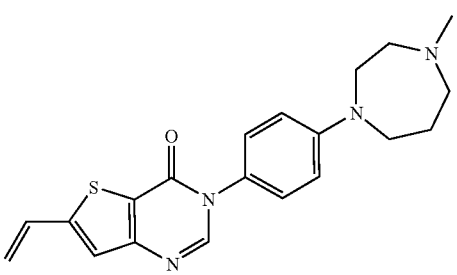 [SMILES: C=Cc1cc2ncn(-c3ccc(N4CCCN(C)CC4)cc3)c(=O)c2s1]

Method Z

A solution of 6-bromo-3-[4-(4-methyl[1,4]diazepan-1-yl)phenyl]-3H-thieno[3,2-d]pyrimidin-4-one (300 mg), vinyltributyltin (339 mg) and tetrakis(triphenylphosphone)palladium(0) (41 mg) in DMF (2 mL) was stirred at 80° C. for 30 min. The reaction solution was then mixed with ethyl acetate and water. The aqueous phase was extracted several times with ethyl acetate. The combined organic phases were dried over magnesium sulfate and concentrated. The crude product was purified by preparative HPLC. The product with the

Example 80

6-(4-Hydroxytetrahydropyran-4-yl)-3-[4-(4-methyl[1,4]diazepan-1-yl)phenyl]-3H-thieno[3,2-d]pyrimidin-4-one

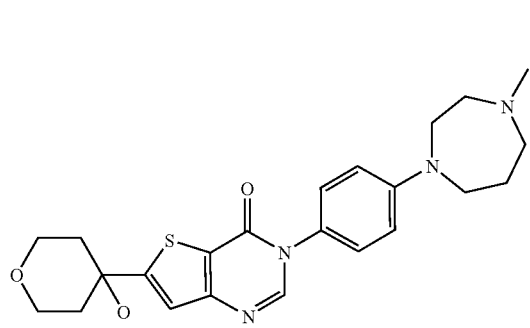 [SMILES: CN1CCCN(c2ccc(-n3cnc4cc(C5(O)CCOCC5)sc4c3=O)cc2)CC1]

3-(Dimethylaminomethyleneamino)-5-(4-hydroxytetrahydropyran-4-yl)thiophene-2-carboxylic acid methyl ester and 4-(4-methyl[1,4]diazepan-1-yl)phenylamine were reacted by method A1. The product with the molecular weight of 440.57 (C23H28N4O3S) was obtained in this way; MS (EST): 441 (M+H+).

3-(Dimethylaminomethyleneamino)-5-(4-hydroxytetrahydropyran-4-yl)thiophene-2-carboxylic acid methyl ester 3-Amino-5-(4-hydroxytetrahydropyran-4-yl)thiophene-2-carboxylic acid methyl ester and dimethoxymethyldimethylamine were reacted by method B. The product with the molecular weight of 312.39 (C14H20N2O4S) was obtained in this way; MS (ESI): 313 (+H+).

3-Amino-5-(4-hydroxytetrahydropyran-4-yl)thiophene-2-carboxylic acid methyl ester 5-(Tetrahydropyran-4-carbonyl)-3-(2,2,2-trifluoroacetylamino)thiophene-2-carboxylic acid methyl ester and potassium carbonate were reacted by method X. The product with the molecular weight of 257.31 (C11H15NO4S) was obtained in this way; MS (ESI): 258 (M+H+).

5-(Tetrahydropyran-4-carbonyl)-3-(2,2,2-trifluoroacetylamino)thiophene-2-carboxylic acid methyl ester 3-(2,2,2-Trifluoroacetylamino)thiophene-2-carboxylic acid methyl ester and tetrahydropyranone were reacted by method M. The product with the molecular weight of 353.32 (C13H14F3NO5S) was obtained in this way; MS (ESI): 354 (M+H+).

Example 81

6-(3-Hydroxy-2-methyltetrahydrofuran-3-yl)-3-[4-(4-methyl[1,4]diazepan-1-yl)phenyl]-3H-thieno[3,2-d]pyrimidin-4-one

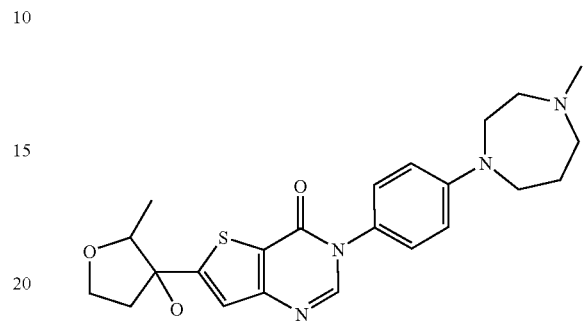

3-(Dimethylaminomethyleneamino)-5-(3-hydroxy-2-methyltetrahydrofuran-3-yl)thiophene-2-carboxylic acid methyl ester and 4-(4-methyl[1,4]diazepan-1-yl)phenylamine were reacted by method A1. The product with the molecular weight of 440.57 (C23H28N4O3S) was obtained in this way; MS (ESI): 441 (M+H+).

3-(Dimethylaminomethyleneamino)-5-(3-hydroxy-2-methyltetrahydrofuran-3-yl)thiophene-2-carboxylic acid methyl ester 3-Amino-5-(3-hydroxy-2-methyltetrahydrofuran-3-yl)thiophene-2-carboxylic acid methyl ester and dimethoxymethyldimethylamine were reacted by method B. The product with the molecular weight of 312.39 (C14H20N2O4S) was obtained in this way; MS (ESI): 313 (M+H+).

3-Amino-5-(3-hydroxy-2-methyltetrahydrofuran-3-yl)thiophene-2-carboxylic acid methyl ester 5-(3-Hydroxy-2-methyltetrahydrofuran-3-yl)-3-(2,2,2-trifluoroacetylamino)thiophene-2-5 carboxylic acid methyl ester and potassium carbonate were reacted by method X. The product with the molecular weight of 257.31 (C11H15NO4S) was obtained in this way; MS (ESI): 258 (M+H+).

5-(3-Hydroxy-2-methyltetrahydrofuran-3-yl)-3-(2,2,2-trifluoroacetylamino)thiophene-2-carboxylic acid methyl ester 3-(2,2,2-Trifluoroacetylamino)thiophene-2-carboxylic acid methyl ester and 2-methyldihydrofuran-3-one were reacted by method M. The product with the molecular weight of 353.32 (C13H14F3NO5S) was obtained in this way; MS (ESI): 354 (M+H+).

--- molecular weight of 366.49 (C20H22N4OS) was obtained in this way; MS (ESI): 367 (M+H+).

Example 82

6-[Hydroxy(tetrahydropyran-4-yl)methyl]-3-[4-(4-methyl[1,4]diazepan-1-yl)phenyl]-3H-thieno[3,2-d]pyrimidin-4-one

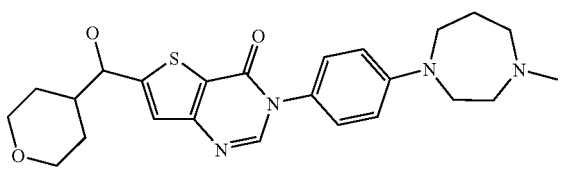 [SMILES: CN1CCCN(c2ccc(-n3cnc4cc(C(O)C5CCOCC5)sc4c3=O)cc2)CC1]

3-[4-(4-Methyl[1,4]diazepan-1-yl)phenyl]-6-(tetrahydro-pyran-4-carbonyl)-3H-thieno[3,2-d]pyrimidin-4-one and sodium borohydride were reacted by method Y. The product with the molecular weight of 454.60 (C24H30N4O3S) was obtained in this way; MS (ESI): 455 (M+H+).

Example 83

6-Isobutyryl-3-[4-(4-methyl[1,4]diazepan-1-yl)phenyl]-3H-thieno[3,2-d]pyrimidin-4-one

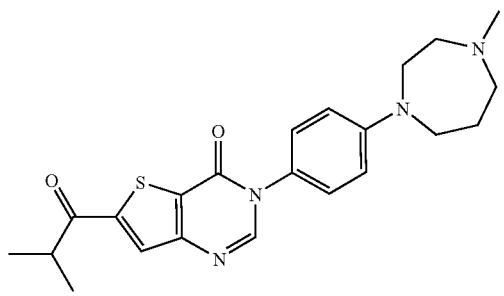 [SMILES: CC(C)C(=O)c1cc2ncn(-c3ccc(N4CCCN(C)CC4)cc3)c(=O)c2s1]

3-(Dimethylaminomethyleneamino)-5-isobutyrylthiophene-2-carboxylic acid methyl ester and 4-(4-methyl[1,4]diazepan-1-yl)phenylamine were reacted by method A1. The product with the molecular weight of 410.54 (C22H26N4O2S) was obtained in this way; MS (ESI): 411 (M+H+).

3-(Dimethylaminomethyleneamino)-5-isobutyrylthiophene-2-carboxylic acid methyl ester 3-Amino-5-isobutyrylthiophene-2-carboxylic acid methyl ester and dimethoxymethyldimethylamine were reacted by method B. The product with the molecular weight of 382.36 (C13H18N2O3S) was obtained in this way; MS (ESI): 383 (M+H+).

3-Amino-5-isobutyrylthiophene-2-carboxylic acid methyl ester

5-Isobutyryl-3-(2,2,2-trifluoroacetylamino)thiophene-2-carboxylic acid methyl ester and potassium carbonate were reacted by method X. The product with the molecular weight of 227.28 (C10H13NO3S) was obtained in this way; MS (ESI): 228 (M+H+).

5-Isobutyryl-3-(2,2,2-trifluoroacetylamino)thiophene-2-carboxylic acid methyl ester 3-(2,2,2-Trifluoroacetylamino)thiophene-2-carboxylic acid methyl ester and N-methoxy-N-methylisobutyramide were reacted by method M. The product with the molecular weight of 323.29 (C12H12F3NO4S) was obtained in this way; MS (ESI): 324 (M+H+).

Example 84

6-(1-Hydroxy-2-methylpropyl)-3-[4-(4-methyl[1,4]diazepan-1-yl)phenyl]-3H-thieno[3,2-d]pyrimidin-4-one

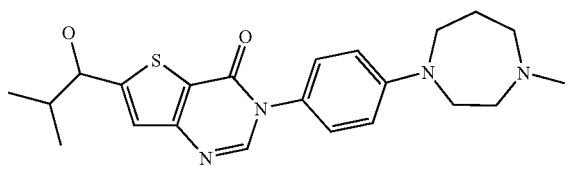 [SMILES: CC(C)C(O)c1cc2ncn(-c3ccc(N4CCCN(C)CC4)cc3)c(=O)c2s1]

6-Isobutyryl-3-[4-(4-methyl[1,4]diazepan-1-yl)phenyl]-3H-thieno[3,2-d]pyrimidin-4-one and sodium borohydride were reacted by method Y. The product with the molecular weight of 412.56 (C22H28N4O2S) was obtained in this way; MS (ESI): 411 (M+H+).

Example 85

3-[4-(4-Methyl[1,4]diazepan-1-yl)phenyl]-6-(tetrahydro-pyran-4-ylidenemethyl)-3H-thieno[3,2-d]pyrimidin-4-one

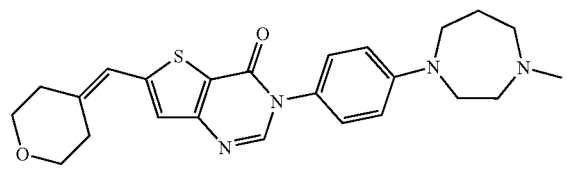

Method AA p-Toluenesulfonic acid (200 mg) was added to a suspension of 6-[hydroxy(tetrahydropyran-4-yl)methyl]-3-[4-(4-methyl[1,4]diazepan-1-yl)phenyl]-3H-thieno[3,2-d]pyrimidin-4-one (114 mg) in toluene (5 mL), and the mixture was heated to reflux for 30 h. After cooling, 1N NaOH (50 mL) was added and the mixture was extracted with dichloromethane and dried over magnesium sulfate. The crude product was purified by preparative HPLC. The product with the molecular weight of 436.58 (C24H28N4O2S) was obtained in this way; MS (ESI): 437 (N+H+).

Example 86

3-[4-(4-Methyl[1,4]diazepan-1-yl)phenyl]-6-(tetrahydropyran-4-ylmethyl)-3H-thieno[3,2-d]pyrimidin-4-one

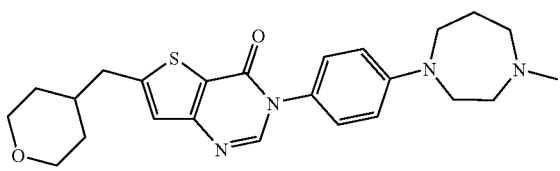

3-[4-(4-Methyl[1,4]diazepan-1-yl)phenyl]-6-(tetrahydropyran-4-ylidenemethyl)-3H-thieno[3,2-d]pyrimidin-4-one was reduced by method C1. The product with the molecular weight of 438.60 (C24H30N4O2S) was obtained in this way; MS (ESI): 439 (M+H+).

Example 87

3-[4-(4-Methyl[1,4]diazepan-1-yl)phenyl]-6-(2-methyl-2,5-dihydrofuran-3-yl)-3H-thieno[3,2-d]pyrimidin-4-one

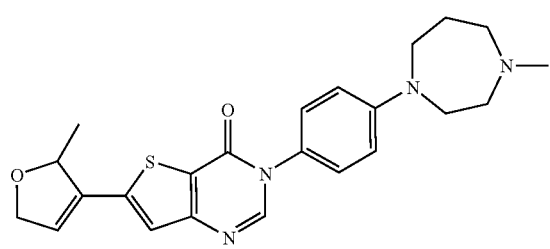 [SMILES: CC1OCC=C1c1cc2ncn(-c3ccc(N4CCCN(C)CC4)cc3)c(=O)c2s1]

6-(3-Hydroxy-2-methyltetrahydrofuran-3-yl)-3-[4-(4-methyl[1,4]diazepan-1-yl)phenyl]-3H-thieno[3,2-d]pyrimidin-4-one and p-toluenesulfonic acid were reacted by method AA. The product with the molecular weight of 422.55 (C23H26N4O2S) was obtained in this way; MS (ESI): 423 (M+H+).

Example 88

3-[4-(4-Methyl[1,4]diazepan-1-yl)phenyl]-6-(2-methyl-4,5-dihydrofuran-3-yl)-3H-thieno[3,2-d]pyrimidin-4-one

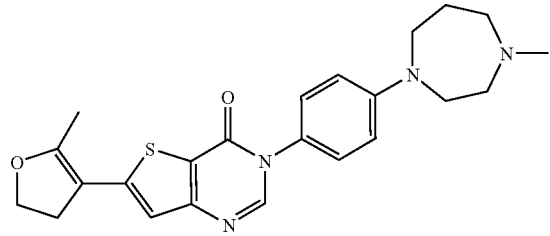 [SMILES: CC1=C(c2cc3ncn(-c4ccc(N5CCCN(C)CC5)cc4)c(=O)c3s2)CCO1]

6-(3-Hydroxy-2-methyltetrahydrofuran-3-yl)-3-[4-(4-methyl[1,4]diazepan-1-yl)phenyl]-3H-thieno[3,2-d]pyrimidin-4-one and p-toluenesulfonic acid were reacted by method AA. The product with the molecular weight of 422.55 (C23H26N4O2S) was obtained in this way; MS (ESI): 423 (M+H+).

Example 89

6-(3,6-Dihydro-2H-pyran-4-ylmethyl)-3-[4-(4-methyl[1,4]diazepan-1-yl)phenyl]-3H-thieno[3,2-d]pyrimidin-4-one

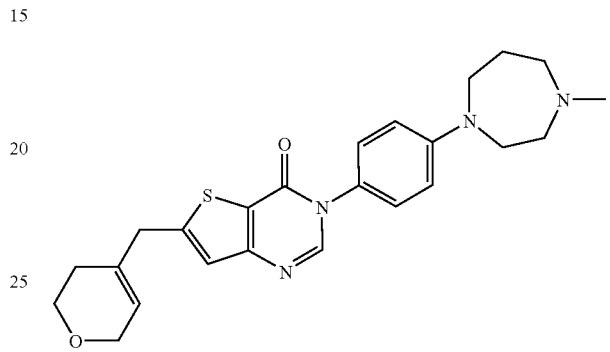

6-[Hydroxy(tetrahydropyran-4-yl)methyl]-3-[4-(4-methyl[1,4]diazepan-1-yl)phenyl]-3H-thieno[3,2-d]pyridin-4-one and p-toluenesulfonic acid were reacted by method AA. The product with the molecular weight of 436.58 (C24H28N4O2S) was obtained in this way; MS (ESI): 437 (M+H+).

Example 90

3-[4-(4-Methyl[1,4]diazepan-1-yl)phenyl]-6-(2-methylpropenyl)-3H-thieno[3,2-d]pyrimidin-4-one

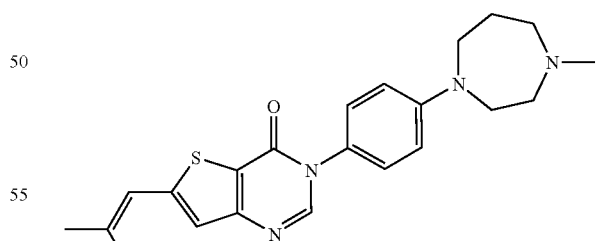

6-(1-Hydroxy-2-methylpropyl)-3-[4-(4-methyl[1,4]diazepan-1-yl)phenyl]-3H-thieno[3,2-d]pyrimidin-4-one and p-toluenesulfonic acid were reacted by method AA. The crude product was purified by preparative HPLC. The product with the molecular weight of 394.54 (C22H26N4OS) was obtained in this way; MS (ESI): 395 (M+H+).

Example 91

6-Isobutyl-3-[4-(4-methyl[1,4]diazepan-1-yl)phenyl]-3H-thieno[3,2-d]pyrimidin-4-one

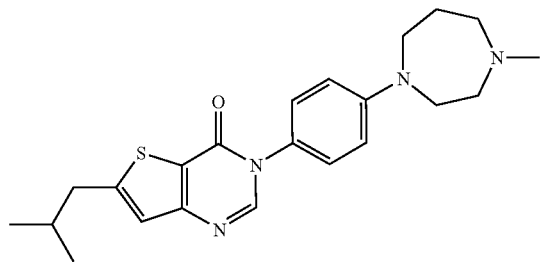 [SMILES: CC(C)Cc1cc2ncn(-c3ccc(N4CCCN(C)CC4)cc3)c(=O)c2s1]

3-[4-(4-Methyl[1,4]diazepan-1-yl)phenyl]-6-(2-methylpropenyl)-3H-thieno[3,2-d]pyrimidin-4-one was reduced by method C1. The product with the molecular weight of 396.56 (C22H28N4OS) was obtained in this way; MS (EST): 397 (M+H+).

Example 92

3-[4-(4-Methyl[1,4]diazepan-1-yl)phenyl]-6-(2-methyltetrahydrofuran-3-yl)-3H-thieno[3,2-d]pyrimidin-4-one

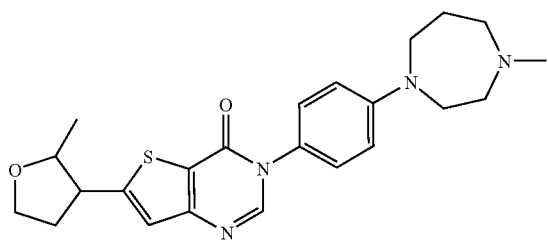

3-[4-(4-Methyl[1,4]diazepan-1-yl)phenyl]-6-(2-methyl-4,5-dihydrofuran-3-yl)-3H-thieno[3,2-d]pyrimidin-4-one was reduced by method C1. The product with the molecular weight of 424.57 (C23H28N4O2S) was obtained in this way; MS (ESI): 425 (M+H+).

Example 93

3-[4-(4-Methylperhydro-1,4-diazepin-1-yl)phenyl]-6-piperidin-1-ylmethyl-3H-thieno[3,2-d]pyrimidin-4-one

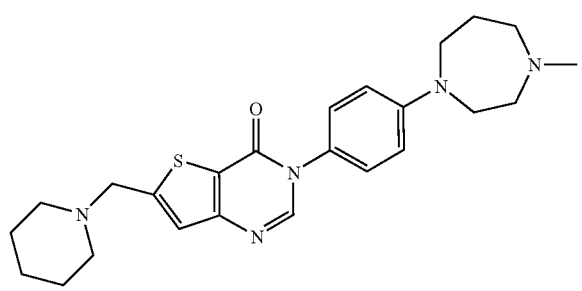 [SMILES: CN1CCCN(c2ccc(-n3cnc4cc(CN5CCCCC5)sc4c3=O)cc2)CC1]

Method BA

Sodium triacetoxyborohydride (143.8 mg) was added to a mixture of 3-[4-(4-methylperhydro-1,4-diazepin-1-yl)phenyl]-4-oxo-3,4-dihydrothieno[3,2-d]pyrimidine-6-carbaldehyde (50 mg) and piperidine (11.6 mg) in methylene chloride (5 mL). The reaction mixture was stirred at room temperature for 2 h. Water was then added. The aqueous phase was extracted several times with methylene chloride. The combined organic phases were dried over sodium sulfate and the solvent was removed in vacuo. The crude product was purified by preparative HPLC. The product with the molecular weight of 437.22 (C24H31N50S) was obtained in this way; MS (ESI): 438 (M+H+).

3-[4-(4-Methylperhydro-1,4-diazepin-1-yl)phenyl]-4-oxo-3,4-dihydrothieno[3,2-d]pyrimidine-6-carbaldehyde 3-(Dimethylaminomethyleneamino)-5-formylthiophene-2-carboxylic acid methyl ester was reacted with 4-(4-methylperhydro-1,4-diazepin-1-yl)phenylamine by method A1. The product with the molecular weight of 368.46 (C19H20N4O2S) was obtained in this way; MS (ESI): 369 (M+H+).

3-(Dimethylaminomethyleneamino)-5-formylthiophene-2-carboxylic acid methyl ester 3-Amino-5-formylthiophene-2-carboxylic acid methyl ester and dimethoxymethyldimethylamine were reacted by method B. The product with the molecular weight of 308.40 (C15H20N2O3S) was obtained in this way; MS (ESI): 309 (M+H+).

3-Amino-5-formylthiophene-2-carboxylic acid methyl ester

5-Formyl-3-(2,2,2-trifluoroacetylamino)thiophene-2-carboxylic acid methyl ester was deblocked by method X. The product with the molecular weight of 185.01 (C7H7NO3S) was obtained in this way; MS (ESI): 186 (M+H+).

5-Formyl-3-(2,2,2-trifluoroacetylamino)thiophene-2-carboxylic acid methyl ester

A 1.6M n-BuLi solution in hexane (12 mL) was added dropwise to a solution of diisopropylamine (2.9 mL) in THF (30 mL) at −78° C. The reaction mixture was stirred at 0° C. for 10 min and then cooled to −78° C., and a solution of 3-(2,2,2-trifluoroacetylamino)thiophene-2-carboxylic acid methyl ester (1.5 g) in THF (15 mL) was added. The reaction mixture was stirred at −78° C. for 30 min and then 1-formylpiperidine (4 g) was added, and the mixture was again stirred at this temperature for 1.5 h. Subsequently, saturated ammonium chloride solution was added and the reaction mixture was allowed to reach room temperature. The aqueous phase was extracted several times with ethyl acetate. The combined organic phases were dried over sodium sulfate and the solvent was removed in vacuo. The product with the molecular weight of 281.0 (C9H6F3NO4S) was obtained in this way; MS (ESI): 282 (M+H+).

The reaction can also be employed with the boc protected compound.

Example 94

3-[4-(4-Methylperhydro-1,4-diazepin-1-yl)phenyl]-6-pyrrolidin-1-ylmethyl-3H-thieno[3,2-d]pyrimidin-4-one

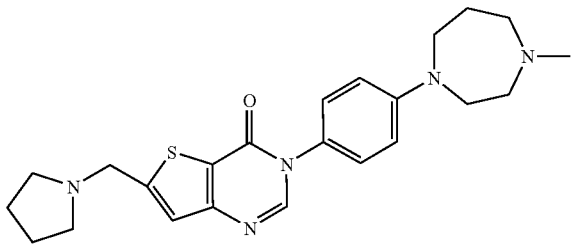 [SMILES: CN1CCCN(c2ccc(-n3cnc4cc(CN5CCCC5)sc4c3=O)cc2)CC1]

3-[4-(4-Methylperhydro-1,4-diazepin-1-yl)phenyl]-4-oxo-3,4-dihydrothieno[3,2-d]pyrimidine-6-carbaldehyde was reacted with pyrrolidine by method BA. The product with the molecular weight of 423.58 (C23H29N5OS) was obtained in this way; MS (ESI): 424 (M+H+).

Example 95

3-[4-(3-Dimethylamino-pyrrolidin-1-yl)-phenyl]-6-propoxymethyl-3H-thieno[3,2-d]pyrimidin-4-one

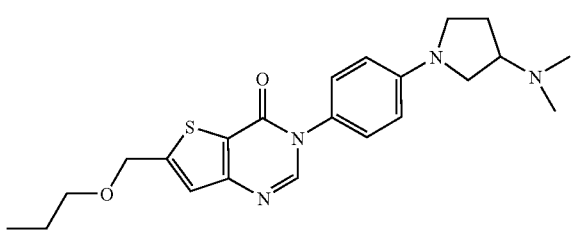 [SMILES: CCCOCc1cc2ncn(-c3ccc(N4CCC(N(C)C)C4)cc3)c(=O)c2s1]

A mixture of 3-[4-(3-Dimethylamino-pyrrolidin-1-yl)-phenyl]-6-hydroxymethyl-3H-thieno[3,2-d]pyrimidin-4-one (50.0 mg), sodium hydride (5.24 mg) and DMF (1 mL) was stirred at 0° C. for 15 min. Then 1-bromopropane (22.0 mg) was added, the solution was warmed to room temperature and stirred for 2 h. Water and ethyl acetate were added and the aqueous phase was extracted with ethyl acetate several times. The combined organic phase was dried over sodium sulfate and the solvent removed in vacuo. The crude product was purified by preparative HPLC. The product with the molecular weight of 412.55 (C22H28N4O2S) was obtained in this way; MS (ESI): 413 (M+H+).

3-[4-(3-Dimethylamino-pyrrolidin-1-yl)-phenyl]-6-hydroxymethyl-3H-thieno[3,2-d]pyrimidin-4-one A mixture of 6-(tert-Butyl-diphenyl-silanyloxymethyl)-3-[4-(3-dimethylamino-pyrrolidin-1-yl)-phenyl]-3H-thieno[3,2-d]pyrimidin-4-one (1.4 g) and 1 M solution of Tetra-N-butylammoniumfluoride in THF (2.7 mL) in THF (20.0 mL) was stirred at room temperature for 3 h. The solvent was removed in vacuo and the crude product was purified by preparative HPLC. The product with the molecular weight of 370.47 (C19H22N4O2S) was obtained in this way; MS (ESI): 371 (M+H+).

6-(tert-Butyl-diphenyl-silanyloxymethyl)-3-[4-(3-dimethylamino-pyrrolidin-1-yl)-phenyl]-3H-thieno[3,2-d]pyrimidin-4-one 5-(tert-Butyl-diphenyl-silanyloxymethyl)-3-(dimethylamino-methyleneamino)-thiophene-2-carboxylic acid methyl ester was reacted with [1-(4-Amino-phenyl)-pyrrolidin-3-yl]-dimethyl-amine by method A1. The product with the molecular weight of 608.87 (C35H40N4O2SSi) was obtained in this way; MS (ESI): 609 (M+H+).

5-(tert-butyl-diphenyl-silanyloxymethyl)-3-(dimethylamino-methyleneamino)-thiophene-2-carboxylic acid methyl ester 3-Amino-5-(tert-butyl-diphenyl-silanyloxymethyl)-thiophene-2-carboxylic acid methyl ester was reacted by method B. The product with the molecular weight of 480.70 (C26H32N2O3SSi) was obtained in this way; MS (ESI): 481 (M+H+).

3-Amino-5-(tert-butyl-diphenyl-silanyloxymethyl)-thiophene-2-carboxylic acid methyl ester 3-tert-butoxycarbonylamino-5-(tert-butyl-diphenyl-silanyloxymethyl)-thiophene-2-carboxylic acid methyl ester was deblocked by method K. The product with the molecular weight of 425.62 (C23H27NO3SSi) was obtained in this way; MS (ESI): 426 (M+H+).

3-tert-Butoxycarbonylamino-5-(tert-butyl-diphenyl-silanyloxymethyl)-thiophene-2-carboxylic acid methyl ester A solution of tert.-butyldiphenylchlorosilane (1.66 g) in methylene chloride (5 mL) was added to a mixture of 3-tert-butoxycarbonylamino-5-hydroxymethyl-thiophene-2-carboxylic acid methyl ester (1.42 g), DIPEA (1.26 mL), DMAP (30.21 mg) and methylene chloride (25 mL) during the course of 10 min. The mixture was stirred for 6 h at room temperature. Methylene chloride was added and washed with saturated ammonium chloride solution and water. The combined organic phases were dried over sodium sulfate and the solvent removed in vacuo. The product with the molecular weight of 525.74 (C28H35NO5SSi) was obtained in this way; MS (ESI): 426 (M–BOC+H+).

3-tert-butoxycarbonylamino-5-hydroxymethyl-thiophene-2-carboxylic acid methyl ester To a suspension of 3-tert-butoxycarbonylamino-5-formyl-thiophene-2-carboxylic acid methyl ester (1.49 g) in ethanol/water (95 mL/95 mL) sodiumborohydride (105.8 mg) was added at 0° C. The mixture was stirred for 1 h at this temperature. Then ethyl acetate and water were added. The aqueous phase was extracted several times with ethyl acetate, the combined organic phases dried over sodium sulfate and the solvent removed in vacuo. The product with the molecular weight of 287.33 (C12H17NO5S) was obtained in this way; MS (ESI): 288 (M+H+).

Example 96

6-Cyclopropylmethoxymethyl-3-[4-(3-dimethylamino-pyrrolidin-1-yl)-phenyl]-3H-thieno[3,2-d]pyrimidin-4-one

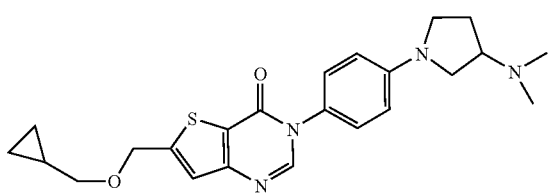 [SMILES: CN(C)C1CCN(c2ccc(-n3cnc4cc(COCC5CC5)sc4c3=O)cc2)C1]

A mixture of 3-[4-(3-dimethylamino-pyrrolidin-1-yl)-phenyl]-6-hydroxymethyl-3H-thieno[3,2-d]pyrimidin-4-one (20.0 mg) and potassium-tert.-butoxide (7.65 mg) in DMF (0.3 mL) was stirred at 0° C. for 5 min. Then cyclopropylmethylbromide (11.28 mg) was added. The solution was warmed to room temperature and stirred for 2 h. Then ethyl acetate and water were added. The aqueous phase was extracted several times with ethyl acetate, the combined organic phases dried over sodium sulfate and the solvent removed in vacuo. The crude product was purified by preparative HPLC. The product with the molecular weight of 424.56 (C23H28N4O2S) was obtained in this way; MS (ESI): 425 (M+H+).

Example 97

6-cyclobutylmethoxymethyl-3-[4-(3-dimethylamino-pyrrolidin-1-yl)-phenyl]-3H-thieno[3,2-d]pyrimidin-4-one

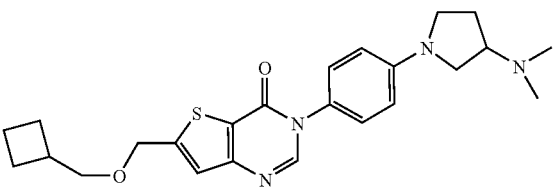 [SMILES: CN(C)C1CCN(c2ccc(-n3cnc4cc(COCC5CCC5)sc4c3=O)cc2)C1]

Example 97 was prepared analogously following the procedures as set forth in example 96 but using (bromomethyl)cyclobutane. The product with the molecular weight of 438.59 (C24H30N4O2S) was obtained in this way; MS (ESI): 439 (M+H+).

Table 9 summarizes the results which were obtained by the above described calcium immobilization assay

TABLE 9

| Ex. No. | IC$_{50}$/μM |
|---|---|
| 26 | 1.10 |
| 30 | 0.38 |
| 32 | 1.35 |
| 38 | 0.44 |
| 39 | 0.92 |
| 40 | 0.66 |
| 42 | 0.18 |
| 44 | 0.74 |
| 45 | 0.11 |
| 47 | 0.23 |

TABLE 9-continued

| Ex. No. | IC$_{50}$/μM |
|---|---|
| 49 | 0.18 |
| 50 | 0.32 |
| 57 | 2.09 |
| 61 | 0.56 |
| 63 | 0.24 |
| 65 | 1.33 |
| 74 | 2.95 |
| 76 | 8.74 |
| 77 | 9.03 |
| 95 | 0.34 |
| 96 | 0.60 |

We claim:
1. A compound of formula I

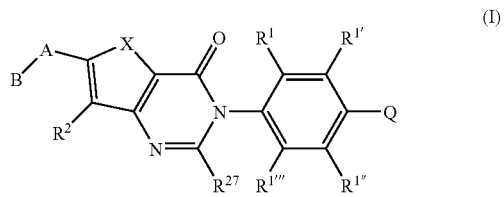

wherein:
$R^1$, $R^{1\prime}$, $R^{1\prime\prime\prime}$ and $R^{1\prime\prime\prime\prime}$ are independently of one another H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, $N(R^3)(R^4)$, $SO_2$—$CH_3$, COOH, COO—($C_1$-$C_6$)-alkyl, $CON(R^5)(R^6)$, $N(R^7)CO(R^8)$, $N(R^9)SO_2(R^{10})$, $CO(R^{11})$, or $(C(R^{12})(R^{13}))_x$—$O(R^{14})$;
$R^3$, $R^4$, $R^5$, $R^6$, $R^7$ and $R^9$ are
independently of one another H, or ($C_1$-$C_8$)-alkyl,
or
$R^3$ and $R^4$, or $R^5$ and $R^6$,
independently of one another taken together with the nitrogen atom to which they are bonded form a 5-6 membered ring which optionally comprises one additional heteroatom selected from the group consisting of NH, N—($C_1$-$C_6$)-alkyl, oxygen and sulfur;
$R^8$, $R^{10}$ and $R^{11}$ are
independently of one another H, or ($C_1$-$C_8$)-alkyl;
$R^{12}$ and $R^{13}$ are
independently of one another H, or ($C_1$-$C_8$)-alkyl;
$R^{14}$ is H, ($C_1$-$C_6$)-alkyl, or aryl;
x is 0, 1, 2, 3, 4, 5, or 6;
$R^2$ is H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, $N(R^{15})(R^{16})$, $SO_2$—$CH_3$, COOH, COO—($C_1$-$C_6$)-alkyl, $CON(R^{17})(R^{18})$, $N(R^{19})CO(R^{20})$, $N(R^{21})SO_2(R^{22})$, $CO(R^{23})$, or $(C(R^{24})(R^{25}))_x$—$O(R^{26})$;
$R^{15}$, $R^{16}$, $R^{17}$, $R^{18}$, $R^{19}$ and $R^{21}$ are
independently of one another H, ($C_1$-$C_8$)-alkyl,
or
$R^{15}$ and $R^{16}$, or $R^{17}$ and $R^{18}$,
independently of one another taken together with the nitrogen atom to which they are bonded form a 5-6 membered ring which optionally comprises one additional heteroatom selected from the group consisting of NH, N—($C_1$-$C_6$)-alkyl, oxygen and sulfur;

$R^{20}$, $R^{22}$ and $R^{23}$ are independently of one another H, or ($C_1$-$C_8$)-alkyl;

$R^{24}$ and $R^{25}$ are independently of one another H, or ($C_1$-$C_8$)-alkyl;

$R^{26}$ is H, ($C_1$-$C_6$)-alkyl, or aryl;

x' is 0, 1, 2, 3, 4, 5, or 6;

$R^{27}$ is H, or ($C_1$-$C_6$)-alkyl;

X is S;

A is a bond or a linker having 1 to 8 members, where the members are selected from the group consisting of O, S, $SO_2$, N($R^{31}$), CO, C($R^{32}$)($R^{33}$), C($R^{34}$)=C($R^{34'}$), cyclopropylene, and C≡C, wherein the linker contains no O—CO or CO—O groups;

$R^{31}$, $R^{34}$ and $R^{34'}$ are independently of one another H, or ($C_1$-$C_8$)-alkyl;

$R^{32}$ and $R^{33}$ are independently of one another H, ($C_1$-$C_6$)-alkyl, OH, or O—($C_1$-$C_6$)-alkyl;

B is N($R^{35}$)($R^{36}$), hydroxy-($C_1$-$C_4$)-alkyl, ($C_1$-$C_8$)-alkyl, ($C_1$-$C_4$)-alkoxy-($C_1$-$C_4$)-alkyl, ($C_2$-$C_8$)-alkenyl, ($C_2$-$C_8$)-alkynyl, or a 3 to 10-membered mono-, bi-, tri- or spirocyclic nonaromatic ring which optionally comprises 0 to 4 heteroatoms selected from the group consisting of oxygen, nitrogen and sulfur, where the ring system is also optionally substituted one or more times by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO($R^{37}$), CON($R^{38}$)($R^{39}$), hydroxy, COO($R^{40}$), N($R^{41}$)CO($C_1$-$C_6$)-alkyl, N($R^{42}$)($R^{43}$), $SO_2CH_3$, $SCF_3$ or S—($C_1$-$C_6$)-alkyl, and the ring system may be linked to A by =C($R^{43'}$);

$R^{35}$, $R^{36}$, $R^{37}$, $R^{38}$, $R^{39}$, $R^{40}$, $R^{41}$, $R^{42}$, $R^{43}$ and $R^{43'}$ are independently of one another H, or ($C_1$-$C_8$)-alkyl, or $R^{38}$ and $R^{39}$, or $R^{42}$ and $R^{43}$, are independently of one another taken together with the nitrogen atom to which they are bonded form a 5-6 membered ring which optionally comprises one additional heteroatom selected from the group of NH, N—($C_1$-$C_6$)-alkyl, oxygen and sulfur;

Q is mono-, bi-, tri- or spirocyclic saturated or partly unsaturated ring structure having one nitrogen atom and 1-3 further heteroatoms selected from the group of N, O and S, where the rings of the structure may be spiro-linked, fused or bridged, and where the ring system is optionally substituted one or more times by F, OH, $CF_3$, CN, $OCF_3$, oxo, O—($C_1$-$C_4$)-alkyl, ($C_1$-$C_4$)-alkoxy-($C_1$-$C_4$)-alkyl, ($C_1$-$C_6$)-alkyl, ($C_2$-$C_6$)-alkenyl, ($C_2$-$C_6$)-alkynyl, CO($R^{44}$), (C($R^{45}$)($R^{46}$))$_o$—$R^{47}$, CO(C($R^{45}$)($R^{46}$))$_p$—$R^{48}$, where Q comprises in total at least two N atoms;

$R^{44}$ is H, or ($C_1$-$C_8$)-alkyl;

$R^{45}$, and $R^{46}$ are independently of one another H, ($C_1$-$C_8$)-alkyl, OH, ($C_3$-$C_8$)-cycloalkyl, or ($C_1$-$C_4$)-alkoxy-($C_1$-$C_4$)-alkyl;

o and p are independently of one another 0, 1, 2, 3, 4, 5, or 6;

$R^{47}$, and $R^{48}$ are independently of one another OH, F, O—($C_1$-$C_8$)-alkyl, CON($R^{49}$)($R^{50}$), N($R^{51}$)CO($R^{52}$), N($R^{53}$)($R^{54}$), $CO_2$($R^{55}$), $SO_2$Me, CN, or a 3-10 membered ring system having 0 to 3 heteroatoms selected from the group consisting of N, O and S, and the 3-10 membered ring system is optionally substituted one or more times by F, Cl, Br, $CF_3$, ($C_1$-$C_8$)-alkyl, O—($C_1$-$C_8$)-alkyl, ($C_1$-$C_4$)-alkoxy-($C_1$-$C_4$)-alkyl, CO($R^{56}$), oxo, or OH;

$R^{49}$, $R^{50}$, $R^{51}$, $R^{52}$, $R^{55}$ and $R^{56}$ are independently of one another H, or ($C_1$-$C_8$)-alkyl, or $R^{49}$ and $R^{50}$ taken together with the nitrogen atom to which they are bonded form a 5-6 membered ring which optionally comprises one additional heteroatom selected from the group consisting of NH, N—($C_1$-$C_6$)-alkyl, oxygen and sulfur;

$R^{53}$ and $R^{54}$ are independently of one another H, ($C_1$-$C_8$)-alkyl, ($C_1$-$C_4$)-alkoxy-($C_1$-$C_4$)-alkyl, ($C_3$-$C_8$)-alkenyl, ($C_3$-$C_8$)-alkynyl, CO($R^{57}$), (C($R^{58}$)($R^{59}$))$_q$—$R^{60}$, CO(C($R^{61}$)($R^{62}$))$_r$—$R^{63}$, or CO—O($C_1$-$C_8$)-alkyl, or $R^{53}$ and $R^{54}$ taken together with the nitrogen atom to which they are bonded form a 4 to 10-membered mono-, bi- or spirocyclic ring which optionally comprises 1 to 3 additional heteroatoms selected from the group consisting of N, O and S, and is optionally substituted one or more times by F, Cl, Br, $CF_3$, CN, O—($C_1$-$C_8$)-alkyl, ($C_1$-$C_6$)-alkyl, CO($R^{64}$), oxo, OH, ($C_1$-$C_4$)-alkoxy-($C_1$-$C_4$)-alkyl, hydroxy-($C_1$-$C_4$)-alkyl, CON($R^{65}$)($R^{66}$), N($R^{67}$)CO($R^{68}$), N($R^{69}$)($R^{70}$), $CO_2$($R^{71}$), or $SO_2$($C_1$-$C_6$)-alkyl;

$R^{58}$ and $R^{59}$ are independently of one another H, ($C_1$-$C_6$)-alkyl, or OH;

$R^{57}$, $R^{61}$, $R^{62}$, $R^{64}$, $R^{65}$, $R^{66}$, $R^{67}$, $R^{68}$, $R^{69}$, $R^{70}$ and $R^{71}$ are independently of one another H, or ($C_1$-$C_6$)-alkyl, or $R^{69}$ and $R^{70}$ taken together with the nitrogen atom to which they are bonded form a 5-6 membered ring which optionally comprises one additional heteroatom from the group consisting of NH, N—($C_1$-$C_6$)-alkyl, oxygen and sulfur;

q and r are independently of one another 0, 1, 2, 3, 4, 5, or 6;

$R^{60}$ and $R^{63}$ are independently of one another OH, F, O—($C_1$-$C_6$)-alkyl, CN, COO($R^{78}$), N($R^{74}$)CO($C_1$-$C_6$)-alkyl, N($R^{76}$)($R^{77}$), CON($R^{72}$)($R^{73}$), $SO_2$($C_1$-$C_6$)-alkyl, or a 3-12 membered mono-, bi- or spirocyclic ring which optionally comprises one or more heteroatoms from the group consisting of N, O and S, and the 3-12 membered ring is optionally substituted by F, Cl, Br, OH, $CF_3$, $NO_2$, CN, $OCF_3$, oxo, O—($C_1$-$C_6$)-alkyl, ($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, N($R^{76}$)($R^{77}$), COO($R^{78}$), $SO_2$($C_1$-$C_6$)-alkyl or COOH; and $R^{72}$, $R^{73}$, $R^{74}$, $R^{76}$, $R^{77}$ and $R^{78}$ are independently of one another H, or ($C_1$-$C_8$)-alkyl, or $R^{72}$ and $R^{73}$, or $R^{76}$ and $R^{77}$, independently of one another taken together with the nitrogen atom to which they are bonded form a 5-6 membered ring which optionally comprises one additional heteroatom selected from the group consisting of NH, N—($C_1$-$C_6$)-alkyl, oxygen and sulfur;

or a pharmaceutical acceptable salt thereof.

2. The compound according to claim 1, wherein:

B is hydroxy-($C_1$-$C_4$)-alkyl, ($C_1$-$C_8$)-alkyl, ($C_1$-$C_4$)-alkoxy-($C_1$-$C_4$)-alkyl, ($C_2$-$C_8$)-alkenyl, ($C_2$-$C_8$)-alkynyl, or a 3 to 10-membered mono-, bi- or spirocyclic nonaromatic ring which optionally comprises 0 to 4 heteroatoms selected from the group consisting of oxygen, nitrogen and sulfur, wherein the ring system is optionally substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R$^{37}$), CON(R$^{38}$)(R$^{39}$), hydroxy, COO(R$^{40}$), N(R$^{41}$)CO(C$_1$-C$_6$)-alkyl, N(R$^{42}$)(R$^{43}$) or SO$_2$CH$_3$, and the ring system may be linked to A by =C(R$^{43'}$);

or a pharmaceutically acceptable salt thereof.

3. The compound according to claim 1, wherein:

B is hydroxy-(C$_1$-C$_4$)-alkyl, (C$_1$-C$_8$)-alkyl, (C$_1$-C$_4$)-alkoxy-(C$_1$-C$_4$)-alkyl, a 3 to 10-membered mono-, bi- or spirocyclic nonaromatic ring which optionally comprises 0 to 3 heteroatoms selected from the group consisting of oxygen, nitrogen and sulfur, wherein the ring system is optionally substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R$^{37}$), CON(R$^{38}$)(R$^{39}$), hydroxy, COO(R$^{40}$), N(R$^{41}$)CO(C$_1$-C$_6$)-alkyl, N(R$^{42}$)(R$^{43}$) or SO$_2$CH$_3$;

or a pharmaceutically acceptable salt thereof.

4. The compound according to claim 1, wherein:

B is (C$_1$-C$_8$)-alkyl, (C$_1$-C$_4$)-alkoxy-(C$_1$-C$_4$)-alkyl, or a 3 to 10-membered mono-, bi- or spirocyclic nonaromatic ring which optionally comprises 0 to 3 heteroatoms selected from the group consisting of oxygen, nitrogen and sulfur, wherein the ring system is optionally substituted by F, Cl, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R$^{37}$), hydroxy, N(R$^{41}$)CO(C$_1$-C$_6$)-alkyl, or SO$_2$CH$_3$;

or a pharmaceutically acceptable salt thereof.

5. The compound according to Formula I:

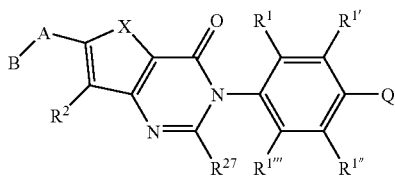

(I)

wherein:

R$^1$, R$^{1'}$, R$^{1''}$ and R$^{1'''}$ are independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R$^3$)(R$^4$), SO$_2$—CH$_3$, COOH, COO—(C$_1$-C$_6$)-alkyl, CON(R$^5$)(R$^6$), N(R$^7$)CO(R$^8$), N(R$^9$)SO$_2$(R$^{10}$), CO(R$^{11}$), or (C(R$^{12}$)(R$^{13}$))$_x$—O(R$^{14}$);

R$^3$, R$^4$, R$^5$, R$^6$, R$^7$ and R$^9$ are independently of one another H, or (C$_1$-C$_8$)-alkyl, or R$^3$ and R$^4$, or R$^5$ and R$^6$, independently of one another taken together with the nitrogen atom to which they are bonded form a 5-6 membered ring which optionally comprises one additional heteroatom selected from the group consisting of NH, N—(C$_1$-C$_6$)-alkyl, oxygen and sulfur;

R$^8$, R$^{10}$ and R$^{11}$ are independently of one another H, or (C$_1$-C$_8$)-alkyl;

R$^{12}$ and R$^{13}$ are independently of one another H, or (C$_1$-C$_8$)-alkyl;

R$^{14}$ is H, (C$_1$-C$_6$)-alkyl, or aryl;

x is 0, 1, 2, 3, 4, 5, or 6;

R$^2$ is H, F, Cl, Br, I, OH, CF$_3$, NO$_2$, CN, OCF$_3$, O—(C$_1$-C$_4$)-alkoxy-(C$_1$-C$_4$)-alkyl, S—(C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R$^{15}$)(R$^{16}$), SO$_2$—CH$_3$, COOH, COO—(C$_1$-C$_6$)-alkyl, CON(R$^{17}$)(R$^{18}$), N(R$^{19}$) CO(R$^{20}$), N(R$^{21}$)SO$_2$(R$^{22}$), CO(R$^{23}$), or (C(R$^{24}$)(R$^{25}$))$_{x'}$—O(R$^{26}$);

R$^{15}$, R$^{16}$, R$^{17}$, R$^{18}$, R$^{19}$ and R$^{21}$ are independently of one another H, (C$_1$-C$_8$)-alkyl, or R$^{15}$ and R$^{16}$, or R$^{17}$ and R$^{18}$, independently of one another taken together with the nitrogen atom to which they are bonded form a 5-6 membered ring which optionally comprises one additional heteroatom selected from the group consisting of NH, N—(C$_1$-C$_6$)-alkyl, oxygen and sulfur;

R$^{20}$, R$^{22}$ and R$^{23}$ are independently of one another H, or (C$_1$-C$_8$)-alkyl;

R$^{24}$ and R$^{25}$ are independently of one another H, or (C$_1$-C$_8$)-alkyl;

R$^{26}$ is H, (C$_1$-C$_6$)-alkyl, or aryl;

x' is 0, 1, 2, 3, 4, 5, or 6;

R$^{27}$ is H, or (C$_1$-C$_6$)-alkyl;

X is S;

A is a bond or a linker having 1 to 8 members, where the members are selected from the group consisting of O, S, SO$_2$, N(R$^{31}$), CO, C(R$^{32}$)(R$^{33}$), C(R$^{34}$)=C(R$^{34'}$), cyclopropylene, and C≡C, wherein the linker contains no O—CO or CO—O groups;

R$^{31}$, R$^{34}$ and R$^{34'}$ are independently of one another H, or (C$_1$-C$_8$)-alkyl;

R$^{32}$ and R$^{33}$ are independently of one another H, (C$_1$-C$_6$)-alkyl, OH, or O—(C$_1$-C$_6$)-alkyl;

B is N(R$^{35}$)(R$^{36}$), hydroxy-(C$_1$-C$_4$)-alkyl, (C$_1$-C$_4$)-alkoxy-(C$_1$-C$_4$)-alkyl, (C$_2$-C$_8$)-alkenyl, (C$_2$-C$_8$)-alkynyl, or a 3 to 10-membered mono-, bi-, tri- or spirocyclic nonaromatic ring which optionally comprises 0 to 4 heteroatoms selected from the group consisting of oxygen, nitrogen and sulfur, where the ring system is also optionally substituted one or more times by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R$^{37}$), CON(R$^{38}$)(R$^{39}$), hydroxy, COO(R$^{40}$), N(R$^{41}$)CO(C$_1$-C$_6$)-alkyl, N(R$^{42}$)(R$^{43}$), SO$_2$CH$_3$, SCF$_3$ or S—(C$_1$-C$_6$)-alkyl, and the ring system may be linked to A by =C(R$^{43'}$);

R$^{35}$, R$^{36}$, R$^{37}$, R$^{38}$, R$^{39}$, R$^{40}$, R$^{41}$, R$^{42}$, R$^{43}$ and R$^{43'}$ are independently of one another H, or (C$_1$-C$_8$)-alkyl, or R$^{38}$ and R$^{39}$, or R$^{42}$ and R$^{43}$, are independently of one another taken together with the nitrogen atom to which they are bonded form a 5-6 membered ring which optionally comprises one additional heteroatom selected from the group of NH, N—(C$_1$-C$_6$)-alkyl, oxygen and sulfur;

Q is a group of formula:

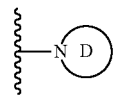

wherein the ring D is a saturated monocyclic 5-7-membered azacycle which comprises a moiety $N(R^{53})$ or $C(R^{45})((CH_2)_o-N(R^{53})(R^{54}))$; or a saturated 6-11 membered azabicycle or spirocycle which comprises a moiety $N(R^{53})$ or $C(R^{45})((CH_2)_o-N(R^{53})(R^{54}))$;
wherein
each of the ring positions capable of substitution is optionally substituted one or more times by F, OH, oxo, $(C_1-C_6)$-alkyl, O—$(C_1-C_6)$-alkyl, $(C_1-C_4)$-alkoxy-$(C_1-C_4)$-alkyl;
$R^{45}$ is H, or $(C_1-C_6)$-alkyl; $R^{53}$ and $R^{54}$ are
independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $CO(R^{57})$, $(C(R^{58})(R^{59}))_q—R^{60}$, $CO(C(R^{61})(R^{62}))_r—R^{63}$, or CO—$O(C_1-C_8)$-alkyl, or $R^{53}$ and $R^{54}$ taken together with the nitrogen atom to which they are bonded form a 4 to 10-membered mono-, bi- or spirocyclic ring which optionally comprises 1 to 3 additional heteroatoms selected from the group consisting of N, O and S, and is optionally substituted one or more times by F, Cl, Br, $CF_3$, CN, O—$(C_1-C_8)$-alkyl, $(C_1-C_6)$-alkyl, $CO(R^{64})$, oxo, OH, $(C_1-C_4)$-alkoxy-$(C_1-C_4)$-alkyl, hydroxy-$(C_1-C_4)$-alkyl, $CON(R^{65})(R^{66})$, $N(R^{67})CO(R^{68})$, $N(R^{69})(R^{70})$, $CO_2(R^{71})$, or $SO_2(C_1-C_6)$-alkyl;
$R^{58}$ and $R^{59}$ are independently of one another H, $(C_1-C_6)$-alkyl, or OH;
$R^{57}, R^{61}, R^{62}, R^{64}, R^{65}, R^{66}, R^{67}, R^{68}, R^{69}, R^{70}$ and $R^{71}$ are
independently of one another H, or $(C_1-C_6)$-alkyl,
q and r are independently of one another 0, 1, 2, 3, 4, 5, or 6;
$R^{60}$ and $R^{63}$ are
independently of one another OH, F, O—$(C_1-C_6)$-alkyl, CN, $COO(R^{78})$, $N(R^{74})CO(C_1-C_6)$-alkyl, $N(R^{76})(R^{77})$, $CON(R^{72})(R^{73})$, $SO_2(C_1-C_6)$-alkyl, or a 3-12 membered mono-, bi- or spirocyclic ring which optionally comprises one or more heteroatoms from the group consisting of N, 0 and S, and the 3-12 membered ring is optionally substituted by F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $N(R^{76})(R^{77})$, $COO(R^{78})$, $SO_2(C_1-C_6)$-alkyl or COOH; and
$R^{72}, R^{73}, R^{74}, R^{76}, R^{77}$ and $R^{78}$ are
independently of one another H, or $(C_1-C_8)$-alkyl,
or
$R^{72}$ and $R^{73}$, or $R^{76}$ and $R^{77}$,
independently of one another taken together with the nitrogen atom to which they are bonded form a 5-6 membered ring which optionally comprises one additional heteroatom selected from the group consisting of NH, N—$(C_1-C_6)$-alkyl, oxygen and sulfur;
and
o is 0, 1, 2, 3, 4, 5, or 6; q and r are independently of one another 0, 1, 2, 3, 4, 5, or 6;
or a pharmaceutically acceptable salt thereof.

6. The compound according to claim 5, wherein Q is

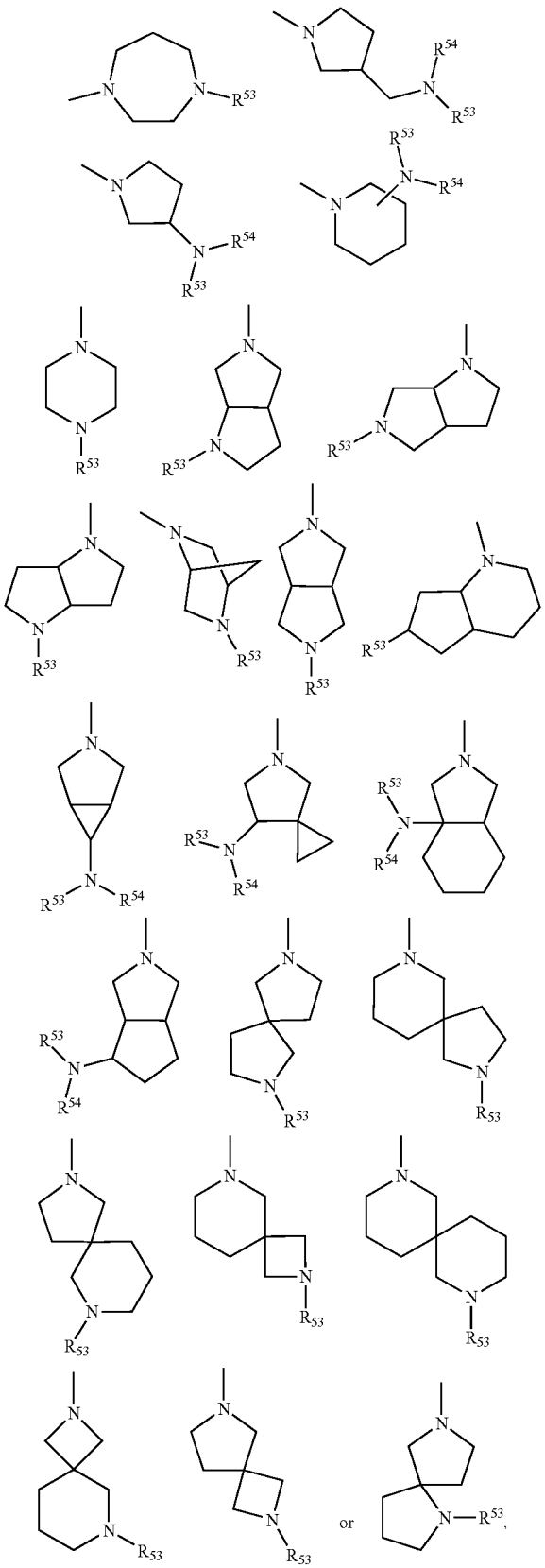

each of the ring positions capable of substitution is optionally substituted one or more times by F, OH, oxo, $(C_1-C_6)$-alkyl, $O-(C_1-C_6)$-alkyl, $(C_1-C_4)$-alkoxy-$(C_1-C_4)$-alkyl;

or a pharmaceutically acceptable salt thereof.

7. The compound according to claim 5, wherein Q is

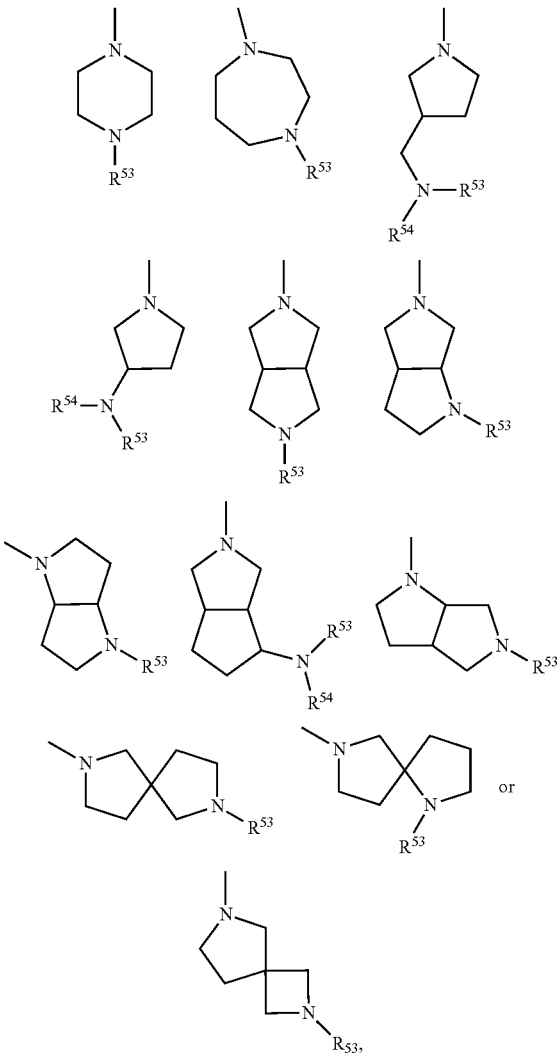

each of the ring positions capable of substitution is optionally substituted one or more times by F, OH, oxo, $(C_1-C_6)$-alkyl, $O-(C_1-C_6)$-alkyl, or $(C_1-C_4)$-alkoxy-$(C_1-C_4)$-alkyl;

or a pharmaceutically acceptable salt thereof.

8. The compound according to claim 5, wherein Q is

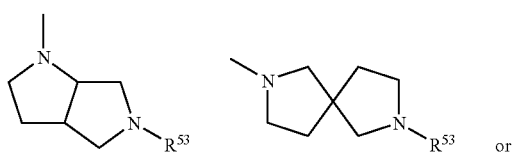

-continued

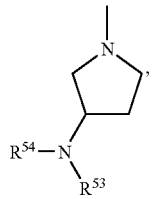

each of the ring positions capable of substitution is optionally substituted one or more times by F, OH, oxo, $(C_1-C_6)$-alkyl, $O-(C_1-C_6)$-alkyl, or $(C_1-C_4)$-alkoxy-$(C_1-C_4)$-alkyl;

or a pharmaceutically acceptable salt thereof.

9. The compound according to claim 5, wherein Q is

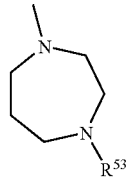

each of the ring positions capable of substitution is optionally substituted one or more times by F, OH, oxo, $(C_1-C_6)$-alkyl, $O-(C_1-C_6)$-alkyl, $(C_1-C_4)$-alkoxy-$(C_1-C_4)$-alkyl;

or a pharmaceutically acceptable salt thereof.

10. The compound according to claim 5, wherein Q is each of the ring positions capable of substitution is optionally substituted one or more times by F, OH, oxo, $(C_1-C_6)$-alkyl, $O-(C_1-C_6)$-alkyl, $(C_1-C_4)$-alkoxy-$(C_1-C_4)$-alkyl;

or a pharmaceutically acceptable salt thereof.

11. The compound according to claim 1, wherein:

$R^{53}$ is H, $(C_1-C_8)$-alkyl, $(C(R^{58})(R^{59}))_q-R^{60}$, $(C_1-C_4)$-alkoxy-$(C_1-C_4)$-alkyl, $(C_3-C_8)$-alkenyl, $(C_3-C_8)$-alkynyl, $CO-O(C_1-C_8)$-alkyl, or $CO(C(R^{61})(R^{62}))_r N(R^{76})(R^{77})$, $R^{54}$ is $(C_1-C_8)$-alkyl, $(C(R^{58})(R^{59}))_q-R^{60}$, $(C_1-C_4)$-alkoxy-$(C_1-C_4)$-alkyl, $(C_3-C_8)$-alkenyl, or $(C_3-C_8)$-alkynyl, or $R^{53}$ and $R^{54}$ taken together with the nitrogen atom to which they are bonded form a 4 to 10-membered mono-, bi- or spirocyclic ring which optionally comprises 1 to 3 additional heteroatoms selected from the group consisting of oxygen, nitrogen and sulfur, wherein the heterocyclic ring system is optionally substituted by F, Cl, Br, $CF_3$, $(C_1-C_6)$-alkyl, $O-(C_1-C_8)$-alkyl, $(C_1-C_4)$-alkoxy-$(C_1-C_4)$-alkyl, hydroxy-$(C_1-C_4)$-alkyl, oxo, $CO(R^{64})$, $CON(R^{65})(R^{66})$, hydroxy, $COO(R^{71})$, $N(R^{67})CO(C_1-C_6)$-alkyl, $N(R^{69})(R^{70})$ or $SO_2(C_1-C_6)$-alkyl;

or a pharmaceutically acceptable salt thereof.

12. The compound according to claim 1, wherein:

$R^{53}$ and $R^{54}$ independently of one another are $(C_1-C_8)$-alkyl, $(C(R^{58})(R^{59}))_q-R^{60}$, or $(C_1-C_4)$-alkoxy-$(C_1-C_4)$-alkyl, or $R^{53}$ and $R^{54}$ taken together with the nitrogen atom to which they are bonded form a 4 to 10-membered mono-, bi- or spirocyclic ring which optionally comprises 1 to 2 additional heteroatoms selected from the group consisting of oxygen, nitrogen and sulfur, wherein the heterocyclic ring system is optionally substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, $CO(R^{64})$, hydroxy, $N(R^{67})CO(C_1-C_6)$-alkyl, or $SO_2(C_1-C_6)$-alkyl;

or a pharmaceutically acceptable salt thereof.

13. The compound according to claim 1, wherein:

$R^{60}$, and $R^{63}$ are independently of one another OH, F, O—$(C_1-C_6)$-alkyl, $N(R^{74})CO(C_1-C_6)$-alkyl, $SO_2(C_1-C_6)$-alkyl, or a 3-12 membered mono-, bi- or spirocyclic ring which optionally comprises one or more heteroatoms from the group consisting of N, O and S, and the 3-12 membered ring is optionally substituted by F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, $N(R^{76})(R^{77})$ or $SO_2(C_1-C_6)$-alkyl;

or a pharmaceutically acceptable salt thereof.

14. The compound according to claim 1, wherein:

A is a bond or a linker having 1 to 6 members, where the members are selected from the group consisting of O, $SO_2$, $N(R^{31})$, CO, $C(R^{32})(R^{33})$, $C(R^{34})=C(R^{34'})$, and $C\equiv C$, $R^{31}$, $R^{34}$ and $R^{34'}$ are independently of one another H, or $(C_1-C_8)$-alkyl; and $R^{32}$, and $R^{33}$ are independently of one another H, $(C_1-C_6)$-alkyl, OH, or O—$(C_1-C_6)$-alkyl;

or a pharmaceutically acceptable salt thereof.

15. The compound according to claim 1, wherein:

$R^2$ is H, F, Cl, O—$(C_1-C_6)$-alkyl, or $(C_1-C_6)$-alkyl;

or a pharmaceutically acceptable salt thereof.

16. The compound according to claim 5, wherein:

$R^1$, $R^{1'}$, $R^{1''}$ and $R^{1'''}$ are independently of one another H, F, Cl, OH, CN, O—$(C_1-C_6)$-alkyl, or $(C_1-C_6)$-alkyl;

$R^2$ is H;

$R^{27}$ is H, or $(C_1-C_6)$-alkyl;

X is S;

A is a bond or a linker having 1 to 5 members, where the members are selected from the group consisting of O, $N(R^{31})$, CO, $C(R^{32})(R^{33})$, $C(R^{34})=C(R^{34'})$, and $C\equiv C$, wherein the linker contains no O—CO or CO—O groups;

$R^{31}$, $R^{34}$ and $R^{34'}$ are independently of one another H, or $(C_1-C_8)$-alkyl;

$R^{32}$, and $R^{33}$ are independently of one another H, $(C_1-C_8)$-alkyl, OH, or O—$(C_1-C_6)$-alkyl;

B is hydroxy-$(C_1-C_8)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, or a 3 to 7-membered monocyclic nonaromatic ring which optionally comprises 0 to 2 heteroatoms selected from the group consisting of oxygen and nitrogen, wherein the ring system is optionally substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, $CO(R^{37})$, or hydroxy;

$R^{37}$ is H, $(C_1-C_8)$-alkyl;

Q is a group selected from

[structures of Q groups]

$R^{53}$ and $R^{54}$ are independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $CO(R^{57})$, $(C(R^{58})(R^{59}))_q-R^{60}$, $CO(C(R^{61})(R^{62}))_r-R^{63}$, or CO—O$(C_1-C_8)$-alkyl, or $R^{53}$ and $R^{54}$ taken together with the nitrogen atom to which they are bonded form a 4 to 10-membered mono-, bi- or spirocyclic ring which optionally comprises 0 to 2 additional heteroatoms selected from the group consisting of N, O and S, and is optionally substituted one or more times by F, Cl, Br, $CF_3$, $(C_1-C_6)$-alkyl, O—$(C_1-C_6)$-alkyl, $(C_1-C_4)$-alkoxy-$(C_1-C_4)$-alkyl, hydroxy-$(C_1-C_4)$-alkyl, oxo, $CO(R^{64})$, hydroxy, $N(R^{67})CO(C_1-C_6)$-alkyl or $SO_2(C_1-C_6)$-alkyl;

$R^{58}$ and $R^{59}$ are independently of one another H, $(C_1-C_6)$-alkyl, or OH;

$R^{57}$, $R^{61}$, $R^{62}$, $R^{64}$ and $R^{67}$ are independently of one another H, or $(C_1-C_6)$-alkyl;

q and r are independently of one another 0, 1, or 2;

$R^{60}$ and $R^{63}$ are independently of one another OH, F, O—$(C_1-C_6)$-alkyl, $N(R^{74})CO(C_1-C_6)$-alkyl, $N(R^{76})(R^{77})$, $CON(R^{72})(R^{73})$, $SO_2(C_1-C_6)$-alkyl, or a 3-12 membered mono-, bi- or spirocyclic ring which optionally comprises one to three heteroatoms from the group consisting of N, O and S, and the 3-12 membered ring is optionally substituted by F, Cl, Br, OH, $CF_3$, $NO_2$, CN, $OCF_3$, oxo, O—$(C_1$-$C_6)$-alkyl, $(C_1$-$C_4)$-alkoxy-$(C_1$-$C_4)$-alkyl, $(C_1$-$C_6)$-alkyl, $(C_2$-$C_6)$-alkenyl, $(C_2$-$C_6)$-alkynyl, $N(R^{76})(R^{77})$ and $SO_2$ $(C_1$-$C_6)$-alkyl; and $R^{72}$, $R^{73}$, $R^{74}$, $R^{76}$ and $R^{77}$ are independently of one another H, or $(C_1$-$C_8)$-alkyl;

or a pharmaceutically acceptable salt thereof.

17. The compound according to claim 5, wherein:

$R^1$, $R^{1\prime}$, $R^{1\prime\prime\prime}$ and $R^{1\prime\prime\prime\prime}$ are independently of one another H, F, Cl, O-methyl, or methyl;

$R^2$ is H;

$R^{27}$ is H;

X is S;

A is a bond or an moiety selected from the group consisting of O, $CH_2$, CO, O—$CH_2$, CHOH, $CH_2$—$CH_2$, CH=CH, C($CH_3$)=CH, C≡C, $CH_2$—O, $N(CH_3)CO$, NH—CO, $CH_2$—O—$CH_2$, O—CH=CH, C(OH)($CH_3$)—$CH_2$—$CH_2$, and C(OH)($CH_3$)—C≡C; and B is hydroxy-$(C_1$-$C_4)$-alkyl, $(C_1$-$C_8)$-alkyl, $(C_1$-$C_4)$-alkoxy-$(C_1$-$C_4)$-alkyl, $(C_2$-$C_8)$-alkenyl, $(C_2$-$C_8)$-alkynyl, or a 3-6 membered nonaromatic monocyclic ring selected from the group consisting of:

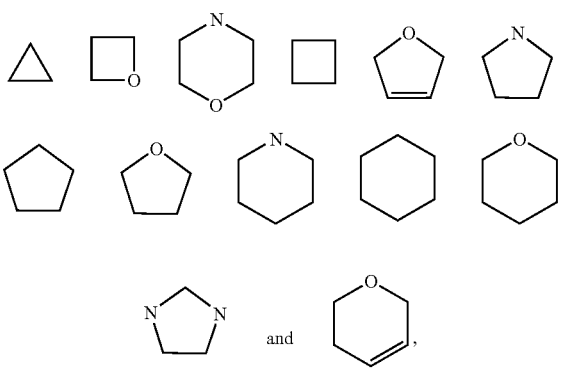

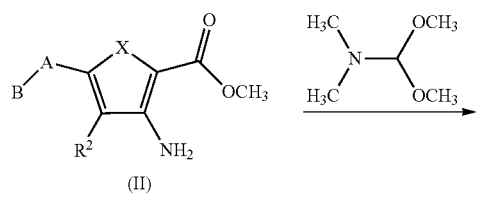

where the 3-6 membered nonaromatic monocyclic ring is optionally substituted by methyl, ethyl, OH, or oxo;

or a pharmaceutically acceptable salt thereof.

18. A process for preparing the compound according to claim 1, wherein $R^{27}$ is H, comprising:

i) reacting an aromatic ortho-amino carboxylic ester of formula (II) with dimethylformamide dimethyl acetal to give corresponding aminal of formula (III):

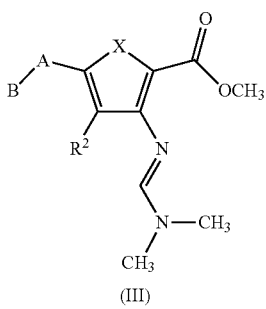

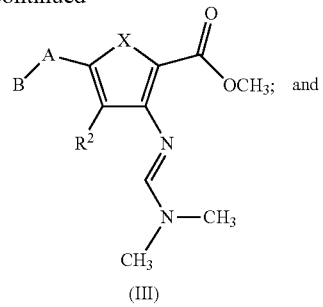

(III)

ii) reacting the aminal of formula (III) with a substituted primary aromatic amine of formula (IV)

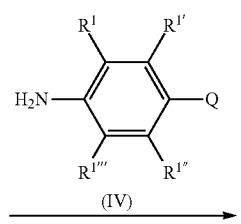

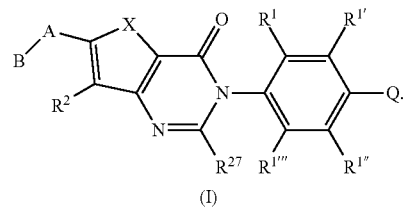

19. A pharmaceutical composition comprising the compound according to claim 1 or a pharmaceutically acceptable salt thereof, in combination with at least one pharmaceutically acceptable carrier.

20. A pharmaceutical composition comprising the compound according to claim 1 or a pharmaceutically acceptable salt thereof, and at least one additional active ingredient which has beneficial effect on metabolic disturbance.

21. A pharmaceutical composition comprising the compound according to claim 1 or a pharmaceutically acceptable salt thereof, and at least one antidiabetic active ingredient.

22. A pharmaceutical composition comprising the compound according to claim 1 or a pharmaceutically acceptable salt thereof, and at least one lipid modulator.

23. A pharmaceutical composition comprising the compound according to claim 1 or a pharmaceutically acceptable salt thereof, and at least one antiobesity active ingredient.

24. A pharmaceutical composition comprising the compound according to claim 5 or a pharmaceutically acceptable salt thereof, in combination with at least one pharmaceutically acceptable carrier.

25. A pharmaceutical composition comprising the compound according to claim 5 or a pharmaceutically acceptable salt thereof, and at least one additional active ingredient which has beneficial effect on metabolic disturbance.

26. A pharmaceutical composition comprising the compound according to claim 5 or a pharmaceutically acceptable salt thereof, and at least one antidiabetic active ingredient.

27. A pharmaceutical composition comprising the compound according to claim 5 or a pharmaceutically acceptable salt thereof, and at least one lipid modulator.

28. A pharmaceutical composition comprising the compound according to claim 5 or a pharmaceutically acceptable salt thereof, and at least one antiobesity active ingredient.

* * * * *